US010161940B2

(12) United States Patent
Platten et al.

(10) Patent No.: US 10,161,940 B2
(45) Date of Patent: Dec. 25, 2018

(54) MEANS AND METHODS FOR TREATING OR DIAGNOSING IDH1 R132H MUTANT-POSITIVE CANCERS

(71) Applicants: DEUTSCHES KREBSFORSCHUNGSZENTRUM, Heidelberg (DE); RUPRECHT-KARLS-UNIVERSITÄT, Heidelberg (DE)

(72) Inventors: Michael Platten, Dossenheim (DE); Theresa Bunse, Heidelberg (DE); Wolfgang Wick, Heidelberg (DE)

(73) Assignees: DEUTSCHES KREBSFORSCHUNGSZENTRUM, Heidelberg (DE); RUPRECHT-KARLS-UNIVERISTAET HEIDELBERG, Heidelberg (DE)

( * ) Notice: Subject to any disclaimer, the term of this patent is extended or adjusted under 35 U.S.C. 154(b) by 0 days.

(21) Appl. No.: 14/370,224

(22) PCT Filed: Jan. 3, 2013

(86) PCT No.: PCT/EP2013/050048
§ 371 (c)(1),
(2) Date: Jul. 2, 2014

(87) PCT Pub. No.: WO2013/102641
PCT Pub. Date: Jul. 11, 2013

(65) Prior Publication Data
US 2015/0023991 A1 Jan. 22, 2015

(30) Foreign Application Priority Data
Jan. 5, 2012 (EP) .................................. 12150298

(51) Int. Cl.
*G01N 33/00* (2006.01)
*A61K 38/43* (2006.01)
*G01N 33/574* (2006.01)
*C12N 9/04* (2006.01)
*A61K 39/00* (2006.01)

(52) U.S. Cl.
CPC ....... *G01N 33/57496* (2013.01); *A61K 38/43* (2013.01); *C12N 9/0006* (2013.01); *G01N 33/57407* (2013.01); *G01N 33/57426* (2013.01); *A61K 39/0011* (2013.01); *C12Y 101/01042* (2013.01); *G01N 2333/904* (2013.01)

(58) Field of Classification Search
CPC ....................................................... A61K 38/43
See application file for complete search history.

(56) References Cited

U.S. PATENT DOCUMENTS

| 8,367,347 B2* | 2/2013 | Hartmann et al. ............. 435/7.1 |
| 8,685,660 B2* | 4/2014 | Vogelstein ........... C12Q 1/6886 424/141.1 |
| 2011/0229479 A1* | 9/2011 | Vogelstein ........... C12Q 1/6886 424/138.1 |
| 2012/0070450 A1* | 3/2012 | Ishikawa .............. A61K 31/713 424/173.1 |
| 2012/0121515 A1* | 5/2012 | Dang ............. C12Y 101/01042 424/9.3 |
| 2012/0202207 A1* | 8/2012 | Vogelstein ........... C12Q 1/6886 435/6.11 |

FOREIGN PATENT DOCUMENTS

EP  2253716 A1  11/2010
EP  2256214 A1  12/2010
(Continued)

OTHER PUBLICATIONS

Turner et al. (J. Clin. Oncol. 2001, 19(4): 992-1000).*
Tang et al. (J. Clin. Oncol. 1999, 17(6): 1710-1719).*
Krajewska et al. (Prostate, 2006, 66:801-810).*
Bralten (Annals of Neurology (Mar. 1, 2011) 69(3): 455-463).*
Kyritsis (Neuro-Oncology (Nov. 23, 2009) 12(1): 104-113).*
Urbani et al., 1995, Defective Expression of Interferon—_, Granulocyte-Macrophage Colony-Stimulating Factor, Tumor Necrosis Factor _, and Interleukin-6 in Activated Peripheral Blood Lymphocytes from Glioma Patients, Journal of Interferon and Cytokine Research, 15: 421-429.*

(Continued)

Primary Examiner — Amber D Steele
(74) Attorney, Agent, or Firm — McBee Moore Woodward & Vanik IP, LLC

(57) ABSTRACT

The present invention concerns the field of tumor therapeutics and diagnostics. Specifically, it relates to a peptide comprising at least 8 amino acids in length which are present as contiguous amino acid sequence in the human Isocitratdehydrogenase Type 1 (IDH1), wherein said peptide has at least one amino acid exchange from R to H at a position corresponding to position 132, for use in preventing and/or treating cancer. Further contemplated is a medicament comprising the said peptide. Furthermore, the invention relates to a method for diagnosing cancer characterized by having a mutation in the genome of at least some cancer cells which results in the expression of a mutant IDH1 having the R132H mutation comprising the steps of contacting a blood sample of a subject suspected to suffer from such a cancer with a peptide comprising at least 10 amino acids in length which are present as contiguous amino acid sequence in the IDH1, wherein said peptide has at least one amino acid exchange from R to H at a position corresponding to position 132 for a time and under conditions which allow for specific binding of a component of the immune system to the peptide, and determining whether, or not, binding of the said component of the immune system to the peptide occurred, wherein the cancer is diagnosed if the occurrence of binding has been determined. Provided by the invention is also a kit and a device for carrying out said method.

10 Claims, 49 Drawing Sheets

Figure 1:
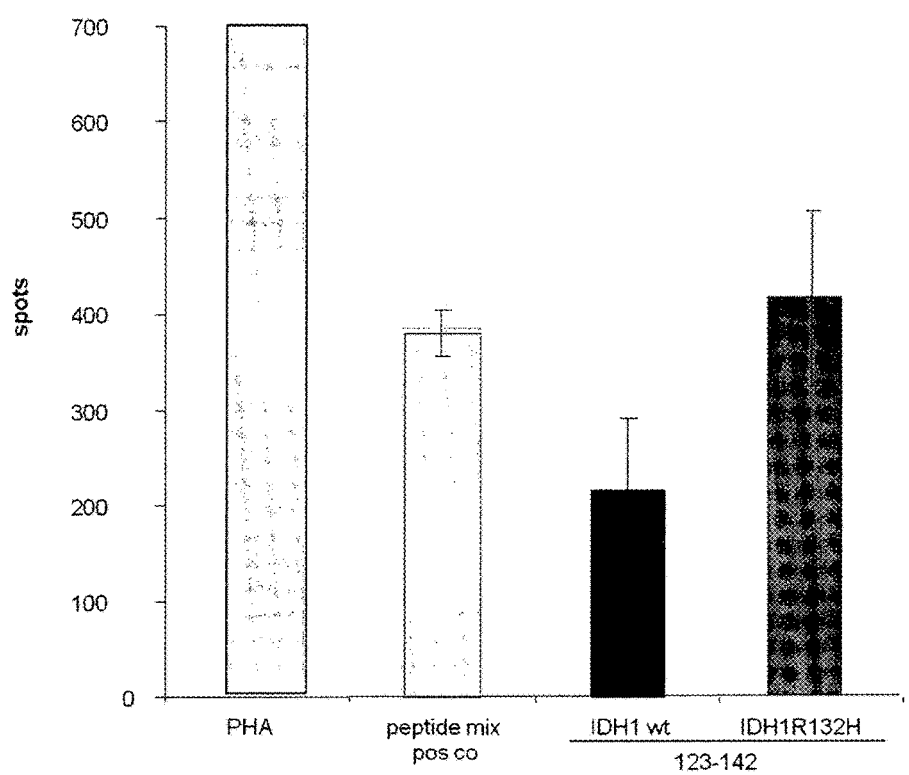
Figure 1:
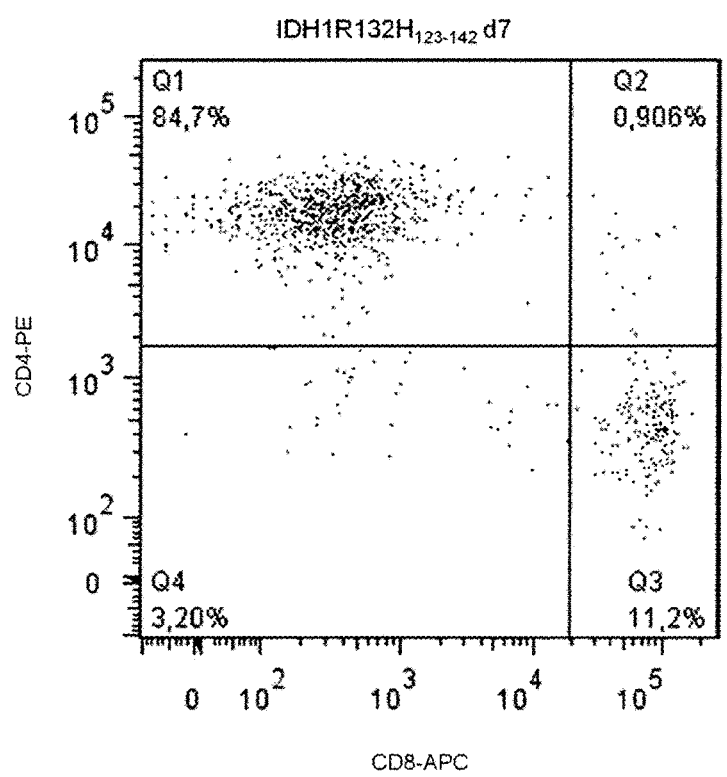

Specification includes a Sequence Listing.

(56) References Cited

FOREIGN PATENT DOCUMENTS

| WO | 2010028099 A1 | | 9/2009 | |
| WO | WO 2010/028099 | * | 3/2010 | ............... C12Q 1/68 |
| WO | 2010105243 A1 | | 9/2010 | |

OTHER PUBLICATIONS

Yang et al., 2011, The Influence of Lipid Characteristics on the Formation, in vitro Release, and in vivo Absorption of Protein-Loaded SLN Prepared by the Double Emulsion Process, Drug Development and Industrial Pharmacy, 37(2): 139-148.*

International Search Report received in PCT/EP2013/050048, dated Apr. 17, 2013.

Bralten, et al., IDH1 R132H Decreases Proliferation of Glioma Cell Lines in Vitro and In Vivo, Rapid Communication, Mar. 2011 American Neurological Association, pp. 455-463.

Kato, et al., A monoclonal antibody IMab-1 specifically recognizes IDH1R132H, the most common glioma-derived mutation, Biochemical and Biophysical Research Communications, 390 (2009) pp. 547-551.

Capper, et al., Monoclonal antibody specific for IDH1 R132H mutation, Acta Neuropathal (2009) pp. 599-601.

* cited by examiner

Fig. 4

| donor ID | MHC haplotype | IDH1 status | Glioma type | Anti-IDH1 (15mers) IgG |
|---|---|---|---|---|
| patTS060462 | A*0301;2402 DRB1*1201;15 | R132H | GBM | - |
| patTL260878 | nd | ? | GBM | RH$_{123-138}$ |
| patJP270454 | nd | R132H | OA °II | RH$_{123-138}$ |
| patAW041083 | nd | ? | OA °II | - |
| patWG063257 | nd | ? | A °II | RH$_{123-138}$ |
| patSS080462 | nd | R132H | O °II | RH$_{123-138}$ |
| patMA290158 | nd | R132H | A °II | RH$_{123-138}$ |
| patSG080572 | nd | R132H | A °II | RH$_{123-138}$ |
| AH | A*02;26 DRB1*07;15 | - | - | - |
| TL | A*11;31 DRB1*03;04 | - | - | - |
| TS | A*11;34 DRB1*01;13 | - | - | - |
| glioma patients | n.a. | R132H wt ? | °II – °IV | 15.4 % (4/26) 0.0 % (0/20) 18.2 % (2/11) |
| healthy donors | various | wt | - | 0 % (0/5) |

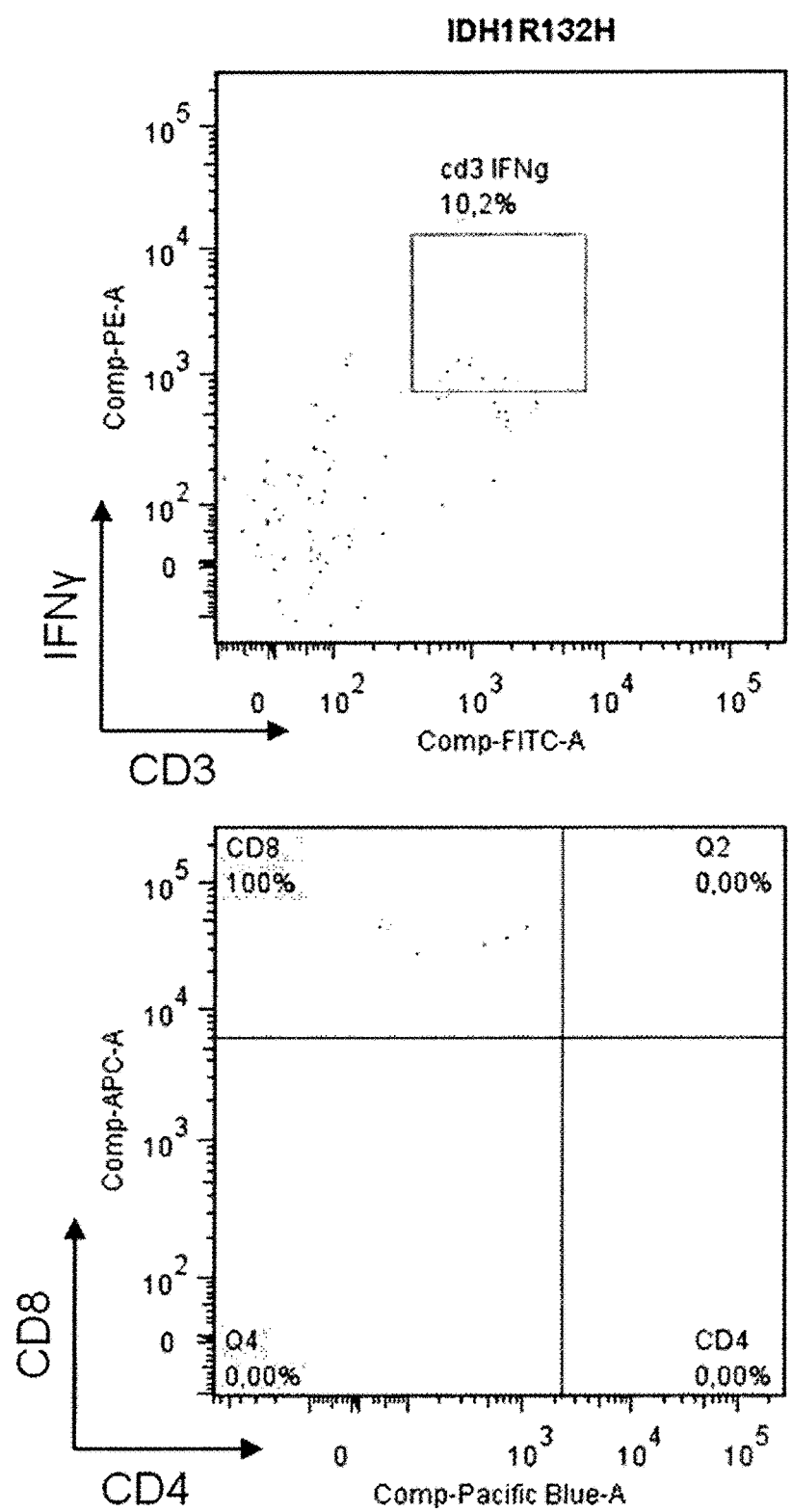
Fig. 14 A(1)

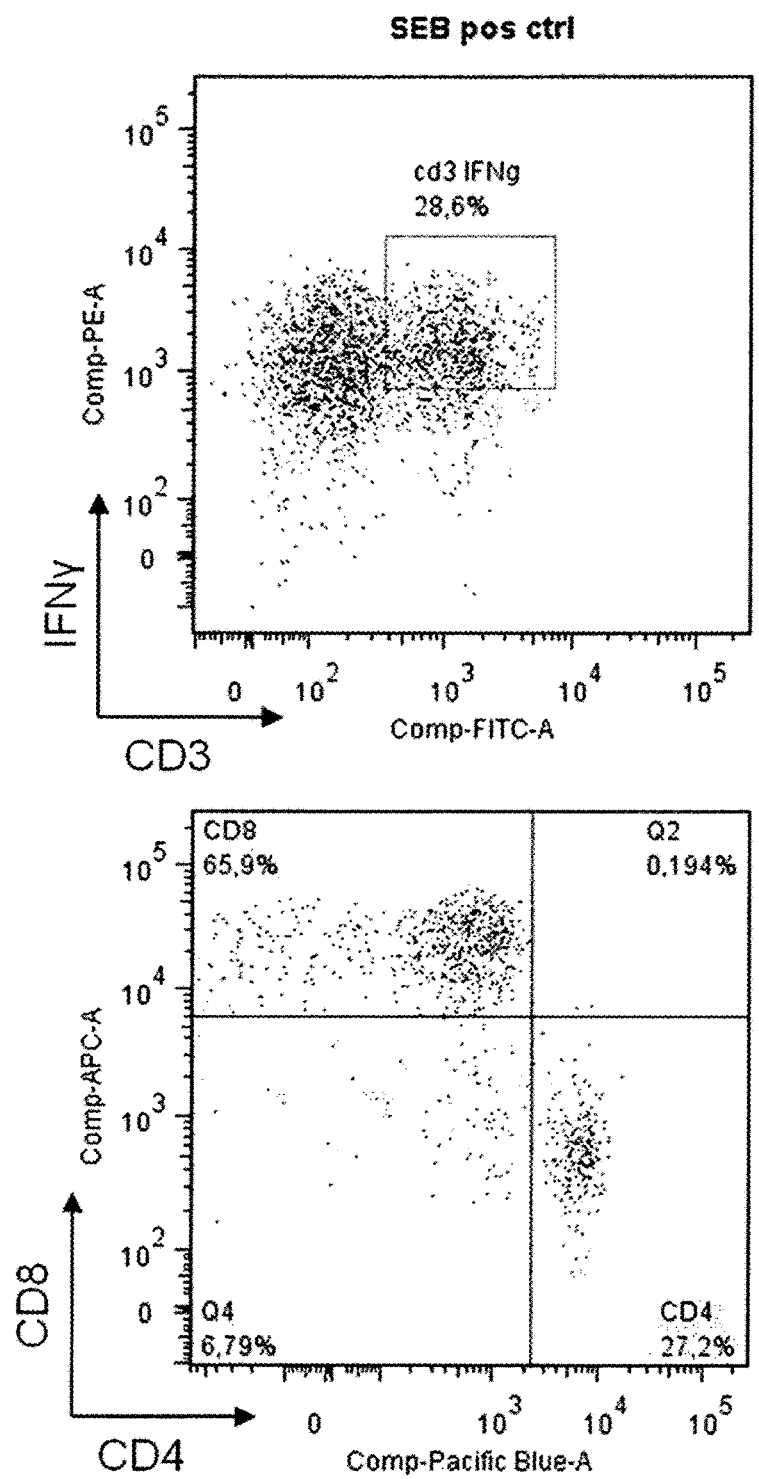
Fig. 14 A(2)

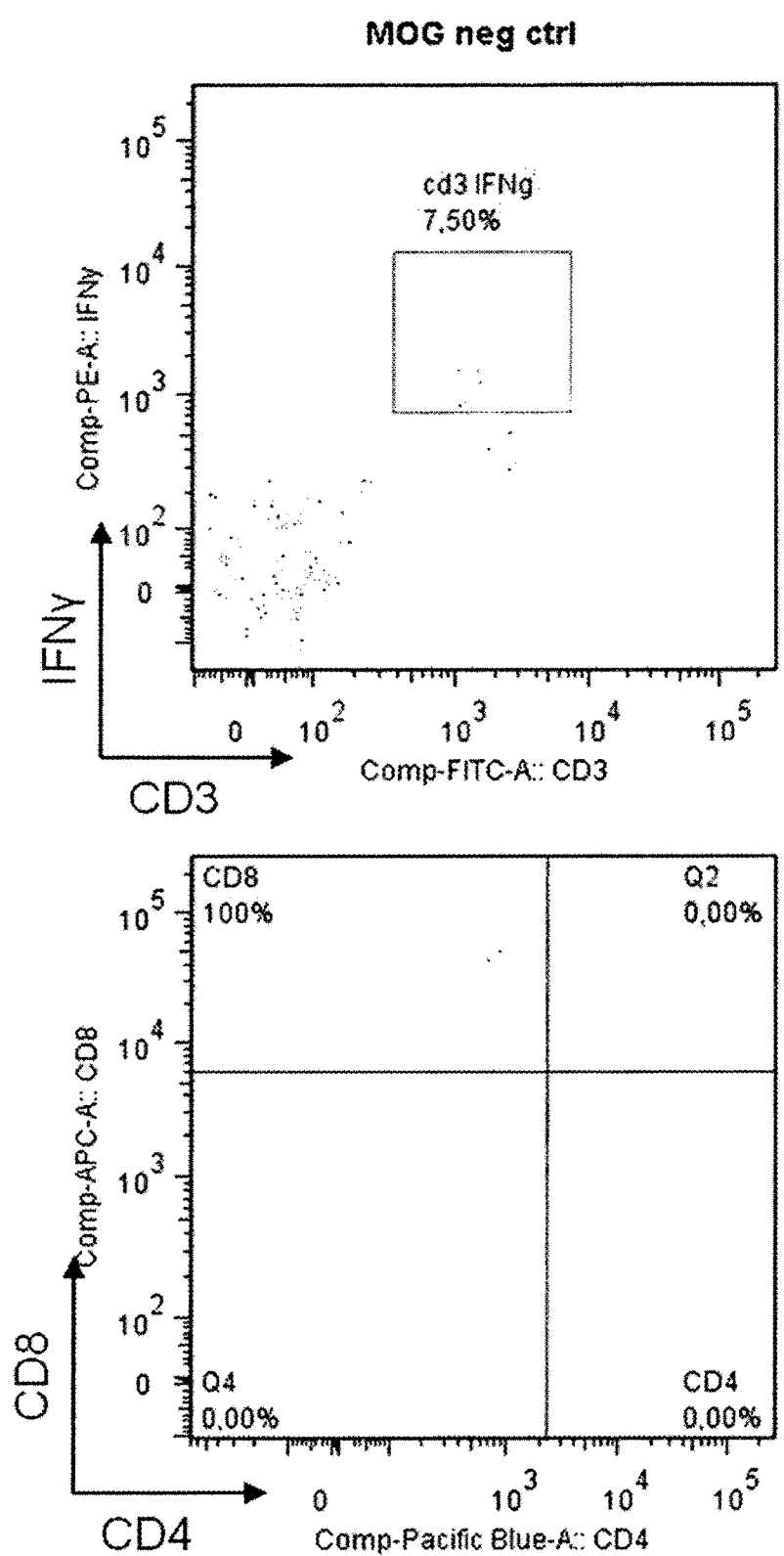
Fig. 14 A(3)

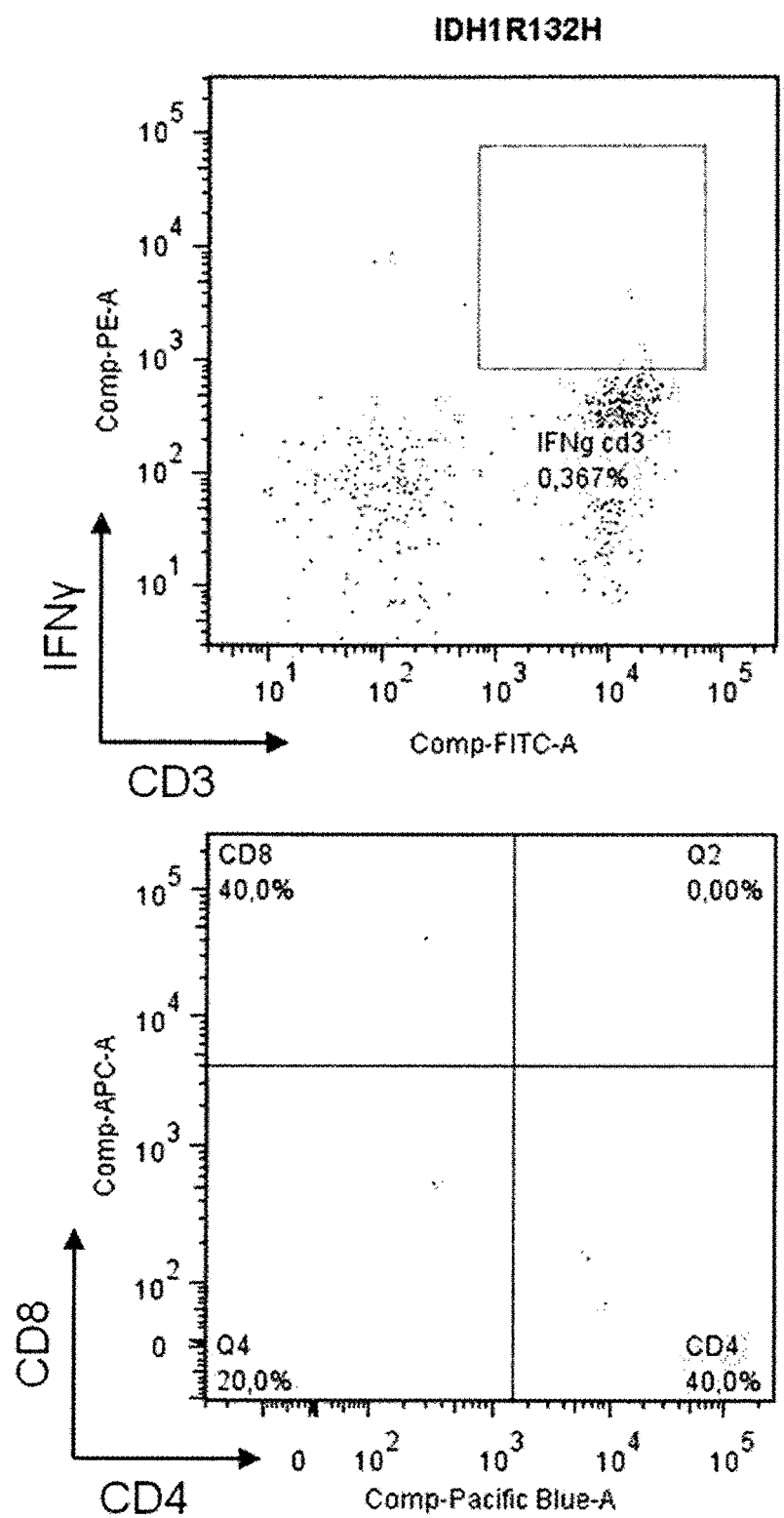
Fig. 14 B(1)

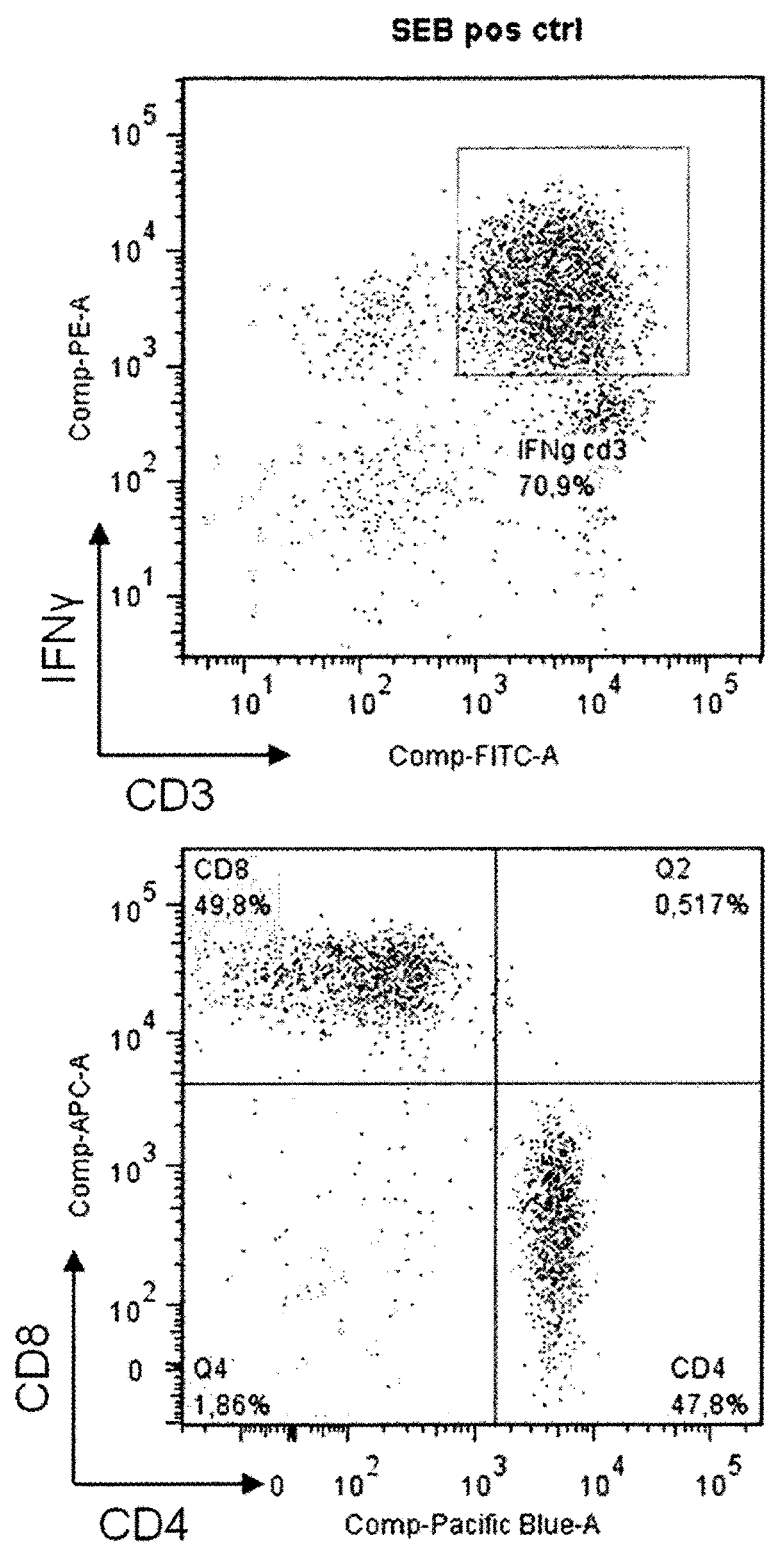
Fig. 14 B(2)

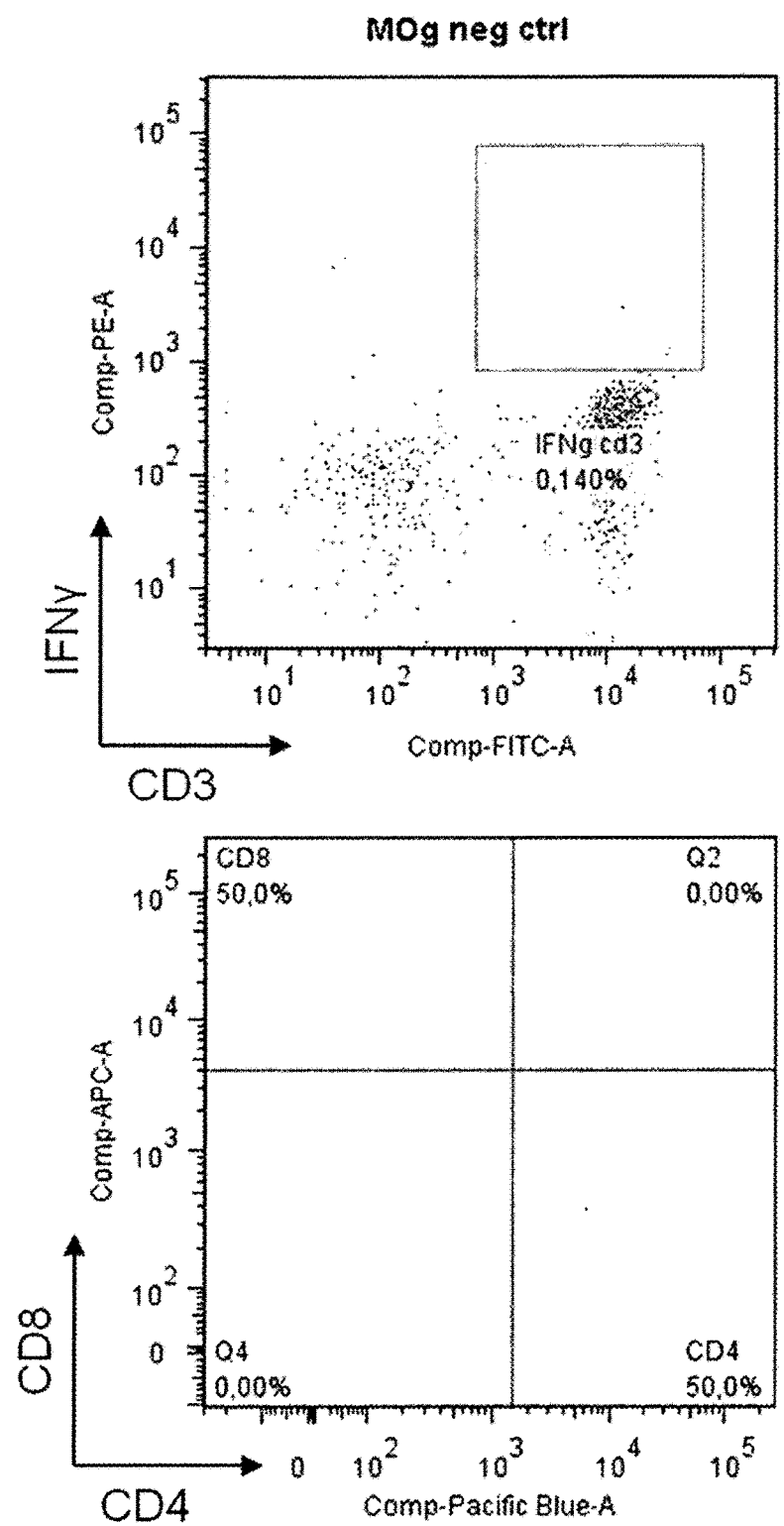
Fig. 14 B(3)

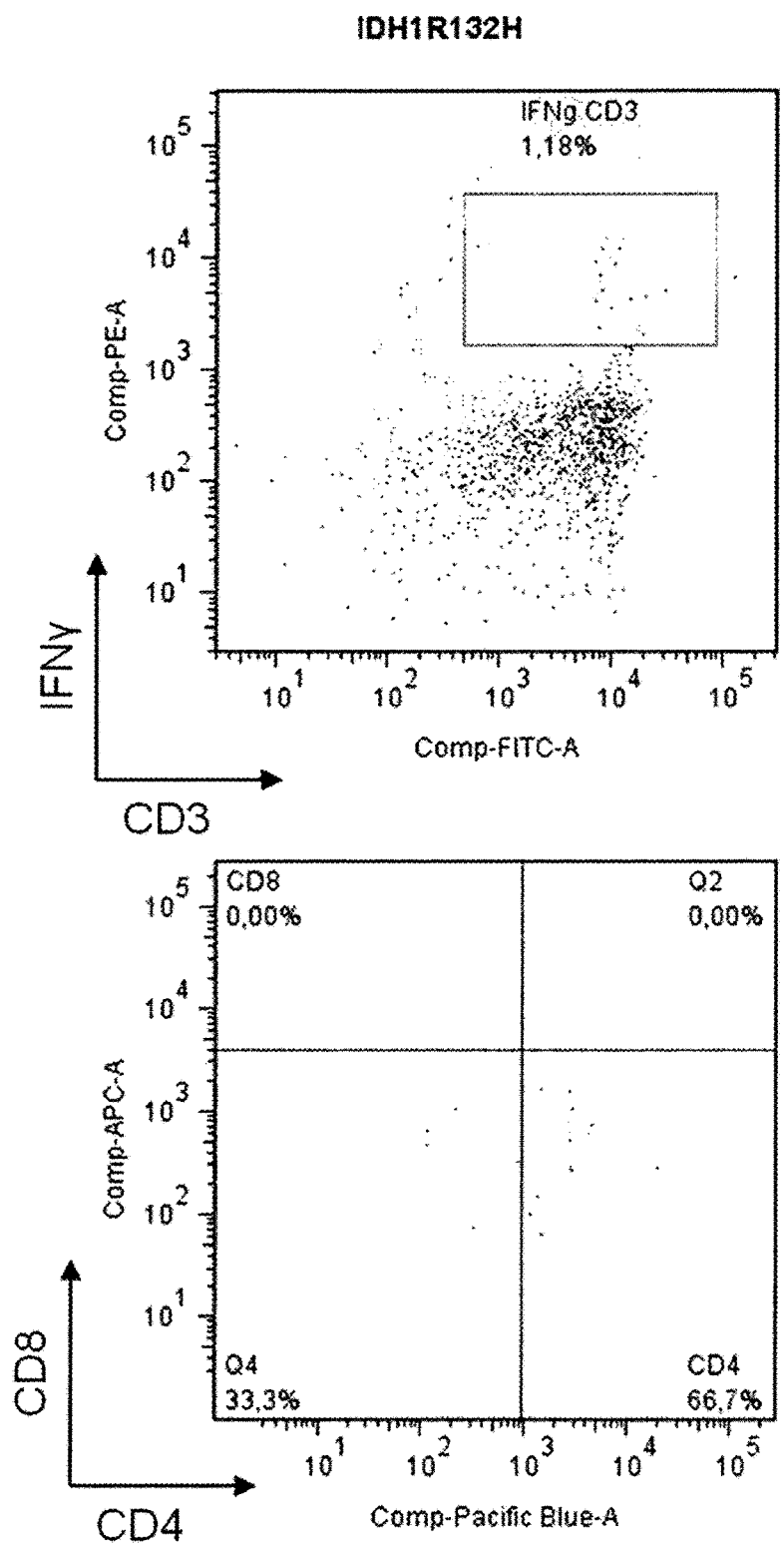
Fig. 14 C(1)

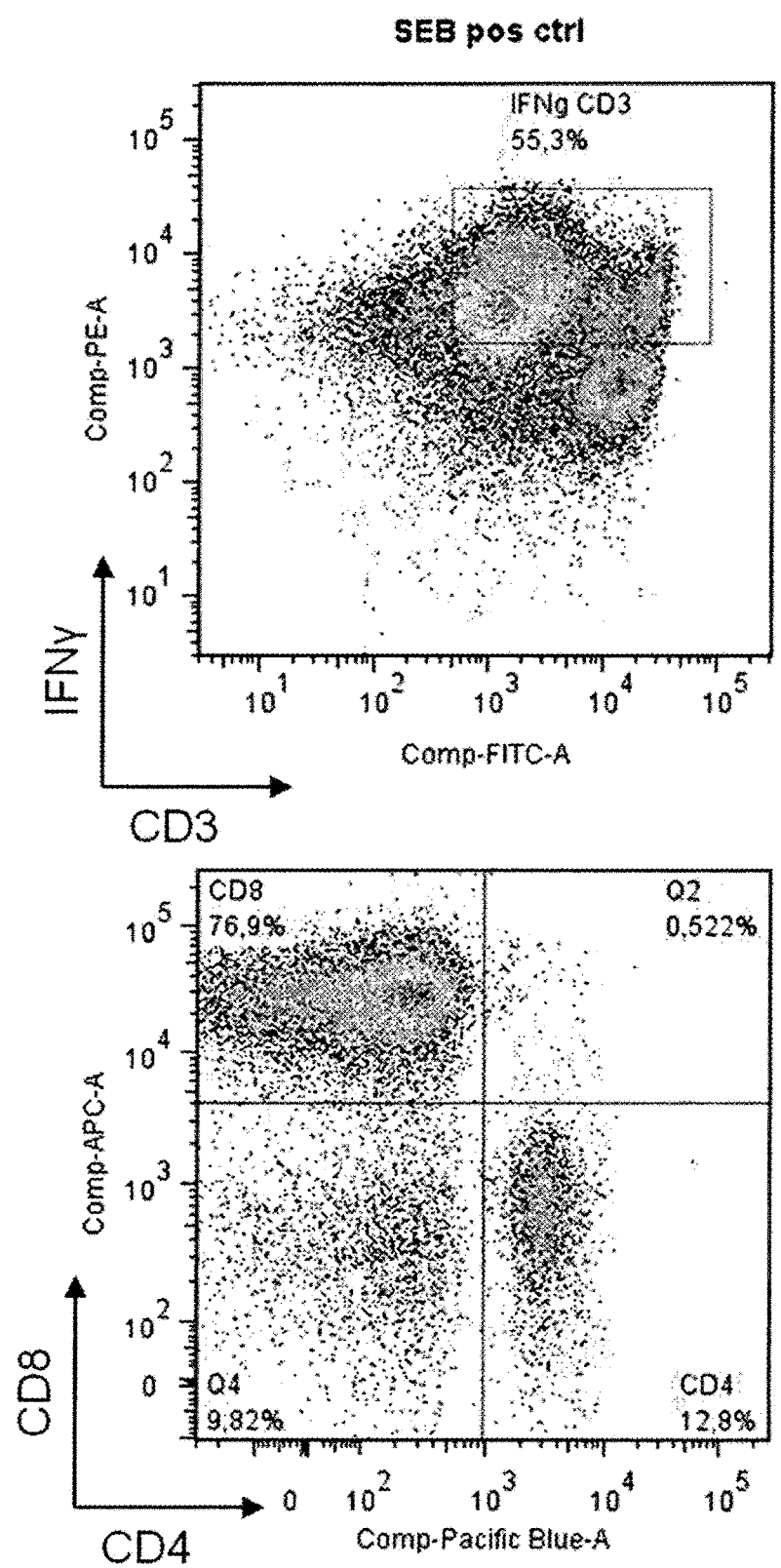
Fig. 14 C(2)

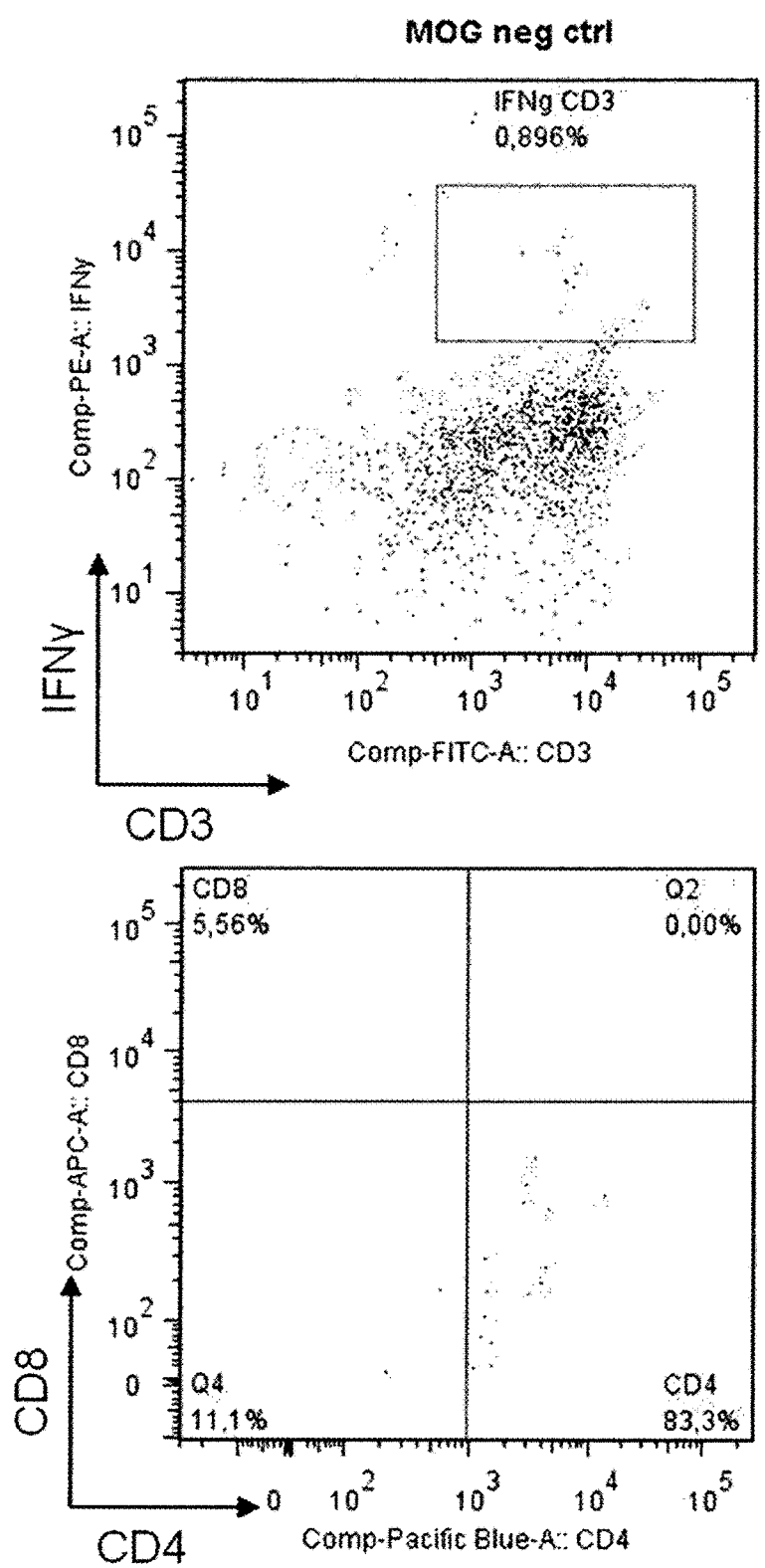
Fig. 14 C(3)

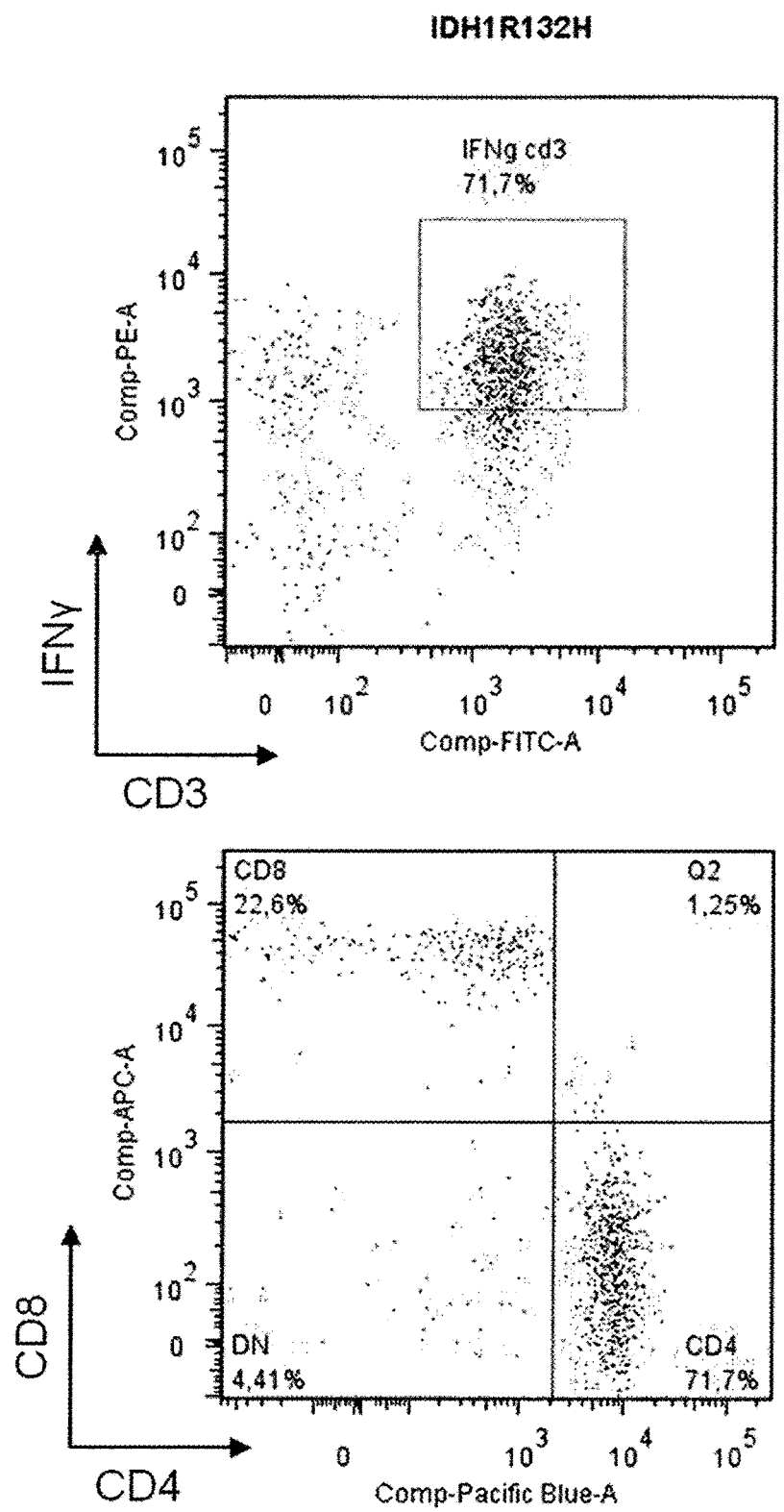
Fig. 15 A(1)

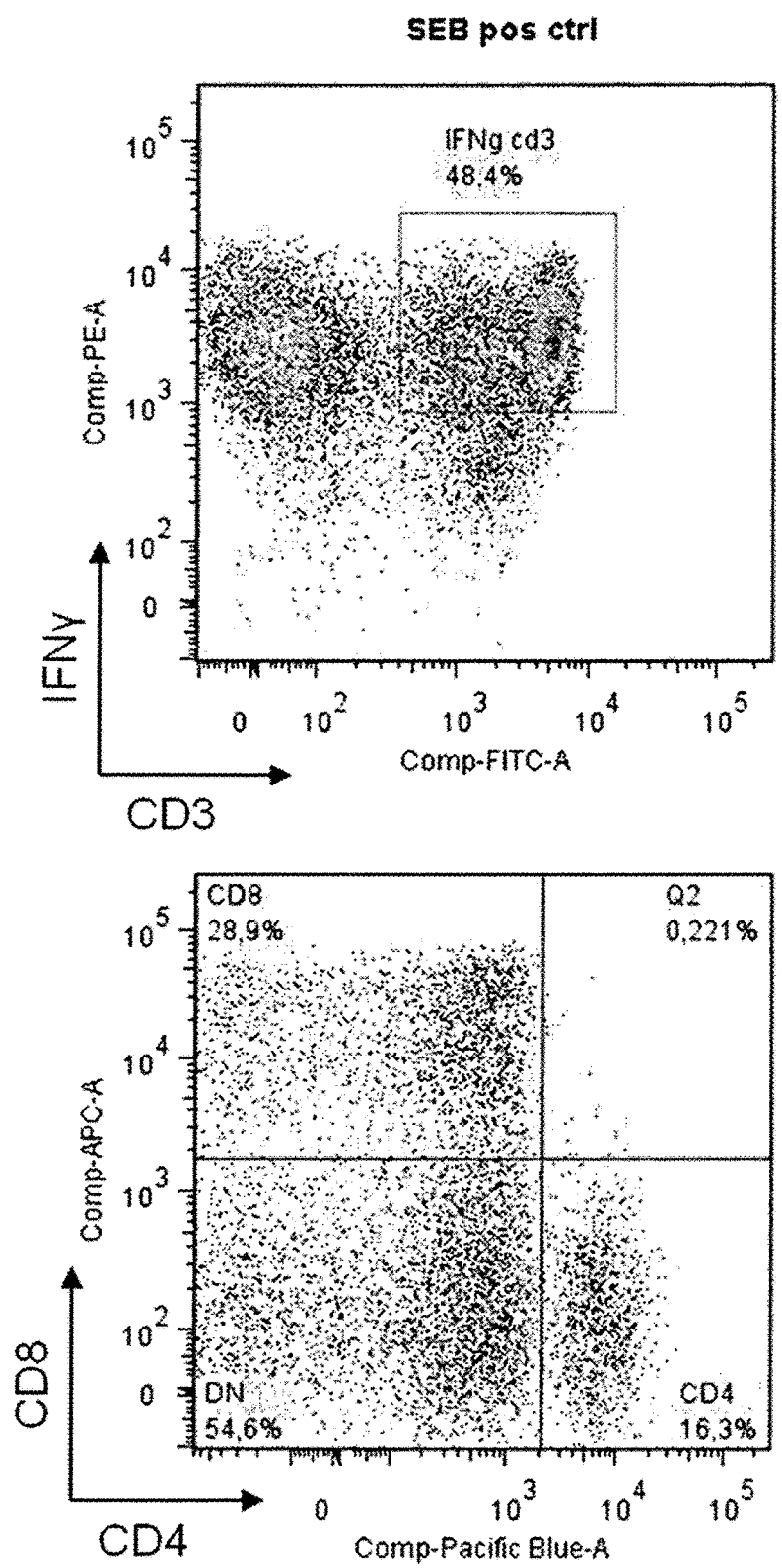
Fig. 15 A(2)

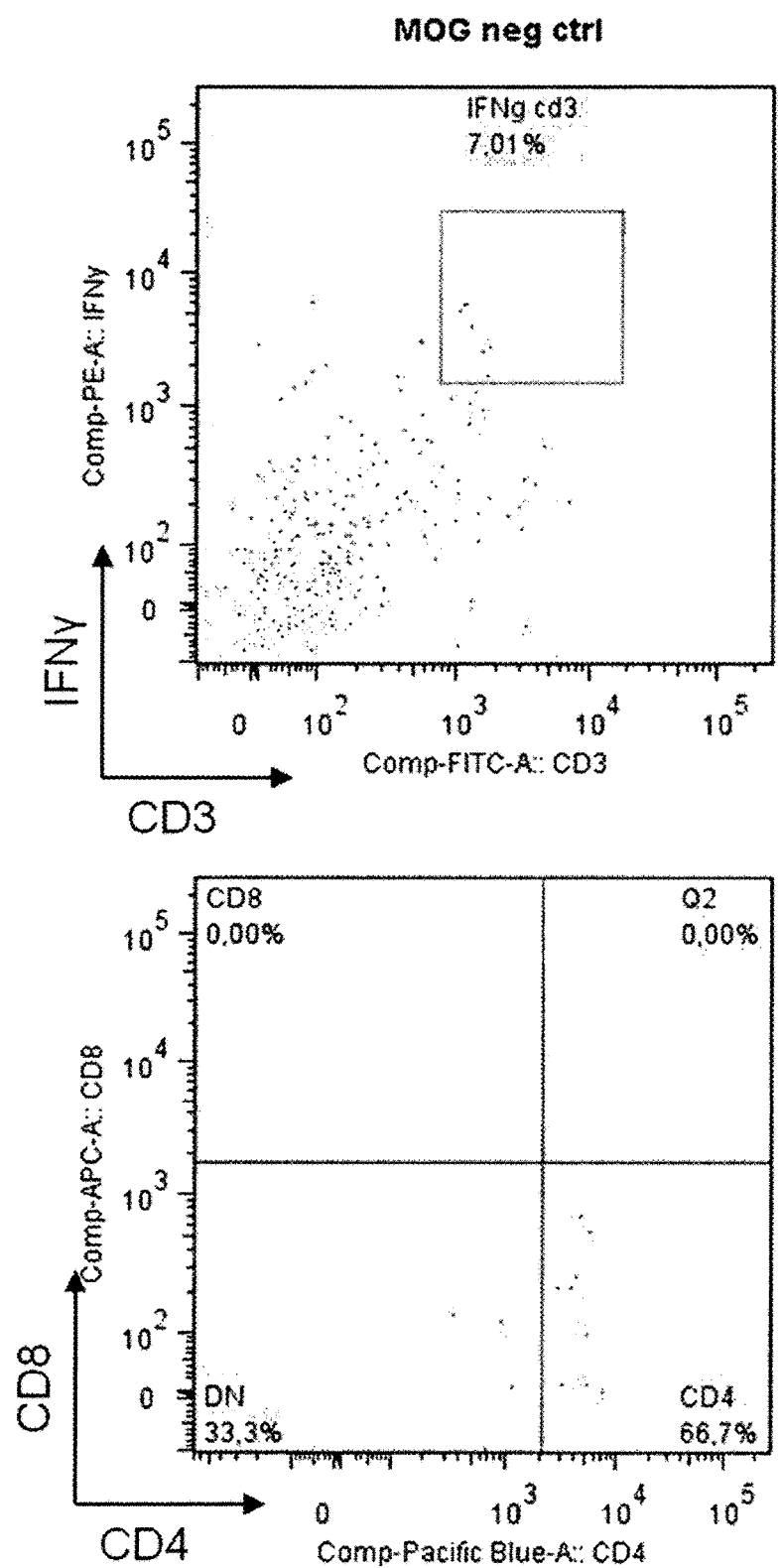
Fig. 15 A(3)

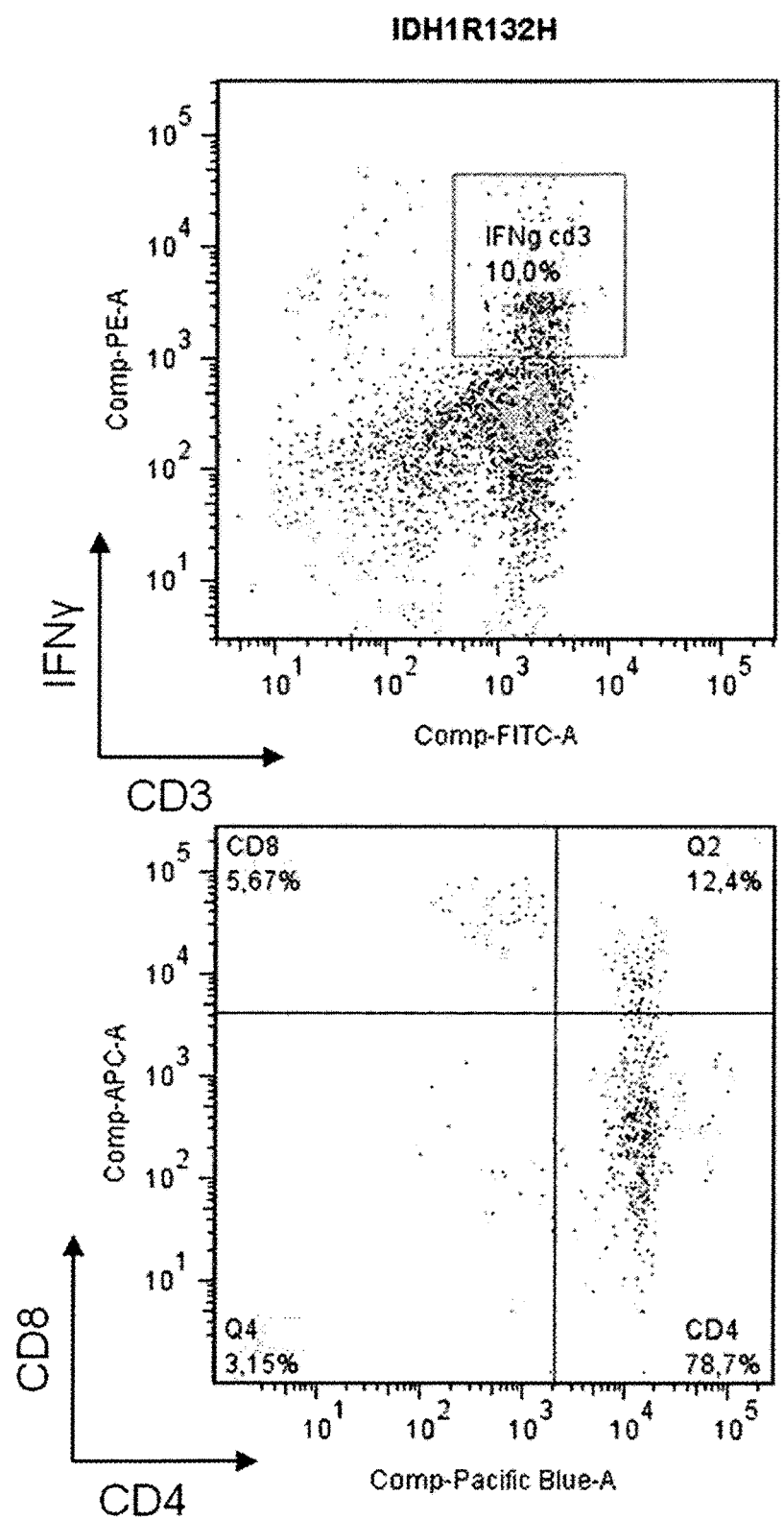
Fig. 15 B(1)

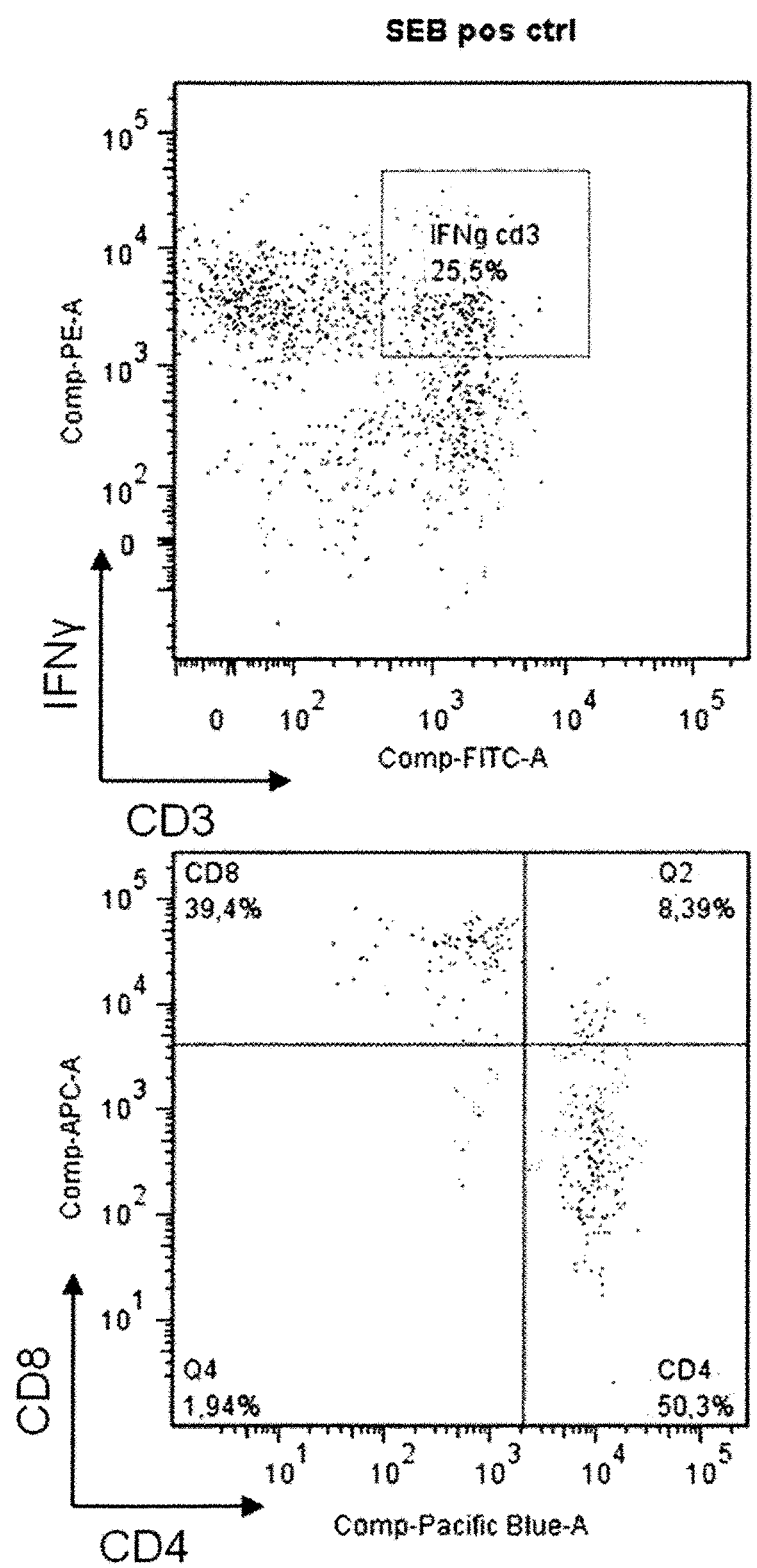
Fig. 15 B(2)

SEQUENCE LISTING

```
<160> NUMBER OF SEQ ID NOS: 19

<210> SEQ ID NO 1
<211> LENGTH: 15
<212> TYPE: PRT
<213> ORGANISM: Homo sapiens

<400> SEQUENCE: 1

Pro Arg Leu Val Ser Gly Trp Val Lys Pro Ile Ile Ile Gly His
1               5                   10                  15

<210> SEQ ID NO 2
<211> LENGTH: 15
<212> TYPE: PRT
<213> ORGANISM: Homo sapiens

<400> SEQUENCE: 2

Leu Val Ser Gly Trp Val Lys Pro Ile Ile Ile Gly His His Ala
1               5                   10                  15

<210> SEQ ID NO 3
<211> LENGTH: 15
<212> TYPE: PRT
<213> ORGANISM: Homo sapiens

<400> SEQUENCE: 3

Ser Gly Trp Val Lys Pro Ile Ile Ile Gly His His Ala Tyr Gly
```

```
<210> SEQ ID NO 4
<211> LENGTH: 15
<212> TYPE: PRT
<213> ORGANISM: Homo sapiens

<400> SEQUENCE: 4

Trp Val Lys Pro Ile Ile Ile Gly His His Ala Tyr Gly Asp Gln
1               5                   10                  15

<210> SEQ ID NO 5
<211> LENGTH: 15
<212> TYPE: PRT
<213> ORGANISM: Homo sapiens

<400> SEQUENCE: 5

Lys Pro Ile Ile Ile Gly His His Ala Tyr Gly Asp Gln Tyr Arg
1               5                   10                  15

<210> SEQ ID NO 6
<211> LENGTH: 15
<212> TYPE: PRT
<213> ORGANISM: Homo sapiens

<400> SEQUENCE: 6

Ile Ile Ile Gly His His Ala Tyr Gly Asp Gln Tyr Arg Ala Thr
1               5                   10                  15

<210> SEQ ID NO 7
<211> LENGTH: 15
<212> TYPE: PRT
<213> ORGANISM: Homo sapiens

<400> SEQUENCE: 7

Ile Gly His His Ala Tyr Gly Asp Gln Tyr Arg Ala Thr Asp Phe
1               5                   10                  15

<210> SEQ ID NO 8
<211> LENGTH: 15
<212> TYPE: PRT
<213> ORGANISM: Homo sapiens

<400> SEQUENCE: 8

His His Ala Tyr Gly Asp Gln Tyr Arg Ala Thr Asp Phe Val Val
1               5                   10                  15

<210> SEQ ID NO 9
<211> LENGTH: 20
<212> TYPE: PRT
<213> ORGANISM: Homo sapiens

<400> SEQUENCE: 9

Gly Trp Val Lys Pro Ile Ile Ile Gly His His Ala Tyr Gly Asp Gln
1               5                   10                  15

Tyr Arg Ala Thr
            20

<210> SEQ ID NO 10
<211> LENGTH: 10
<212> TYPE: PRT
<213> ORGANISM: Homo sapiens

<400> SEQUENCE: 10
```

```
Gly Trp Val Lys Pro Ile Ile Ile Gly His
1               5                   10

<210> SEQ ID NO 11
<211> LENGTH: 10
<212> TYPE: PRT
<213> ORGANISM: Homo sapiens

<400> SEQUENCE: 11

Trp Val Lys Pro Ile Ile Ile Gly His His
1               5                   10

<210> SEQ ID NO 12
<211> LENGTH: 10
<212> TYPE: PRT
<213> ORGANISM: Homo sapiens

<400> SEQUENCE: 12

Val Lys Pro Ile Ile Ile Gly His His Ala
1               5                   10

<210> SEQ ID NO 13
<211> LENGTH: 10
<212> TYPE: PRT
<213> ORGANISM: Homo sapiens

<400> SEQUENCE: 13

Lys Pro Ile Ile Ile Gly His His Ala Tyr
1               5                   10

<210> SEQ ID NO 14
<211> LENGTH: 10
<212> TYPE: PRT
<213> ORGANISM: Homo sapiens

<400> SEQUENCE: 14

Pro Ile Ile Ile Gly His His Ala Tyr Gly
1               5                   10

<210> SEQ ID NO 15
<211> LENGTH: 10
<212> TYPE: PRT
<213> ORGANISM: Homo sapiens

<400> SEQUENCE: 15

Ile Ile Ile Gly His His Ala Tyr Gly Asp
1               5                   10

<210> SEQ ID NO 16
<211> LENGTH: 10
<212> TYPE: PRT
<213> ORGANISM: Homo sapiens

<400> SEQUENCE: 16

Ile Ile Gly His His Ala Tyr Gly Asp Gln
1               5                   10

<210> SEQ ID NO 17
<211> LENGTH: 10
<212> TYPE: PRT
<213> ORGANISM: Homo sapiens

<400> SEQUENCE: 17

Ile Gly His His Ala Tyr Gly Asp Gln Tyr
1               5                   10
```

```
<210> SEQ ID NO 18
<211> LENGTH: 10
<212> TYPE: PRT
<213> ORGANISM: Homo sapiens

<400> SEQUENCE: 18

Gly His His Ala Tyr Gly Asp Gln Tyr Arg
1               5                   10

<210> SEQ ID NO 19
<211> LENGTH: 10
<212> TYPE: PRT
<213> ORGANISM: Homo sapiens

<400> SEQUENCE: 19

His His Ala Tyr Gly Asp Gln Tyr Arg Ala
1               5                   10
```

MEANS AND METHODS FOR TREATING OR DIAGNOSING IDH1 R132H MUTANT-POSITIVE CANCERS

CROSS REFERENCE TO RELATED APPLICATIONS

This application is a § 371 National Stage Application of PCT/EP2013/050048, filed Jan. 3, 2013, which claims priority to EP 12150298.3, filed Jan. 5, 2012.

BACKGROUND

Field of the Invention

The present invention concerns the field of tumor therapeutics and diagnostics. Specifically, it relates to a peptide comprising at least 8 amino acids in length which are present as contiguous amino acid sequence in the human Isocitratdehydrogenase Type 1 (IDH1), wherein said peptide has at least one amino acid exchange from R to H at a position corresponding to position 132, for use in preventing and/or treating a cancer. Further contemplated is a medicament comprising the said peptide. Furthermore, the invention relates to a method for diagnosing cancer characterized by having a mutation in the genome of at least some cancer cells which results in the expression of a mutant IDH1 having the R132H mutation comprising the steps of contacting a blood sample of a subject suspected to suffer from such a tumor with a peptide comprising at least 10 amino acids in length which are present as contiguous amino acid sequence in the IDH1, wherein said peptide has at least one amino acid exchange from R to H at a position corresponding to position 132 for a time and under conditions which allow for specific binding of a component of the immune system to the peptide, and determining whether, or not, binding of the said component of the immune system to the peptide occurred, wherein the cancer is diagnosed if the occurrence of binding has been determined. Provided by the invention is also a kit and a device for carrying out said method.

Description of Related Art

Mutations in the gene encoding cytosolic NADP+ dependent isocitrate dehydrogenase (IDH1) emerged as an unsuspected finding in sequence analysis of glioblastoma (GBM) (Parsons 2008, Science 321(5897):1807-12). Recent studies reported on mutations in the IDH1 gene resulting in an amino acid exchange in position 132 in about 70% of anaplastic gliomas and 12% of glioblastomas (Balls 2008, Acta Neuropathol. 116(6):597-602, Yan 2009, N Engl J Med. 360(8):765-73, Watanabe 2009, Am J Pathol. 174(4): 1149-53, De Carli 2009, N Engl J Med. 360(21):2248, Ducray 2009, N Engl J Med. 360(21):2248, Hartmann 2009, Acta Neuropathol. 118(4):469-74, Ichimura 2009, Neuro Oncol. 11(4):341-7, Sanson 2009, J Clin Oncol. 27(25): 4150-4).

Isocitrate dehydrogenase catalyzes the oxidative decarboxylation of isocitrate to alpha-ketoglutarate using reducing NADP+ to NADPH. Mutations affecting the amino acid arginine at position 132 of the amino acid sequence, which belongs to an evolutionary conserved region located to the binding site of isocitrate. The mutations reported always were heterozygous and alterations suggestive for protein inactivation, such as splice site or nonsense mutations, were not detected, thus prompting speculations on an activating nature of the mutation. However, the measurement of enzymatic activity showed an inactivating effect of the mutation (Yan 2009, N Engl J Med. 360(8):765-73). However, the role of IDH1 in cancer development and/or progression remains elusive.

IDH1 mutations occur in a high frequency in WHO grade II and III diffuse gliomas. 93% of all IDH1 mutations are characterized by an amino acid exchange R132H (Hartmann 2009, Acta Neuropathol. 118(4):469-74).

Effective therapies against the aforementioned cancer types and others, which are accompanied by IDH1 R132H would be highly desirable since these cancers are most often aggressive cancers with poor outcome prognosis.

The current diagnostic measures for the aforementioned cancer types and, in particular, the diagnostic means for determining whether a cancer is accompanied by an IDH1 R132H mutation, are pivotally based on either genomic DNA sequencing approaches or immunohistological staining methods (see, e.g., EP 2 256 214 A2). Both techniques, however, require proper tissue samples from the cancer tissue which are obtainable, only, via cumbersome and potentially dangerous biopsy. Thus, a reliable and efficient diagnostic measure for those types of cancer would also be desirable.

The technical problem underlying the present invention can be seen as the provision of therapeutic and diagnostic means and methods complying with the aforementioned needs. The technical problem is solved by the embodiments characterized in the claims and herein below.

SUMMARY

The present invention, thus, relates to a peptide comprising at least 8 amino acids in length which are present as contiguous amino acid sequence in the human Isocitratdehydrogenase Type 1 (IDH1), wherein said peptide has at least one amino acid exchange from R to H at a position corresponding to position 132, for use in preventing and/or treating cancer.

The term "peptide" as used herein refers to a small organic molecule wherein amino acids are covalently linked by peptide bonds. In contrast to polypeptides (proteins), peptides merely consist of from 2 to about 100 amino acids. Peptides are due to their small size usually bio-available molecules, i.e. they can enter into most tissues of an organism and may even enter into the cells. The peptide according to the present invention comprises at least 8 amino acids in length. Thus, the peptide may consist essentially from at least 8 to about 100 amino acids, preferably, from at least 8 to about 50 amino acids, from at least 8 to about 40 amino acids, from at least 8 to about 35 amino acids, from at least 8 to about 30 amino acids, from at least 8 to about 25 amino acids, from at least 8 to about 20 amino acids, from at least 8 to about 15 amino acids or from at least 8 to about 10 amino acids in length. The term "about" as used in this context refers to a number of amino acids, which diverges from the precise number by +/− one, i.e. one amino acid in addition or one amino acid less. Preferably, the precise number is intended.

The term "Isocitratdehydrogenase Type 1" or "IDH1" as used herein refers to an enzyme which is physiologically involved in the citric acid cycle in that it catalyzes the oxidative decarboxylation of isocitrate whereby alpha-ketoglutarate and $CO_2$ are produced. The reaction requires the conversion of NAD+ to NADH. Another isoform of the enzyme which is preferred according to the invention catalyzes the same reaction in the cytosol as well as in mitochondria or and peroxisomes using NADP+ as a cofactor rather than NAD+. IDH1 as referred to herein, preferably, is human IDH1 having an amino acid sequence as disclosed in Kim et al. (Kim 1995, Biochem J 308(Pt1): 63-68) or as available under NCBI/Genbank accession numbers CAG46496.1, GI: 49456351; CAG38738.1, GI:49168486; CAG38553.1, GI: 49065470; or AAH12846.1, GI: 15277488. The term, however, also encompasses variants of said human IDH1 characterized by the aforementioned specific amino acid sequence. Such variants may be orthologs, paralogs or homologs, in general. A variant as referred to herein, preferably, has an amino acid sequence which differs from the specific amino acid sequence referred to above by at least one amino acid substitution, addition and/or deletion. Preferably, such a variant amino acid sequence is at least 70%, at least 80%, at least 85%, at least 90%, at least 95%, at least 97%, at least 98%, or at least 99% identical over its entire length with the aforementioned specific amino acid sequence. Preferably, the degree of identity can be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Preferably, the variant has the enzymatic activities referred to above and essentially the same immunological properties as the human IDH1 referred to above.

DETAILED DESCRIPTION OF A PREFERRED EMBODIMENT

The peptide of the invention shall comprise at least one amino acid exchange from R to H at a position corresponding to position 132. Preferably, the peptide may comprise in the at least 8 amino acids which are present as contiguous amino acid sequence in the human IDH1 as the sole amino acid exchange an exchange of R to H at a position corresponding to position 132 of the human IDH1 as specified elsewhere herein. However, the peptide may comprise further exchanges, preferably one or two additional exchanges or even more.

Preferably, at least 8 of the amino acids of the peptide of the invention are present as contiguous amino acid sequence in the human IDH1. Accordingly, the peptide of the present invention can either essentially consist of an amino acid sequence derived from human IDH1 or it may consist of an amino acid sequence comprising a stretch of 8 or more amino acids derived from human IDH1 and other stretch of amino acids which are not present in human IDH1.

Preferably, the peptide of the invention consists of between 8 and 40 amino acids in length the peptide consists of between 8 to 35 amino acids, between 8 to 30 amino acids, between 8 to 25 amino acids, between 8 to 20 amino acids, between 8 to 15 amino acids or between 8 to about 10 amino acids in length which are present as contiguous amino acid sequence in the human IDH1.

The precise number of amino acids for the peptide in general as well as the number of amino acids derived from the human IDH1 amino acid sequence can be determined by the skilled person depending on the envisaged use. In this context, the skilled person is well aware of the fact that an immune response may be optimized by varying either the total length of the peptide or the length of the stretch of contiguous amino acids from the IDH1 target.

Preferably, the peptide of the present invention comprises or essentially consists of an amino acid sequence selected from the group consisting of:

a) an amino acid sequence consisting of the amino acids corresponding to amino acids 118 to 132 (SEQ ID NO: 1);

b) an amino acid sequence consisting of the amino acids corresponding to amino acids 120 to 134 (SEQ ID NO: 2);

c) an amino acid sequence consisting of the amino acids corresponding to amino acids 122 to 136 (SEQ ID NO: 3);

d) an amino acid sequence consisting of the amino acids corresponding to amino acids 124 to 138 (SEQ ID NO: 4);

e) an amino acid sequence consisting of the amino acids corresponding to amino acids 126 to 140 (SEQ ID NO: 5);

f) an amino acid sequence consisting of the amino acids corresponding to amino acids 128 to 142 (SEQ ID NO: 6);

g) an amino acid sequence consisting of the amino acids corresponding to amino acids 130 to 144 (SEQ ID NO: 7);

h) an amino acid sequence consisting of the amino acids corresponding to amino acids 132 to 146 (SEQ ID NO: 8); and i) an amino acid sequence consisting of the amino acids corresponding to amino acids 123 to 142 (SEQ ID NO: 9).

The term "cancer" as used herein refers to any malignant neoplasm resulting from the undesired growth, the invasion, and under certain conditions metastasis of impaired cells in an organism. The cells giving rise to cancer are genetically impaired and have usually lost their ability to control cell division, cell migration behavior, differentiation status and/or cell death machinery. Most cancers form a tumor but some hematopoietic cancers, such as leukemia, do not. Preferably, said cancer is a cancer characterized by having a mutation in the genome of at least some cancer cells which results in the expression of a mutant IDH1 having the R132H mutation. Whether a cancer has a mutation in at least some of the cancer cells as specified before can be determined by the skilled artisan by PCR-based and/or sequencing based detection techniques. Moreover, the methods of the invention referred to elsewhere herein may be applied as well.

More preferably, said cancer is a tumor and, preferably, is a glioma. Gliomas have been reported to frequently comprise cells or even consist of cells comprising the aforementioned IDH1 mutation. Most preferably, the said glioma is WHO II or WHO III astrocytoma, oligodendroglioma, oligoastrocytoma, glioblastoma, or gliosarcoma.

Moreover, preferably, cancer as referred to herein is, also preferably, an acute myeloid leukemia, myelodysplastic syndrome, or dysembryoplastic neuroepithelial tumor. The symptoms accompanying the aforementioned cancer types are well known in the art and can be determined by the skilled artisan without further ado. Details of the cancer types may be found in standard text books of medicine, e.g., Pschyrembl or Stedman.

The term "preventing" as used herein refers to the prevention of the development of a disease as referred to herein. Such a prevention is preferably achieved for a certain time window upon administration of the peptide of the invention. Preferably, the said time window is at least 1 year, at least 2 years, at least 5 years, at 10 years or up to the entire remaining life-span of the subject that received the preventive treatment referred to before. It will be understood that a preventive treatment as referred to herein will, in all likelihood, not be successful in all subjects, which received the treatment. However, it is envisaged that the preventive treatment is effective in at least a statistically significant portion of the subjects that are treated. Whether a statistically significant portion, e.g., of a cohort of subjects, can be successfully prevented may, preferably, be determined by statistical tests discussed elsewhere herein in more detail.

The term "treating" as used herein refers to ameliorating and/or curing a disease as referred to herein, preventing progression of the disease or at least an amelioration of at least one symptom associated with the said disease. It will be understood that a treatment as referred to herein will, in all likelihood, not be successful in all subjects, which received the treatment. However, it is envisaged that the treatment is effective in at least a statistically significant portion of the subjects that are treated. Whether a statistically significant portion, e.g., of a cohort of subjects, can be successfully treated may, preferably, be determined by statistical tests discussed elsewhere herein in more detail.

The peptide according to the present invention shall be provided for use in treating and/or preventing cancer, i.e. it shall be manufactured as a medicament, e.g., comprised in a pharmaceutical composition. Details on such a medicament or pharmaceutical composition are to be found elsewhere herein. The peptide to be used according to the present invention can also be applied in a method for treating and/or preventing cancer. Accordingly, the invention also contemplates a method for treating and/or preventing cancer in a subject suffering therefrom comprising administering to said subject a therapeutically effective amount of the peptide as defined herein.

Advantageously, it has been found in the studies underlying the present invention that the peptide of the present invention can be used to elicit an immune response towards the IDH1 R132H mutant specifically. Accordingly, the cancer cells that express the mutated IDH1 will be attacked by the cellular and humoral responses of the immune system resulting in a effective way of specifically treating and/or preventing the cancer types referred to herein which are known to be associated with the aforementioned IDH1 mutation. Thanks to the findings underlying the present invention, an effective medicament for the treatment of the cancer types is provided as well as a cancer vaccine.

The explanations and comments made herein above apply mutatis mutandis for the embodiments of the invention described in the following.

The present invention relates to a medicament comprising the peptide of the invention and, preferably, a pharmaceutically acceptable carrier.

The term "medicament" as used herein refers, in one aspect, to a pharmaceutical composition containing the peptide referred to above as pharmaceutical active compound, wherein the pharmaceutical composition may be used for human or non-human therapy of various diseases or disorders in a therapeutically effective dose. The peptide, preferably, can be present in liquid or lyophilized form. The medicament is, preferably, for topical or systemic administration. Conventionally a medicament will be administered intra-muscular or, subcutaneous. However, depending on the nature and the mode of action of a compound, the medicament may be administered by other routes as well. The peptide is the active ingredient of the composition, and is, preferably, administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

A carrier must be acceptable in the sense of being compatible with the other ingredients of the formulation and being not deleterious to the recipient thereof. The pharmaceutical carrier employed may include a solid, a gel, or a liquid. Examples for solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

A diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the peptide to be used in medicament of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. The medicament referred to herein is administered at least once in order to treat or ameliorate or prevent a disease or condition recited in this specification. However, the said medicament may be administered more than one time. Specific medicaments are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The medicament according to the present invention may also comprise drugs in addition to the antagonist of the present invention, which are added to the medicament during its formulation.

Finally, it is to be understood that the formulation of a medicament takes place under GMP standardized conditions or the like in order to ensure quality, pharmaceutical security, and effectiveness of the medicament.

The present invention also relates to a method for diagnosing cancer characterized by having a mutation in the genome of at least some cancer cells which results in the expression of a mutant IDH1 having the R132H mutation comprising the steps of:
a) contacting a blood sample of a subject suspected to suffer from such cancer with a peptide comprising at least 10 amino acids in length which are present as contiguous amino acid sequence in the IDH1, wherein said peptide has at least one amino acid exchange from R to H at a position corresponding to position 132 for a time and under conditions which allow for specific binding of a component of the immune system to the peptide; and
b) determining whether, or not, binding of the said component of the immune system to the peptide occurred, wherein the cancer is diagnosed if the occurrence of binding has been determined The method of the present invention is to be carried out on an isolated sample of a subject, i.e. is an ex vivo method. Moreover, the method may be assisted by automation either entirely or at least in parts. For example, the steps a) and b) may be carried out by a device as specified elsewhere herein. Moreover, the actual steps of diagnosing can be established by a suitable computer program which based on the occurrence of binding indicates the diagnosis of cancer in a suitable output format.

The term "diagnosing" as used herein means assessing whether a subject suffers from cancer, or not. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention. Diagnosing according to the present invention includes applications of the method in monitoring, confirmation, and sub-classification of the relevant cancer.

Moreover, diagnosing also includes establishing a prognosis for a subject. A subject which is diagnosed to suffer from cancer according to the method of the present invention shall have cancer cells expressing the IDH1 R132H polypeptide. The presence of the said mutant IDH1 is a predictive indicator for a possibly poor outcome in the subjects. Thus, the method of the present invention can also be applied for risk stratification approaches and, thus, for determining the amount of intensive care and hospitalization which will be required for an individual subject suffering from cancer.

The term "blood sample" as used herein refers to a sample of whole blood or any fraction thereof. Fractions of whole blood may be fractions comprising cells such as leucocytes or fractions which are essentially cell-free, such as plasma or serum.

The term "component of the immune system" as used herein refers to cellular and non-cellular components of the immune system.

Non-cellular components according to the present invention encompass those which are capable of specifically binding to an antigenic peptide. Thus, preferably, said component of the immune system is an antibody comprised in the blood sample. An antibody referred to in this context is, preferably, an antibody that occurs in blood of a subject and that specifically binds to the peptides of IDH1 referred to herein in accordance with the method of the present invention. Antibodies which may occur in blood of a subject are, preferably, antibodies of the IgG or IgM isotype.

If a non-cellular component of the immune system is to be determined in accordance with the method of the present invention, said peptide to be applied in the method, preferably, consists of between 10 and 20 amino acids in length which are present as contiguous amino acid sequence in the human IDH1 and comprises an amino acid sequence selected from the group consisting of:
a) an amino acid sequence consisting of the amino acids corresponding to amino acids 118 to 132 (SEQ ID NO: 1);
b) an amino acid sequence consisting of the amino acids corresponding to amino acids 120 to 134 (SEQ ID NO: 2);
c) an amino acid sequence consisting of the amino acids corresponding to amino acids 122 to 136 (SEQ ID NO: 3);
d) an amino acid sequence consisting of the amino acids corresponding to amino acids 124 to 138 (SEQ ID NO: 4);
e) an amino acid sequence consisting of the amino acids corresponding to amino acids 126 to 140 (SEQ ID NO: 5);
f) an amino acid sequence consisting of the amino acids corresponding to amino acids 128 to 142 (SEQ ID NO: 6);
g) an amino acid sequence consisting of the amino acids corresponding to amino acids 130 to 144 (SEQ ID NO: 7); and
h) an amino acid sequence consisting of the amino acids corresponding to amino acids 132 to 146 (SEQ ID NO: 8).

The cellular component referred to in accordance with the present invention as a component of the immune system is a immune system cell which is capable of specifically binding to a peptide antigen Immune system cells capable of binding specifically to a peptide antigen are, preferably, T-lymphocytes, B-lymphocytes, or dendritic cells. More preferably, the component of the immune system is a lymphocyte and, most preferably, a CD4-positive T-lymphocyte, a CD8-positive T-lymphocyte, or a B-lymphocyte comprised in the blood sample.

If a cellular component of the immune system is to be determined in accordance with the method of the present invention, said peptide to be applied in the method, preferably, consists of between 10 and 20 amino acids in length which are present as contiguous amino acid sequence in the human IDH1 and comprises an amino acid sequence selected from the group consisting of:

a) an amino acid sequence consisting of the amino acids corresponding to amino acids 118 to 132 (SEQ ID NO: 1);

b) an amino acid sequence consisting of the amino acids corresponding to amino acids 120 to 134 (SEQ ID NO: 2);

c) an amino acid sequence consisting of the amino acids corresponding to amino acids 122 to 136 (SEQ ID NO: 3);

d) an amino acid sequence consisting of the amino acids corresponding to amino acids 124 to 138 (SEQ ID NO: 4);

e) an amino acid sequence consisting of the amino acids corresponding to amino acids 126 to 140 (SEQ ID NO: 5);

f) an amino acid sequence consisting of the amino acids corresponding to amino acids 128 to 142 (SEQ ID NO: 6);

g) an amino acid sequence consisting of the amino acids corresponding to amino acids 130 to 144 (SEQ ID NO: 7);

h) an amino acid sequence consisting of the amino acids corresponding to amino acids 132 to 146 (SEQ ID NO: 8);

i) an amino acid sequence consisting of the amino acids corresponding to amino acids 123 to 132 (SEQ ID NO: 10);

j) an amino acid sequence consisting of the amino acids corresponding to amino acids 124 to 133 (SEQ ID NO: 11);

k) an amino acid sequence consisting of the amino acids corresponding to amino acids 125 to 134 (SEQ ID NO: 12);

l) an amino acid sequence consisting of the amino acids corresponding to amino acids 126 to 135 (SEQ ID NO: 13);

m) an amino acid sequence consisting of the amino acids corresponding to amino acids 127 to 136 (SEQ ID NO: 14);

n) an amino acid sequence consisting of the amino acids corresponding to amino acids 128 to 137 (SEQ ID NO: 15)

o) an amino acid sequence consisting; of the amino acids corresponding to amino acids 129 to 138 (SEQ ID NO: 16);

p) an amino acid sequence consisting of the amino acids corresponding to amino acids 130 to 139 (SEQ ID NO: 17);

q) an amino acid sequence consisting of the amino acids corresponding to amino acids 131 to 140 (SEQ ID NO: 18); and r) an amino acid sequence consisting of the amino acids corresponding to amino acids 132 to 141 (SEQ ID NO: 19).

The term "subject" as used herein relates to animals, preferably mammals, and, more preferably, humans. Preferably, the method of the present invention will be applied for subjects suspected to either suffer from any of the aforementioned cancer types in light of clinically apparent symptoms or subjects suspected to suffer from said cancer due to a potential increased predisposition.

Suitable peptides comprising at least 10 amino acids in length which are present as contiguous amino acid sequence in the IDH1, wherein said peptides having at least one amino acid exchange from R to H at a position corresponding to position 132 are specified elsewhere herein. Specifically preferred peptides are detailed above.

Contacting the sample as referred to herein refers to bringing the peptide and the sample into physical contact thereby allowing specific binding of a component of the immune system comprised in the sample, or not, to the peptide. It will be understood that contacting as meant herein is carried out for a time and under conditions sufficient for allowing the component to bind specifically to the peptide. Depending on the nature of the sample, pre-treatment steps might be necessary so that the component has access and can specifically bind to the peptide. Moreover, dependent on the kind of sample, the handling might be different. For example, if the component of the immune system is a non-cellular component as specified elsewhere herein, serum or plasma may be obtained first from a whole blood sample. If the component is a cellular component, concentration and/or separation of appropriate cells may be required. Preferably, the peptide to be contacted with the blood sample is immobilized on a solid support. Preferably, this immobilization allows for carrying out washing steps which remove the blood sample after contacting in order to improve sensitivity and/or specificity of the detection and in order to remove background noise. Furthermore, such a contacting step may be carried out in an automated manner, preferably, in an analyzing unit of a device of the invention as specified elsewhere herein. However, also preferably, the components of the immune system present in a blood sample may be immobilized and contacted with, e.g., a solution comprising the peptide.

It will be understood that upon contacting, it needs to be determined whether, or not, binding of the said component of the immune system to the peptide occurred. Determining binding of the component to the peptide as used herein can be achieved by suitable detection methods allowing for the detection of whether a complex of the component and the peptide has formed or the component is, e.g., after washing, present in immobilized form on a solid support due to binding to the peptide. In the first case, a detection agent for the complex of the component of the immune system and the peptide can be used. In the second case, any detection agent for the component of the immune system may be used. If the component of the immune system is immobilized first and contacted afterwards with the peptide, either a detection method allowing for the detection of whether a complex of the component and the peptide has formed can be used or the peptide itself may be coupled to a detectable label.

Detection agents that may be used in the method of the present invention for either detecting a complex of the component and the peptide or for the component include antibodies, aptameres, or any other molecules, which allow for specific binding. The detection agent is, preferably, coupled to a detectable marker such as a radioactive isotope (e.g., radioactive isotopes of Iodide Technetium), fluorescent or chemoluminescent agents (e.g., FITC, rhodamin), an enzyme, which is capable of generating a detectable signal by converting a substrate (e.g., horseradish peroxidase, firefly luciferase, or beta galactosidase), a fluorescent protein (e.g., green-, blue- or red-fluorescent protein). Suitable detectable markers are well known in the art. Moreover, the detection agent may be a composite agent wherein a first agent is that specifically binds to the component or the complex is capable of attracting one or more further agents coupled to a detectable label. Such an agent may be biotin. In such a case an avidin- or streptavidin coupled agent can be used which upon binding of the biotin bound to the component or complex will serve as a detectable marker. Suitable detectable markers in such a case are those referred to above, more preferably, an enzyme shall be used as a detectable marker in such a case. Furthermore, an detection antibody may be used detecting the complex or component. Such a detection antibody shall be coupled to a detectable marker as describe above. Thus, in the latter case, the detection antibody will upon binding to the component or complex generate a detectable signal. The principle of detection by antibodies is well known in the art and routinely applied. The aforementioned detection agents may be applied mutatis mutandis for the detection of the peptide, which is applied and specifically bound to immobilized components of the immune system.

Dependent on the type of detectable marker, different detection methods can be applied using a reader system for the signal generated by the detectable marker. Such systems include automatic signal reader device, such as an ELISA or RIA reader, for manual or automatic detection of the detectable signal. Moreover, the reader system may determine additional information of the sample, e.g., an automated signal reader may determine further biomarkers comprised by the sample in addition.

The diagnosis is established or at least an aid for diagnosis can be gathered from the method of the invention if the specific binding of the peptide and the component of the immune system has been determined Advantageously, it has been shown in the studies underlying the present invention that the IDH1 R132H mutant if present in cancer cells elicits an immune response resulting in humoral immune response as well as cellular immune response. Accordingly, antibodies as well as cellular components of the immune system specifically directed against the IDH1 R132H mutant and, in particular, peptide epitopes comprising said mutation are found in the blood of patients suffering from IDH1 R132H positive cancer, such as glioma. Based on these findings, the method of the present invention allow for the blood-based diagnosis of certain types of malignant cancer such as glioma, and preferably, WHO II or WHO III astrocytoma, oligodendroglioma, oligoastrocytoma, glioblastoma, gliosarcoma, or acute myeloid leukemia, myelodysplastic syndrome, or dysembryoplastic neuroepithelial tumors. Moreover, the method of the invention allows for classifying the cancer as IDH1 R132H-positive cancer and, thus, as a particular malignant stage or class of cancers having an inferior prognosis. Since the method uses blood as a sample material, cumbersome and expensive biopsies which are currently used for the diagnosis of, e.g., the gliomas referred to above can be avoided. The method also allows for inclusion into clinical routine screening approaches.

In a preferred embodiment of the method of the present invention, said method further comprises the step of recommending an anti-cancer therapy based on the diagnosis obtained in step b).

The term "recommending" as used herein refers to making a recommendation for an anti-cancer therapy or excluding (i.e. not recommending) a certain anti cancer therapy for a subject. Such a recommendation shall serve optionally together with other information, e.g., information from histopathological investigations, as a basis for a clinician to apply a certain anti-cancer therapy for an individual subject, or not. Based on the diagnosis established in step b) of the method of the present invention, i.e. the diagnosis of "cancer" or "no cancer", a recommendation for an anti-cancer therapy will be made. It will be understood that only in cases where the diagnosis of "cancer" has been established by the method of the present invention, the recommendation for the anti-cancer therapy shall be made. In cases where "no cancer" is established as diagnosis based on the method of the present invention, the recommendation would be to refrain from an anti-cancer therapy. As set forth above, further information from the subject from which the sample originates can be used as well for improving the recommendation. In an aspect, a combined anti-cancer therapy, e.g., with different anti tumor drugs, can be recommended if the method of the present invention identifies cancer cells but if further cancer cells which are not identified by the method of the present invention are detected in the investigated cancer, e.g., by histopathological analyses.

The term "anti-cancer therapy" as used herein encompasses therapies, which are surgery-based therapies, radiation-based therapies, drug-based therapies or combinations thereof. The said drug-based anti-cancer therapy is, preferably, temozolomide or nitrosourea-based therapies.

The present invention, furthermore, relates to a device for diagnosing cancer characterized by having a mutation in the genome of at least some cancer cells which results in the expression of a mutant IDH1 having the R132H mutation, said device comprising:
  a) an analyzing unit comprising a peptide comprising at least 8 amino acids in length which are present as contiguous amino acid sequence in the IDH1, wherein said peptide has at least one amino acid exchange from R to H at a position corresponding to position 132 arranged for detection of a component of the immune system in a sample of a subject; and
  b) an evaluation unit comprising a detector capable of detecting specific binding of the component of the immune system to the said peptide, wherein said detector generates an output signal indicating whether specific binding occurred, or not.

The term "device" as used herein relates to a system comprising at least the aforementioned analyzing unit and the evaluation unit operatively linked to each other. How to link the units of the device in an operating manner will depend on the type of units included into the device. For example, where units for automatic analysis of a sample are applied, the data obtained by said automatically operating analyzing unit can be processed by, e.g., a computer program in order to obtain the desired results by the evaluation unit. Preferably, the units are comprised by a single device in such a case. The analyzing unit may comprise the peptide in immobilized form on a solid support. Such an analyzing unit is particular useful for liquid samples. The sample to be investigated with the device of the present invention is preferably a blood sample as specified elsewhere herein. The peptide is preferably comprised in immobilized form on a detection zone in the analyzing unit such that a solution such as a blood sample can be applied. Moreover, the analyzing unit may comprise internal or external vials for washing or detection solutions which may need to be applied to the detection zone after contacting the peptides with the sample in order to allow for proper detection of the component of the immune system component to the immobilized peptides. The analyzing unit also shall comprise a detector capable of measuring whether binding of a component of the immune system occurred to the immobilized peptides in the detection zone. suitable detectors can be included by the skilled artisan dependent on the kind of detection reaction used for measuring the binding of the immune system component to the immobilized peptides. The evaluation unit, preferably, is a computer or data processing device which comprises implemented rules, i.e. an algorithm, for evaluating the binding determined by the analyzing unit whereby the binding is evaluated into significant or non-significant binding based on the signal type, strength. For samples, which are evaluated to show non-significant binding the diagnosis "no cancer" will be established and, preferably, indicated in a suitable output format. If significant binding is obtained as result of the evaluation, the diagnosis cancer shall be established and, preferably, indicated in a suitable output format.

Finally, the present invention relates to a kit for diagnosing cancer characterized by having a mutation in the genome of at least some cancer cells which results in the expression of a mutant IDH1 having the R132H mutation, said kit comprising instructions for carrying out the said method and a peptide comprising at least 10 amino acids in length which are present as contiguous amino acid sequence in the IDH1, wherein said peptide has at least one amino acid exchange from R to H at a position corresponding to position 132.

The term "kit" as used herein refers to a collection of the aforementioned antibody and instructions provided in a ready-to-use manner for diagnosing cancer in a sample. The peptide and the instructions are, preferably, provided in a single container. Preferably, the kit also comprises further components, which are necessary for carrying out the diagnosis. Such components may be auxiliary agents, which are required for the detection of the peptide binding, agents for pre-treating the sample to be analyzed or calibration standards.

All references cited in this specification are herewith incorporated by reference with respect to their entire disclosure content and the disclosure content specifically mentioned in this specification.

FIGURES

FIG. 1: Natural MHC class II-restricted immune response to IDH1R132H in a patient with an IDH1R132H-mutated glioma. Elispot-Assay (left) from peripheral blood stimulated with wildtype (wt) or mutated IDH1 peptide. A peptide mix and phytohemagglutinin (PHA) served as controls. Flow cytometry (right) analyzing CD4 and CD8 cell surface expression on T cells expanded after stimulation with IDH1R132H peptide.

Figure 2:
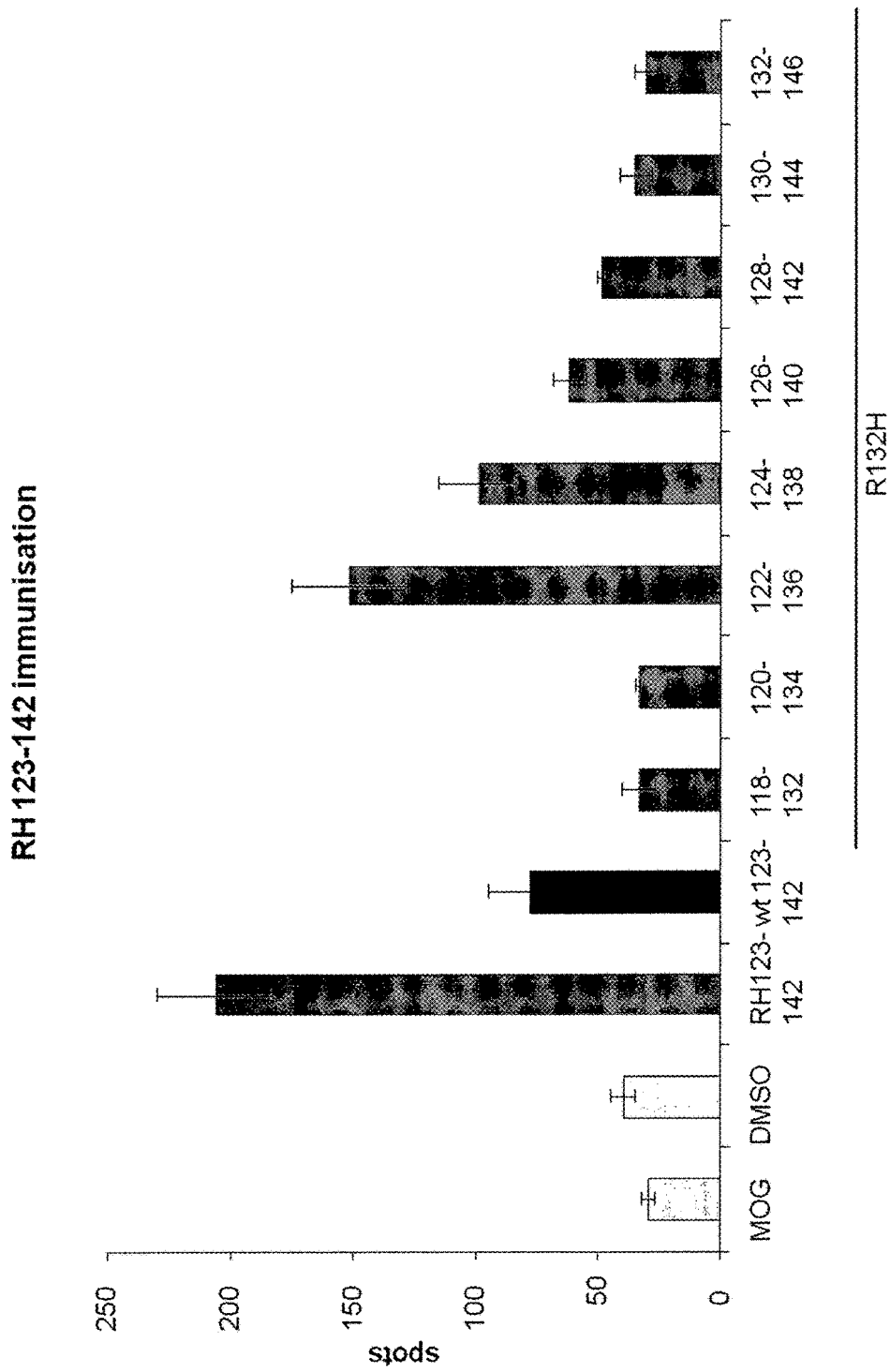
Figure 2:
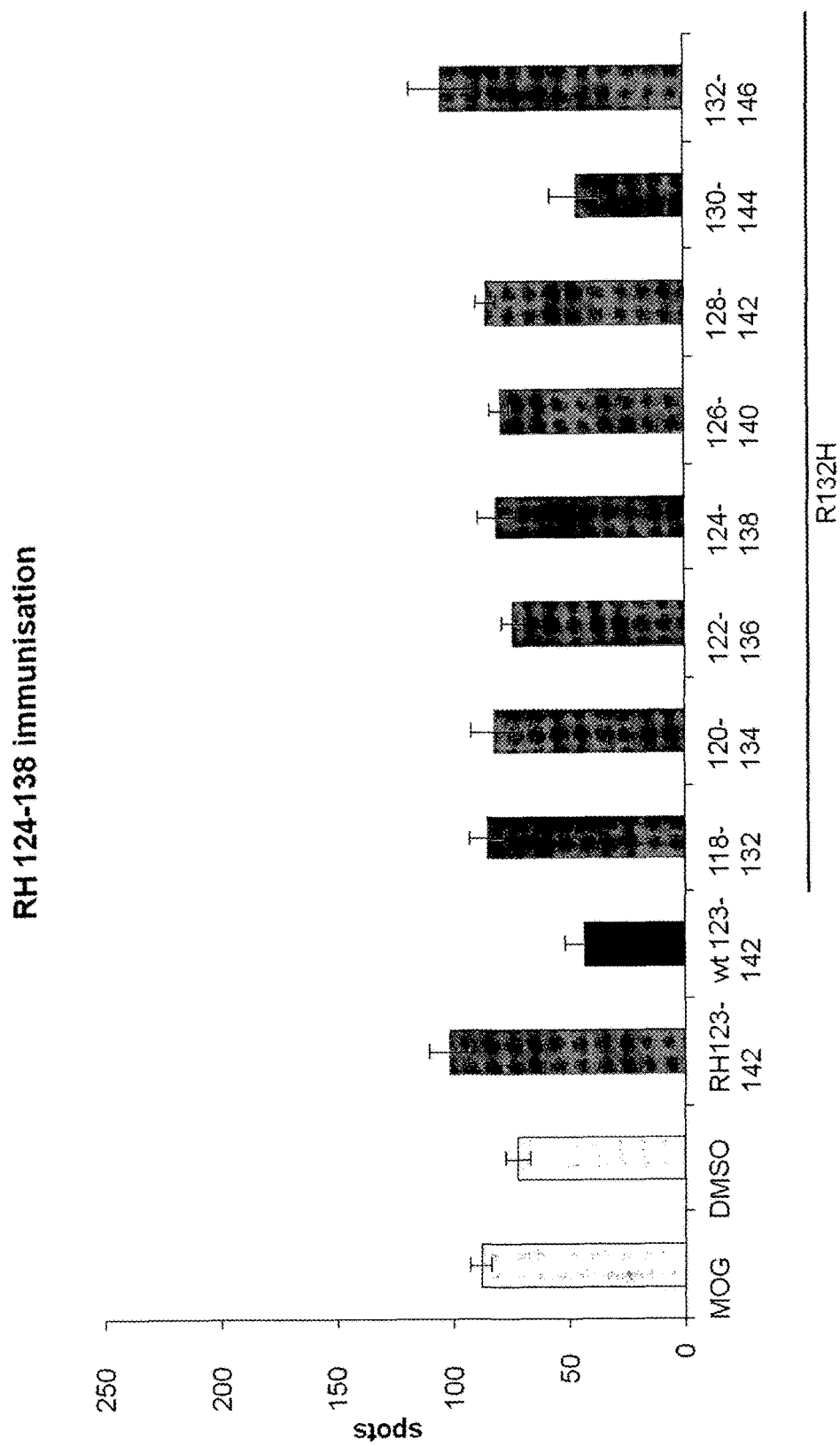
Figure 2:
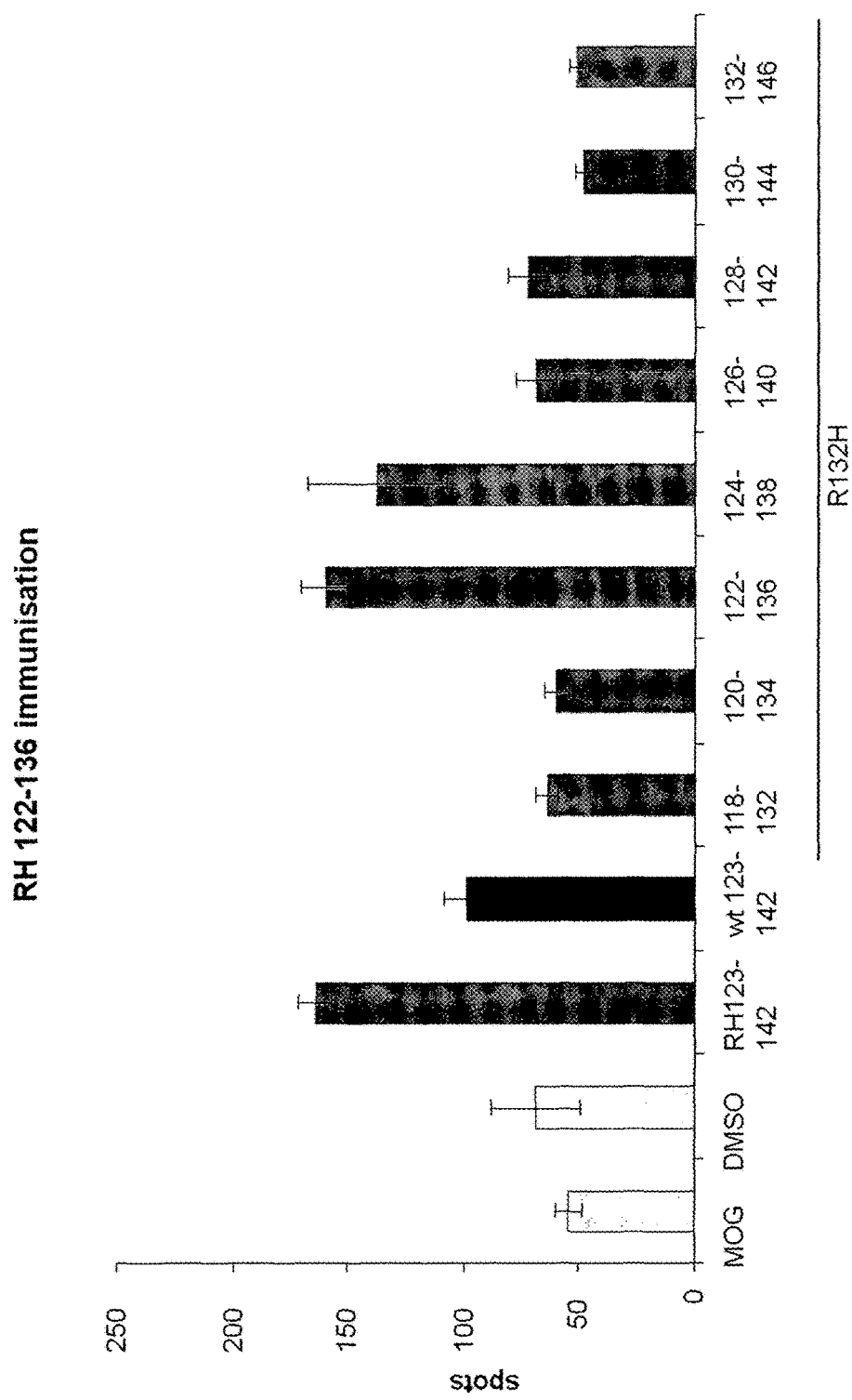
Figure 2:
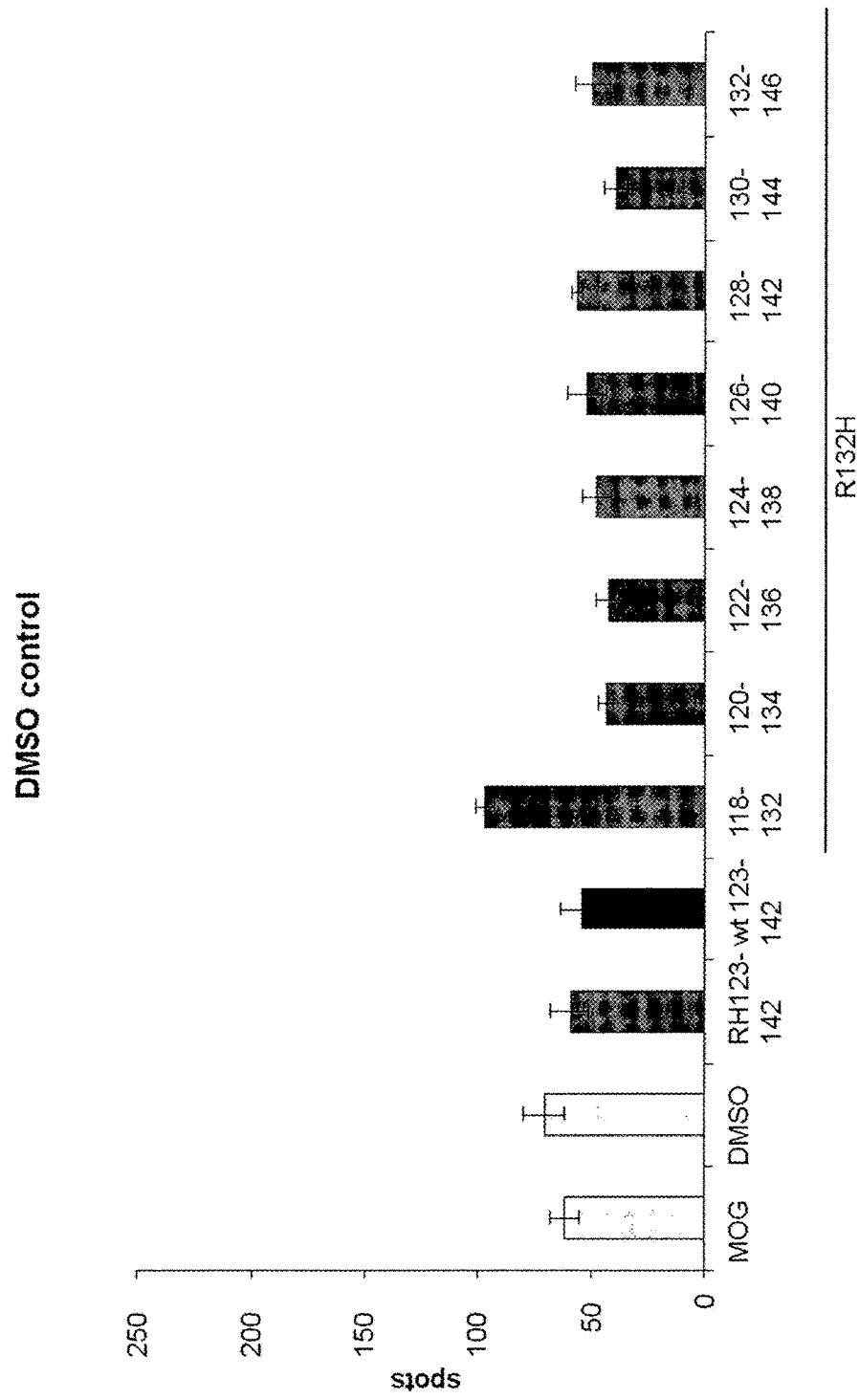

FIG. 2: MHC class II-restricted immunogenic IDH1R132H epitopes in MHC class II humanized mice. Peripheral immune response in transgenic mice devoid of mouse MHC class I and II but transgenic for human A2 and DR1 after immunization with IDH1R132H peptides 123-142 (panel 1), 124-138 (panel 2), 122-136 (panel 3) or sham immunized (panel 4) and restimulation ex vivo with the indicated IDH1R132H peptide sequences. Wildtype IDH1 peptide 123-142, DMSO and an MHC class II-restricted immunogenic myelin peptide (MOG) served as controls.

Figure 3:
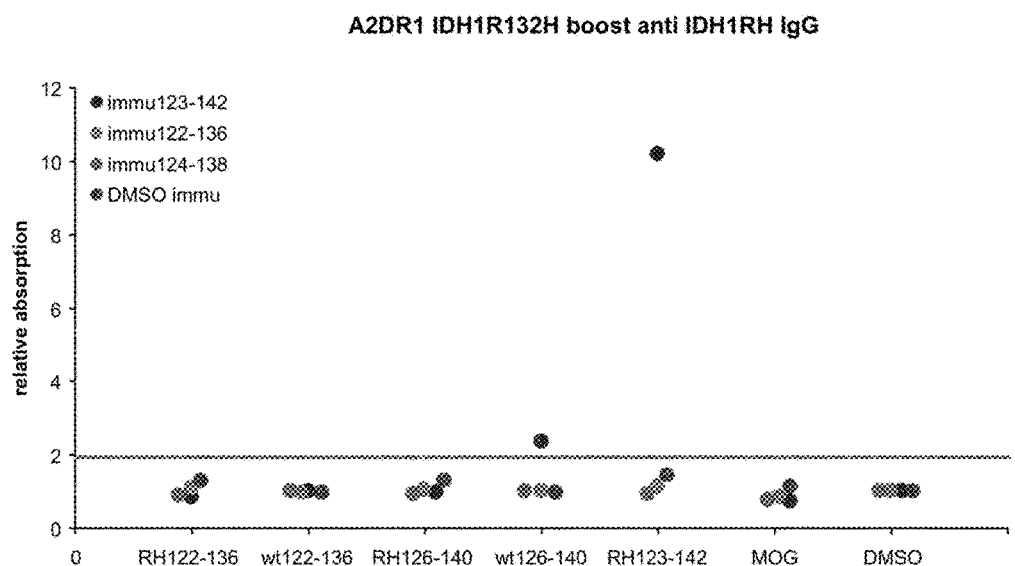

FIG. 3: IDH1R132H-specific antibody response in MHC class II humanized mice. IDH1R132H-specific IgG antibody response in the serum of transgenic mice devoid of mouse MHC class I and II but transgenic for human A2 and DR1 after immunization with IDH1R132H peptides 123-142 (dark blue), 124-138 (green), 122-136 (light blue) or sham immunized (red) and binding to the indicated IDH1R132H peptide sequences. Wildtype IDH1 peptides 122-136 and 126-140, DMSO and an MHC class II-restricted immunogenic myelin peptide (MOG) served as controls.

FIG. 4: Natural IDH1R132H-specific antibody response in patients with IDH1R132H-mutated gliomas. Natural IDH1R132H-specific IgG antibody response to the IDH1R132H 126-140 peptide in the serum of patients with IDH1-mutated gliomas, IDH1 wildtype gliomas (wt), gliomas with unknown IDH1 status or healthy controls. Information on MHC class II haplotype and tumor type is indicated where available.

Figure 5:
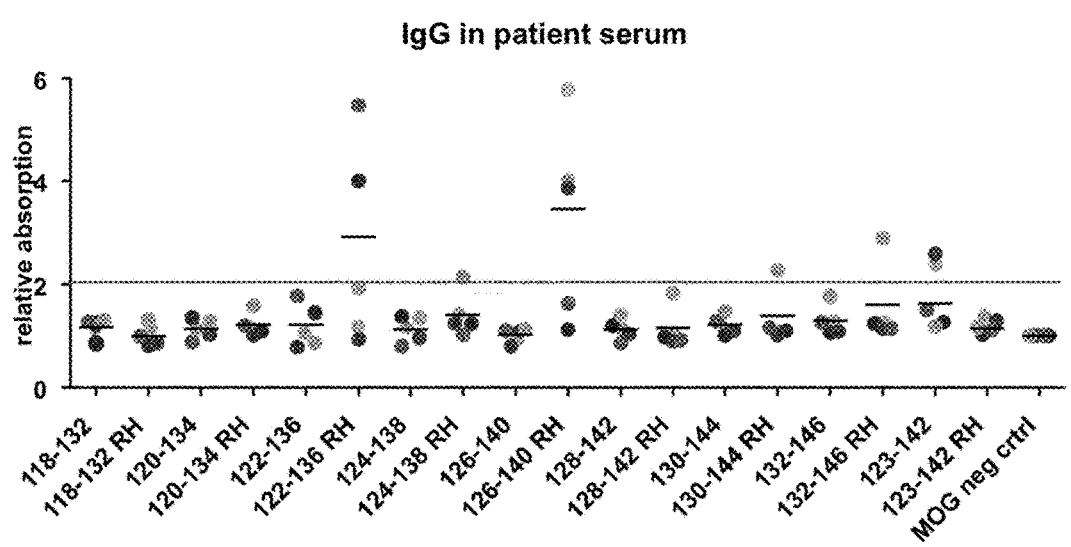
Figure 6A:
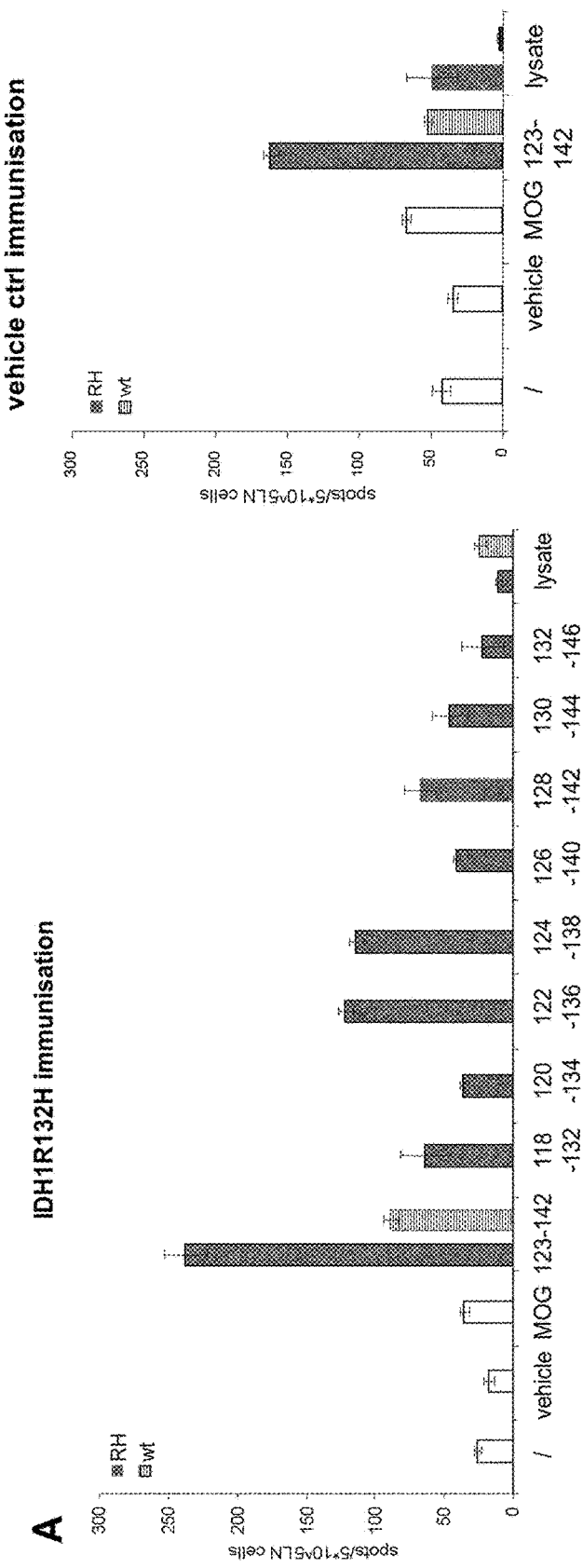
Figure 6B:
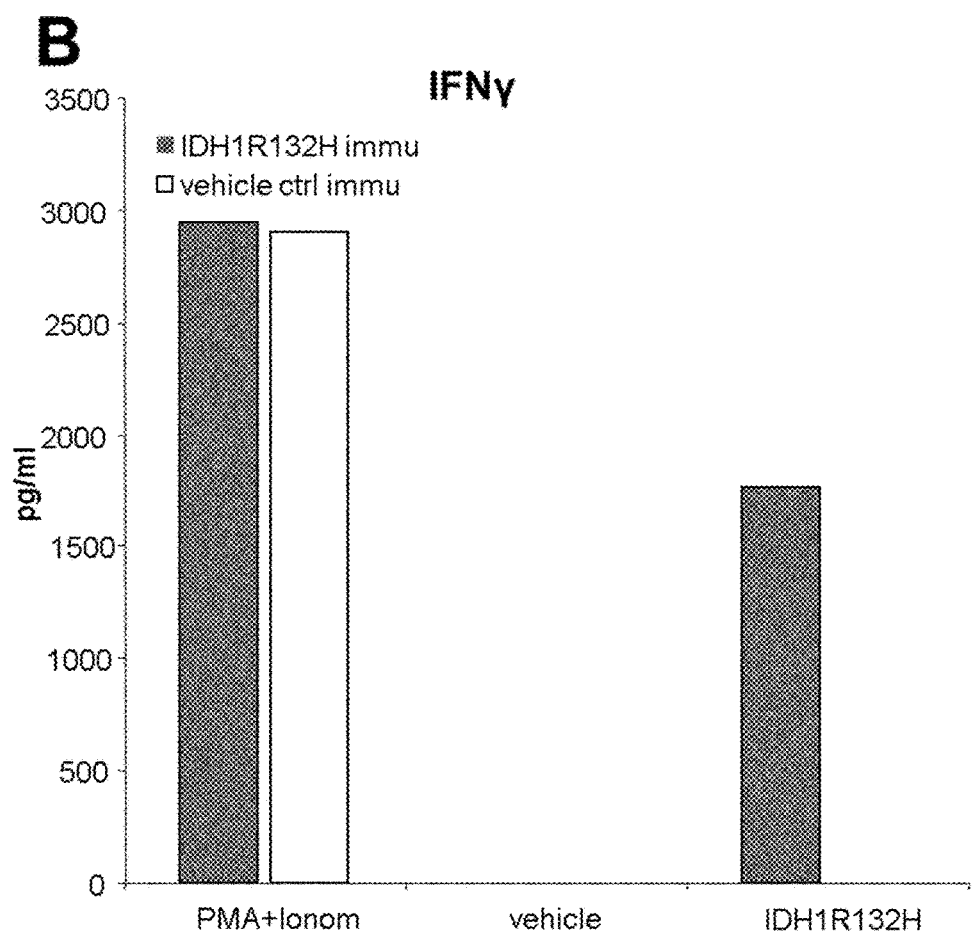
Figure 6C:
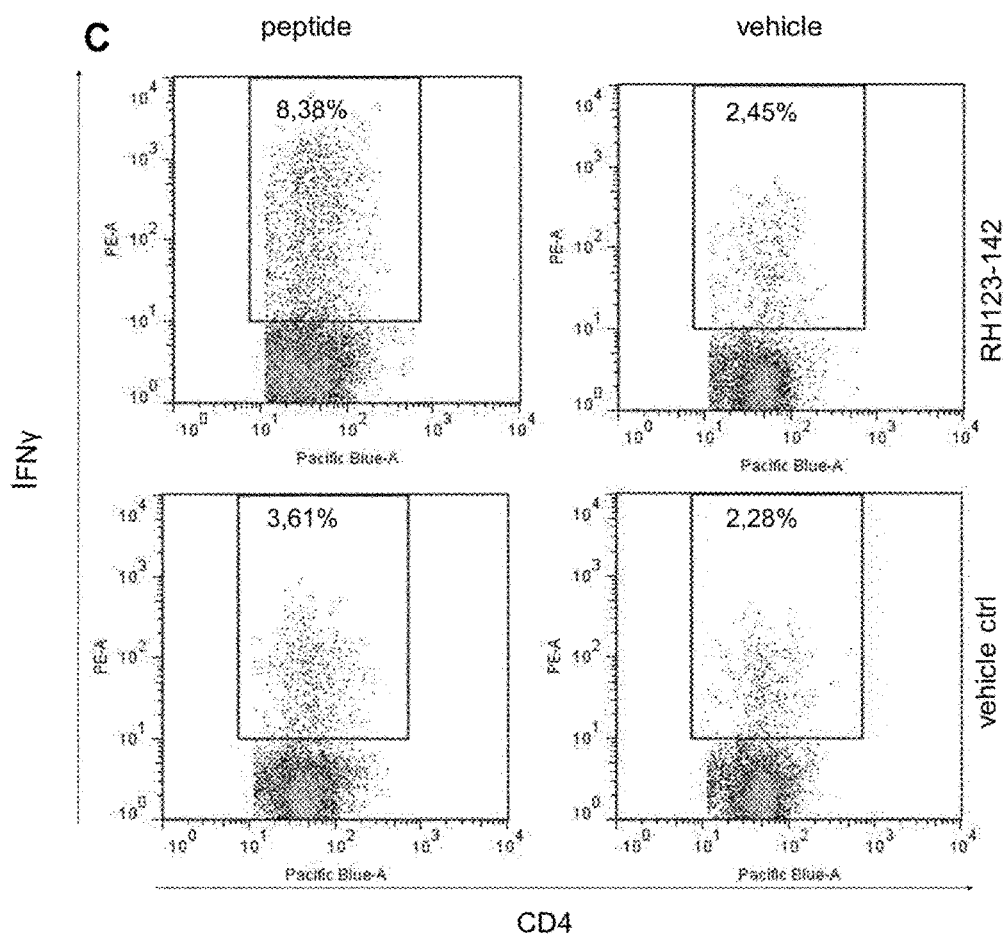
Figure 6C:
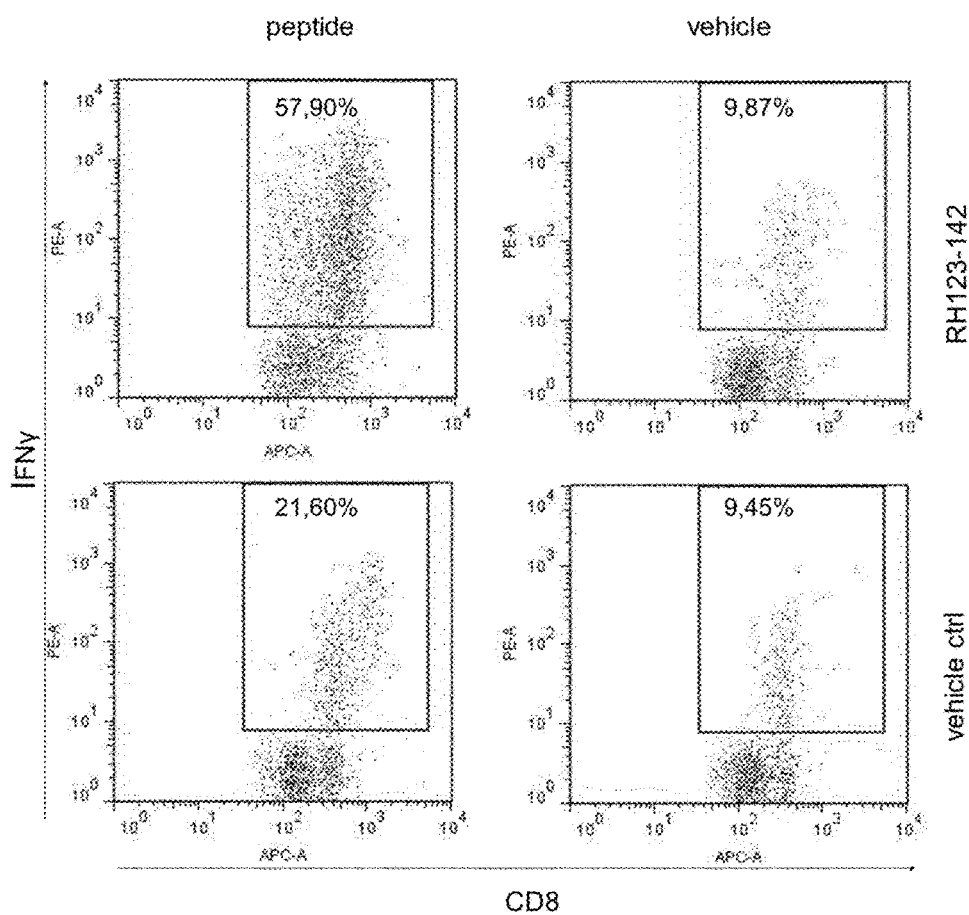

FIG. 5: Epitope specificity of the natural IDH1R132H-specific antibody response in patients with IDH1R132H-mutated gliomas. Natural IDH1R132H-specific IgG antibody response to the indicated wildtype (wt) or IDH1R132H (RH) peptides in the serum of 5 IDH1R132H patients (color coded) with IDH1-mutated gliomas.

FIG. 6: IDH1R132H peptide vaccination induces Th1 and CTL responses A2.DR1 mice were immunized with 100 µg IDH1R132H$_{123-142}$ peptide in Montanide ISA51, 300 ng GM-CSF and 50 µl Aldara Cream (5% Imiquimod) and boosted after 14 days without GM-CSF. Control mice were treated in the same manner without peptide. After an additional 14 days, spleens and lymphnodes were excised for analysis. A) Lymph node cells were stimulated with 10 µg/ml IDH1R132H, IDH1wt peptides, negative control peptide (MOG), with vehicle only or with 200 µg/ml protein lysate of IFNg-treated, IDH1wt or IDH1R132H overexpressing GL261 cells for 38 h. IFNγ production was measured by ELISpot. Left, IDH1R132H vaccination; right, vehicle control vaccination. B) Systemic IFNγ T cell response was confirmed in splenocytes which were stimulated as in (A) and with 20 ng/ml PMA and 1 µg/ml ionomycin as positive control for 72 h. Supernatants were harvested and IFNγ was colorimetrically quantified in triplicates in an anti-IFNγ-coated ELISA using a standard curve with biotinylated anti-IFNγ, streptavidin-HRP and TMB. C) IFNγ-producing splenocytes were analysed via cytokine flow cytometry. Splenocytes were stimulated ex vivo with IDH1R132H$_{123-142}$ or vehicle control, restimulated with 20 ng/ml PMA and 1 µg/ml Ionomycin for 5 h including Golgi transport inhibitor 5 µg/ml Brefeldin A for secretion inhibition. Surface markers CD3, CD4, and CD8 were stained, and for intracellular staining, cells were permeabilized and fixed and IFNγ was stained. Cells were analysed in a flow cytometer. Upper panels, IDH1R132H vaccinated mouse; lower panels, vehicle control vaccinated mouse. Representative results of one mouse are shown.

Figure 7A:
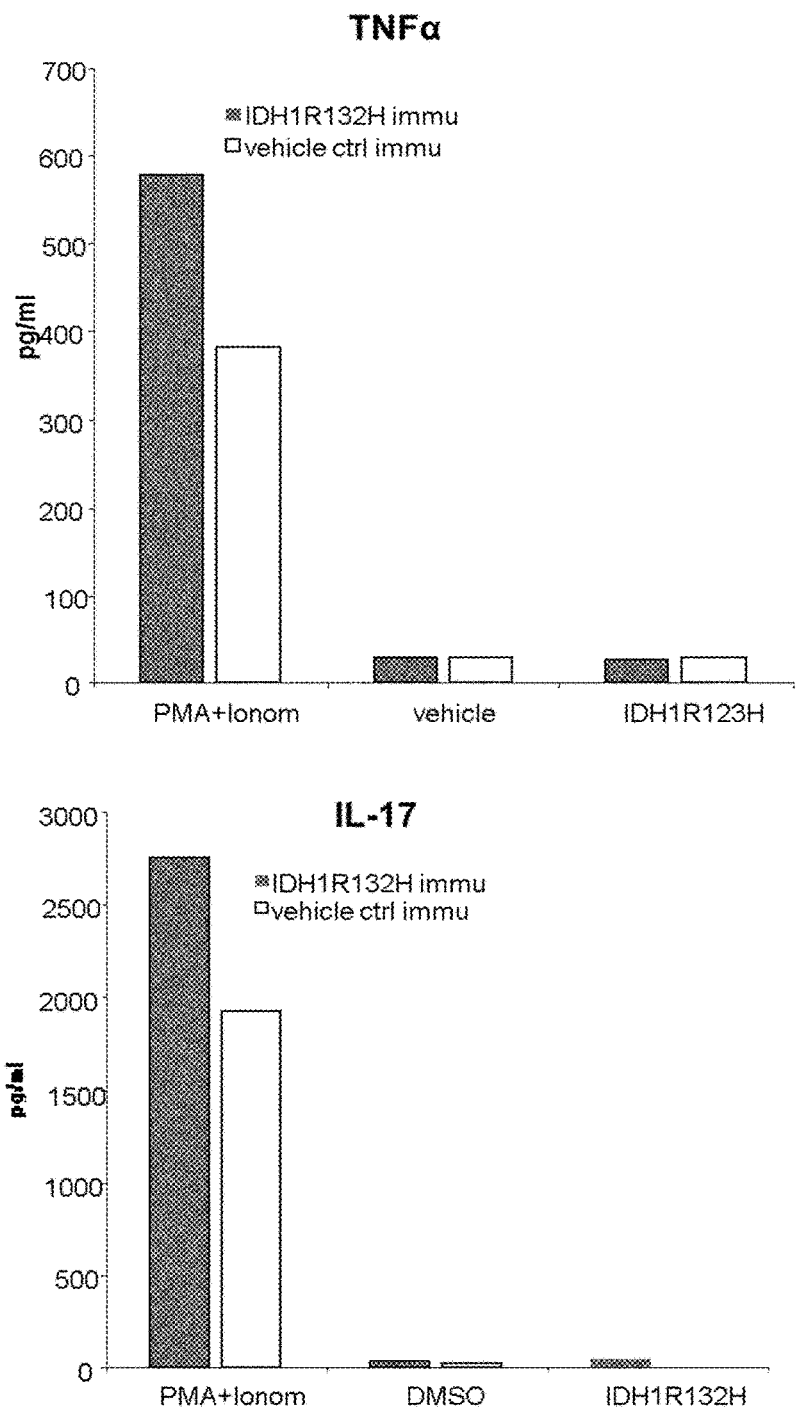
Figure 7B:
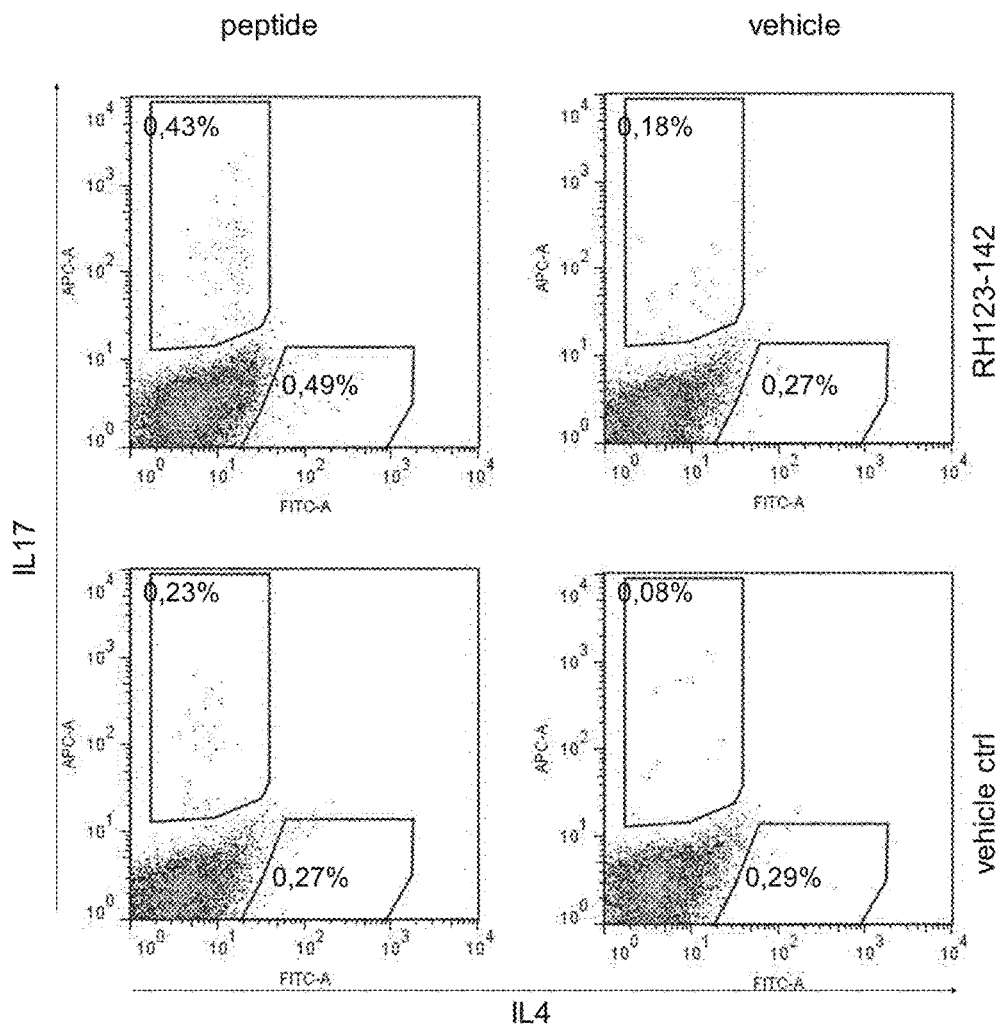
Figure 7B:
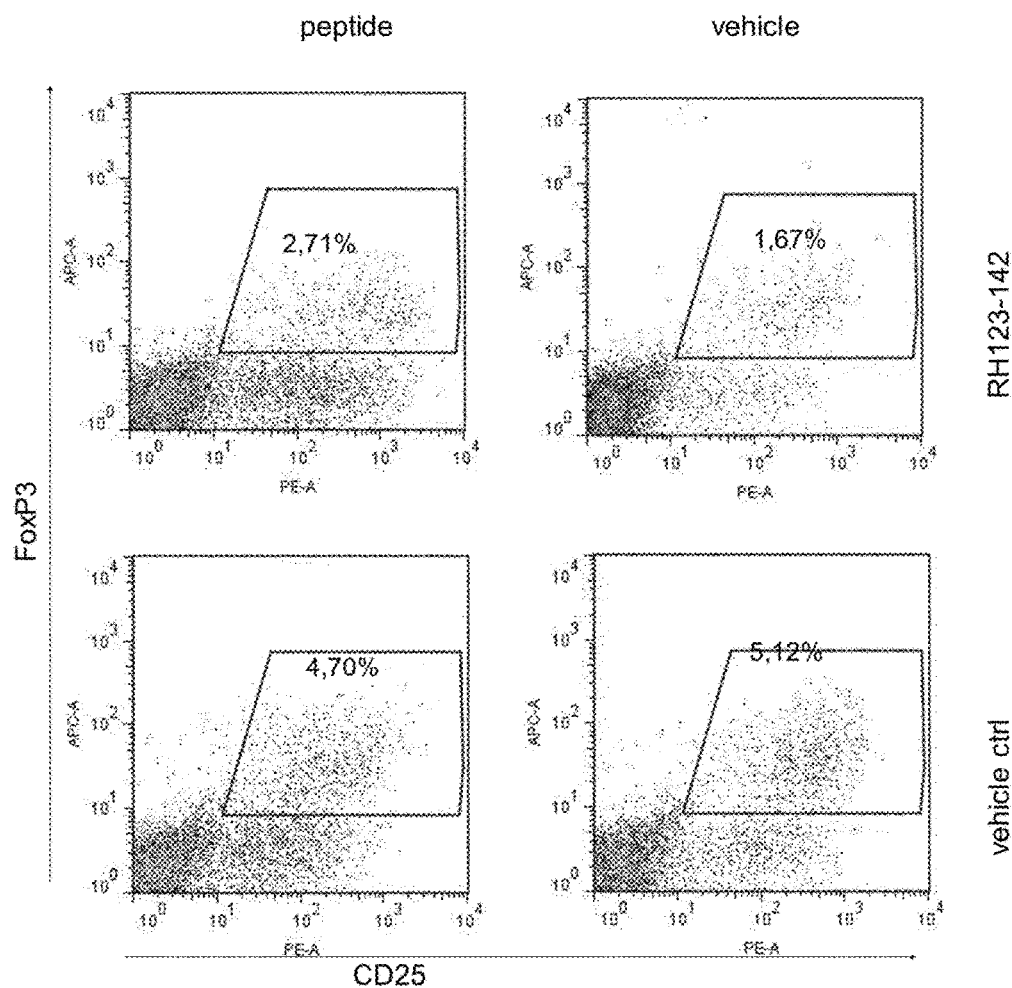
Figure 8A:
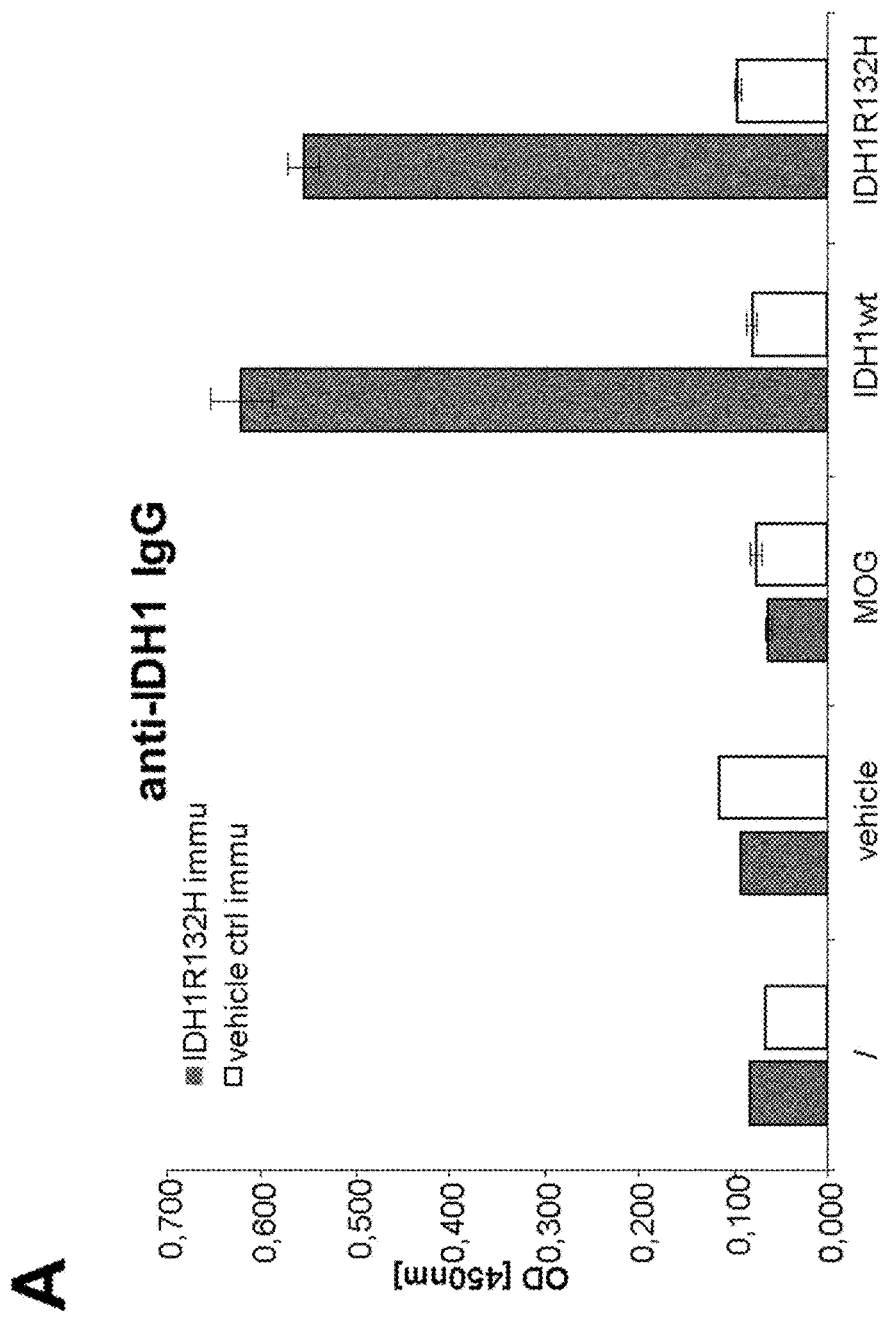
Figure 8B:
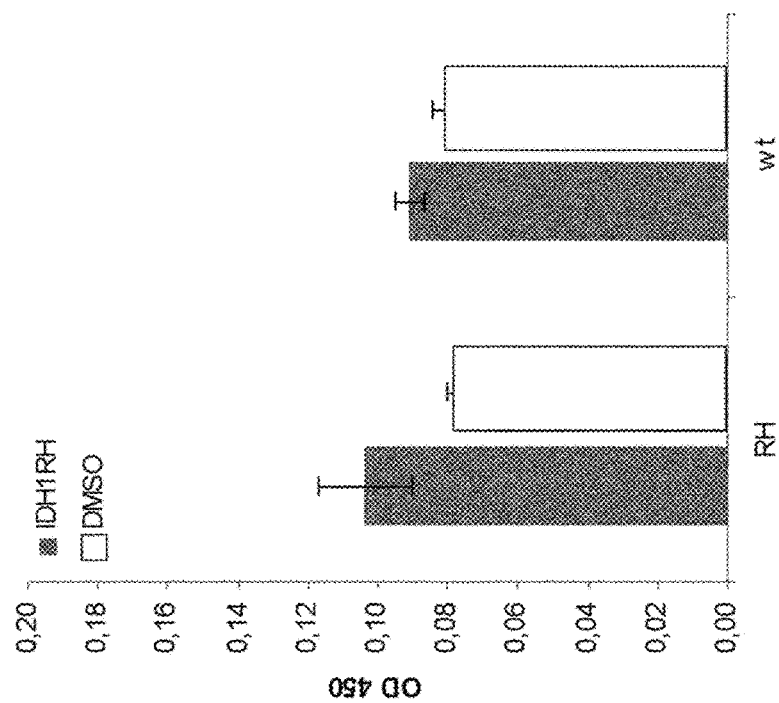
Figure 8B:
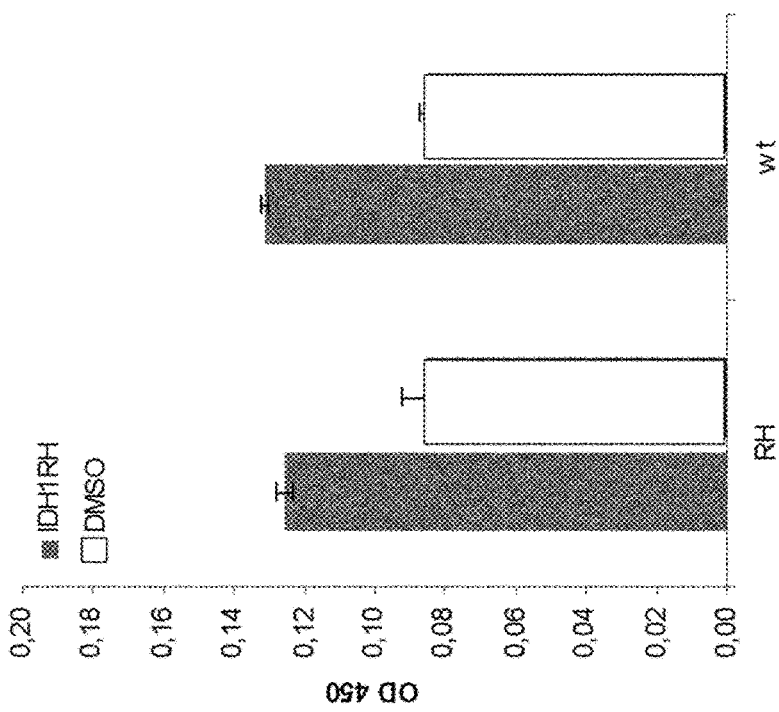
Figure 8B:
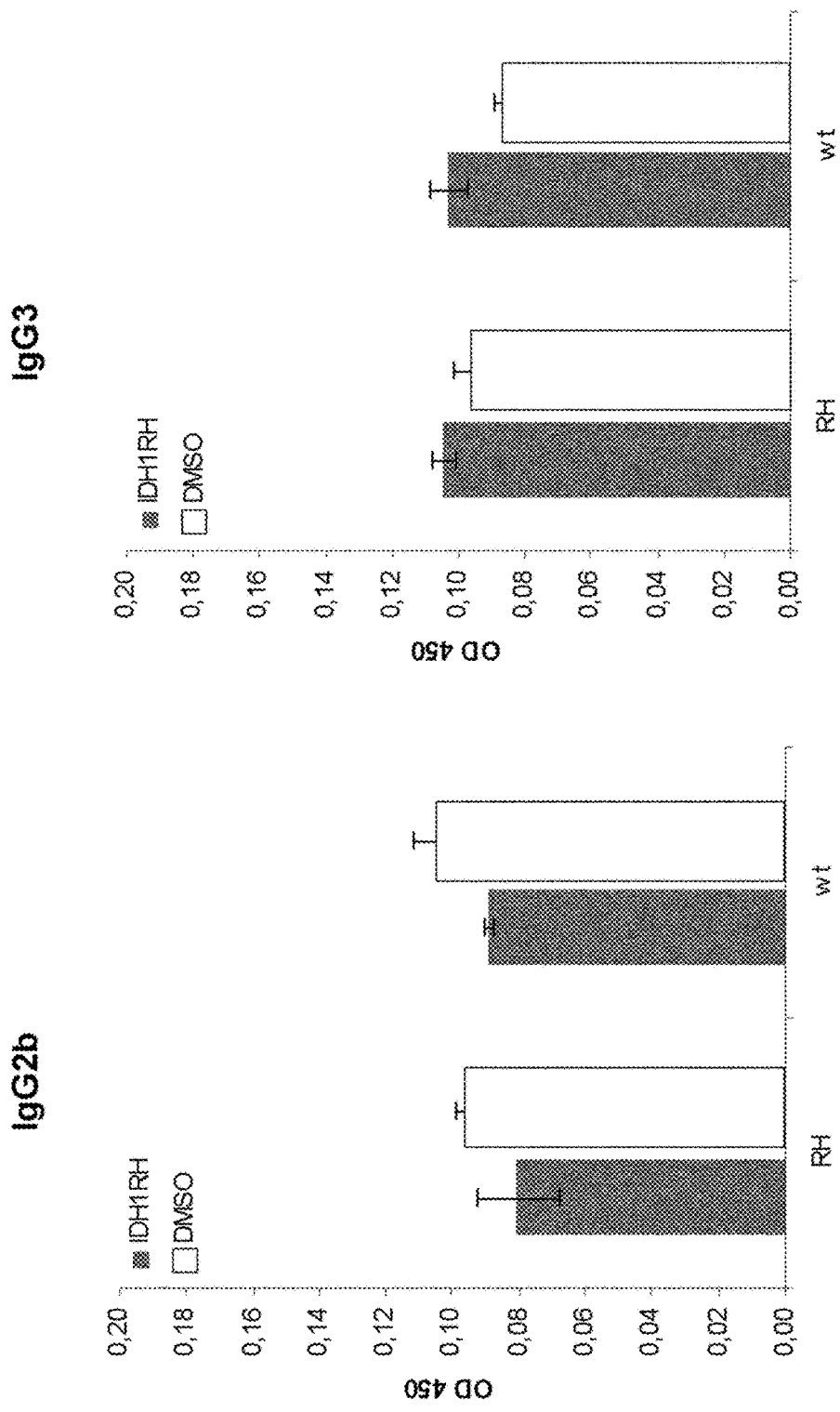
Figure 8B:
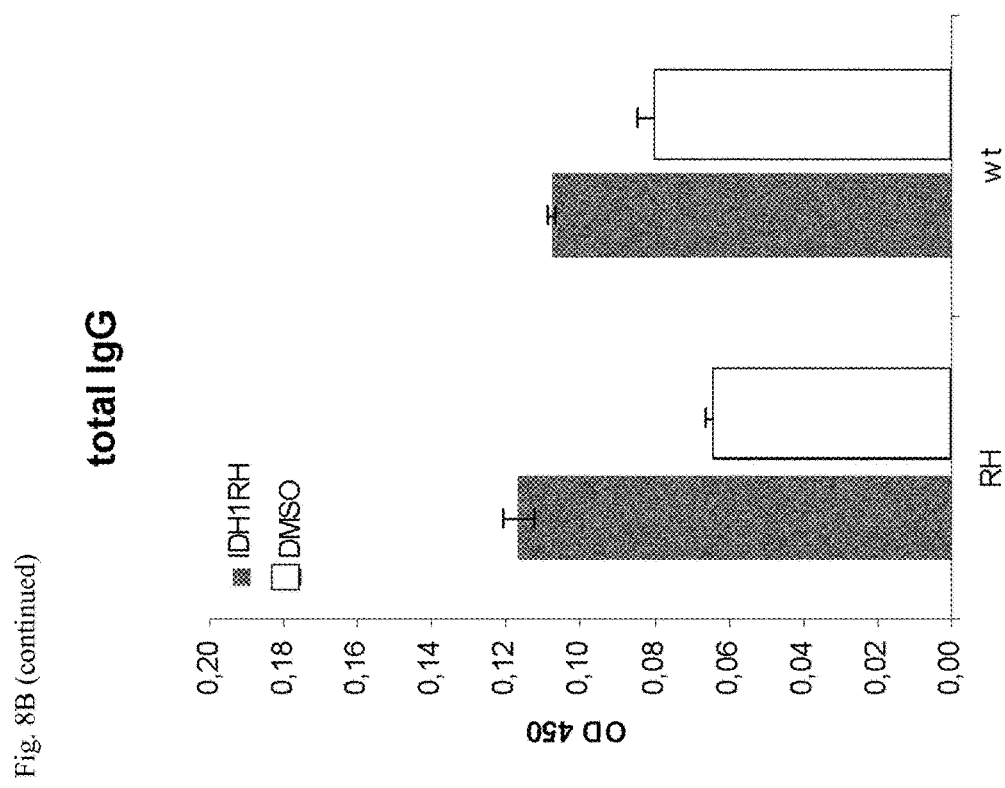
Figure 9A:
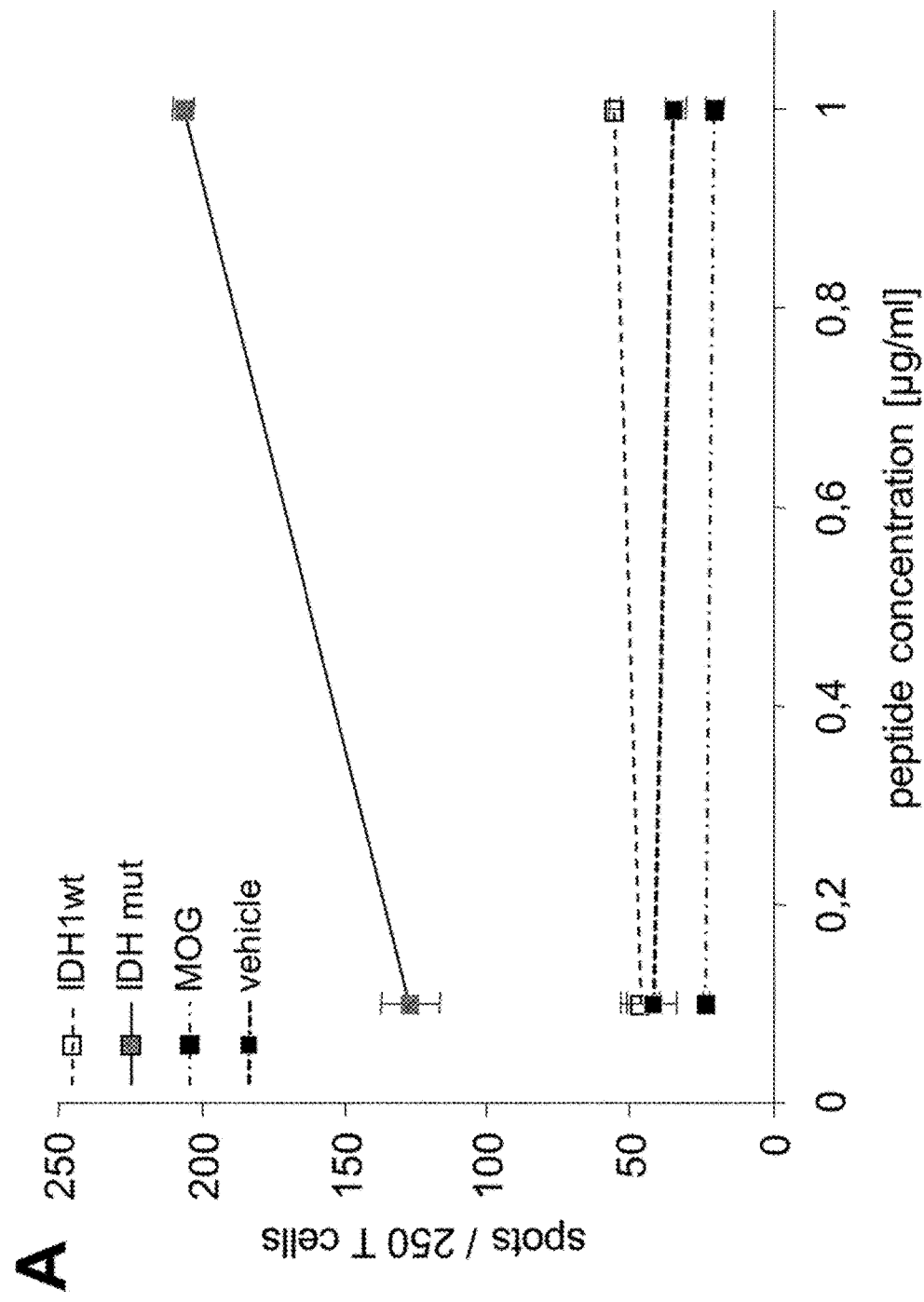
Figure 9B:
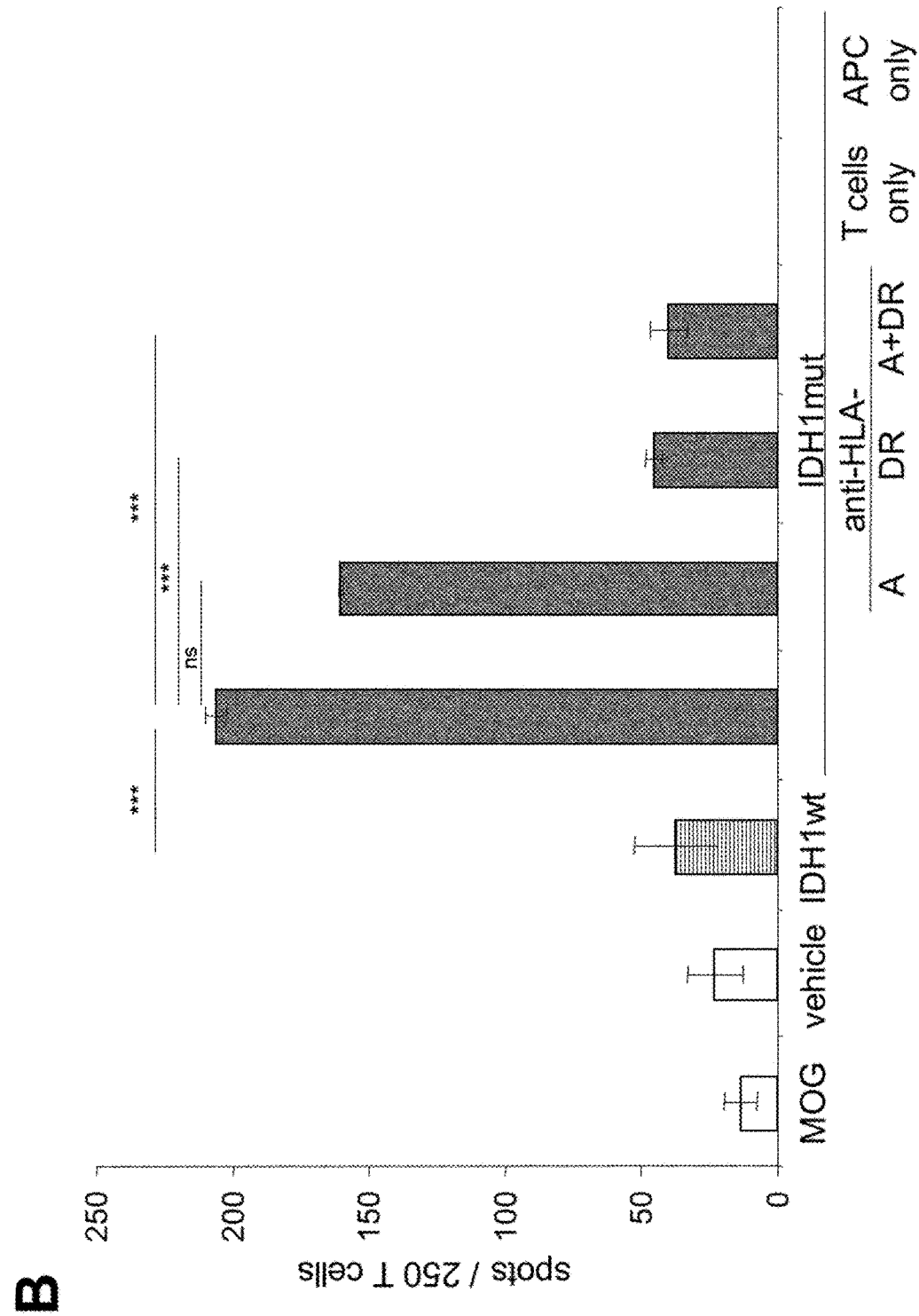
Figure 9C:
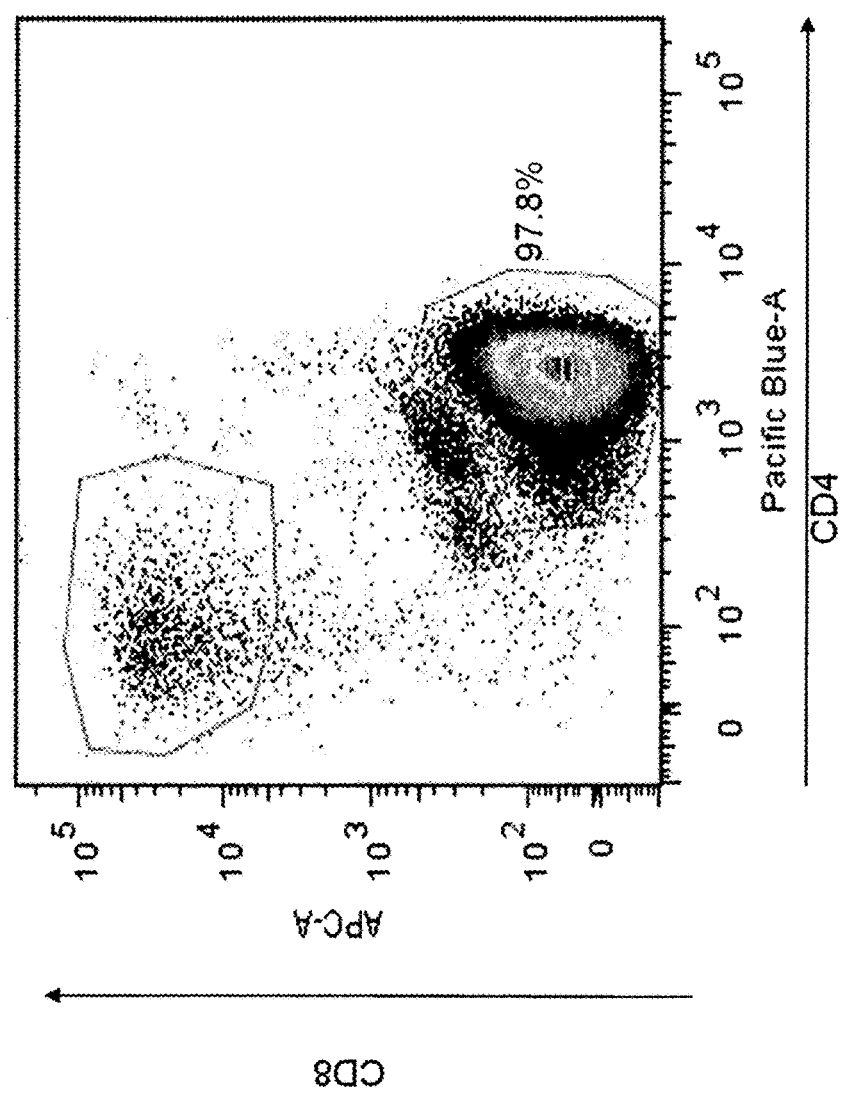
Figure 9D:
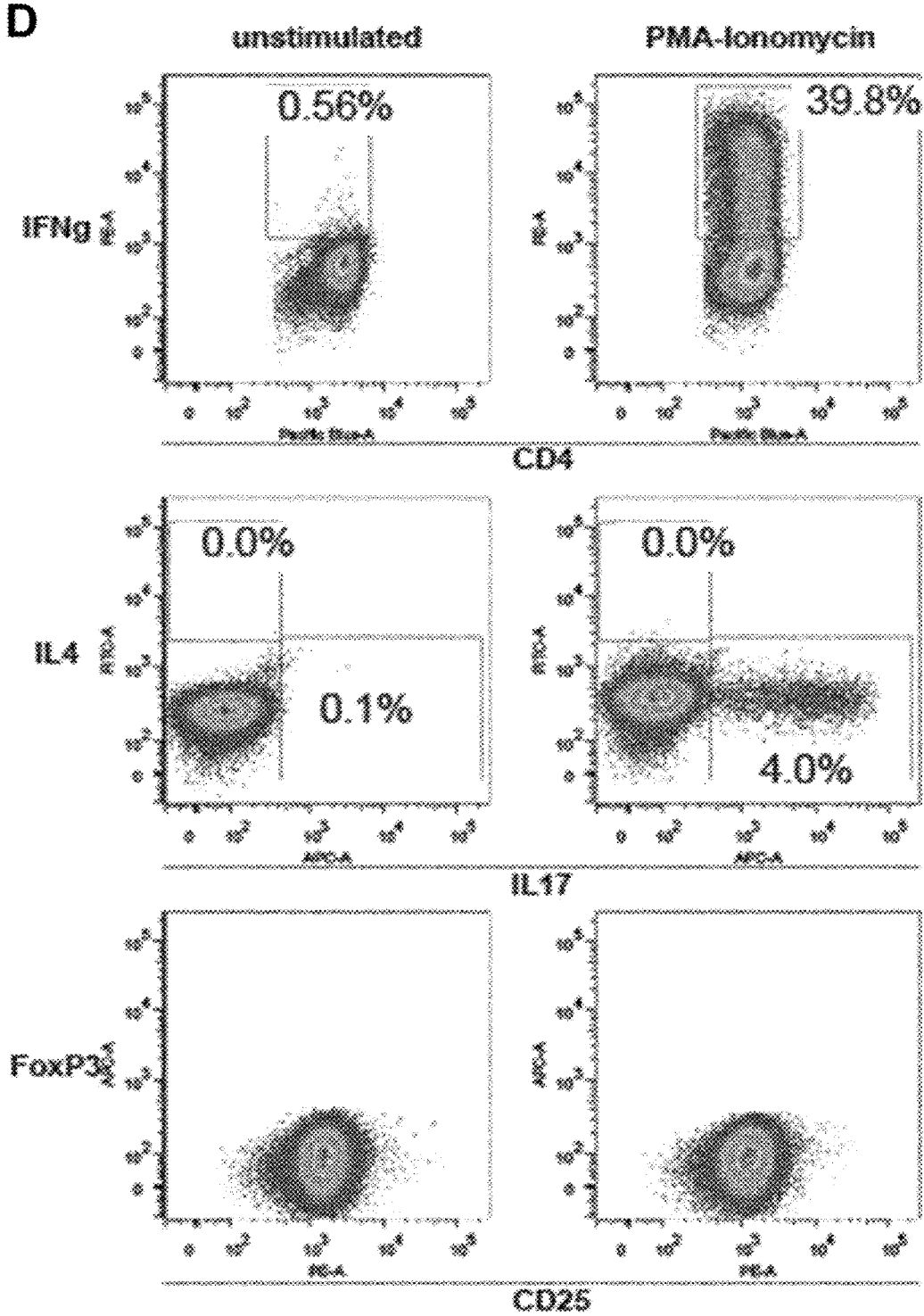
Figure 9E:
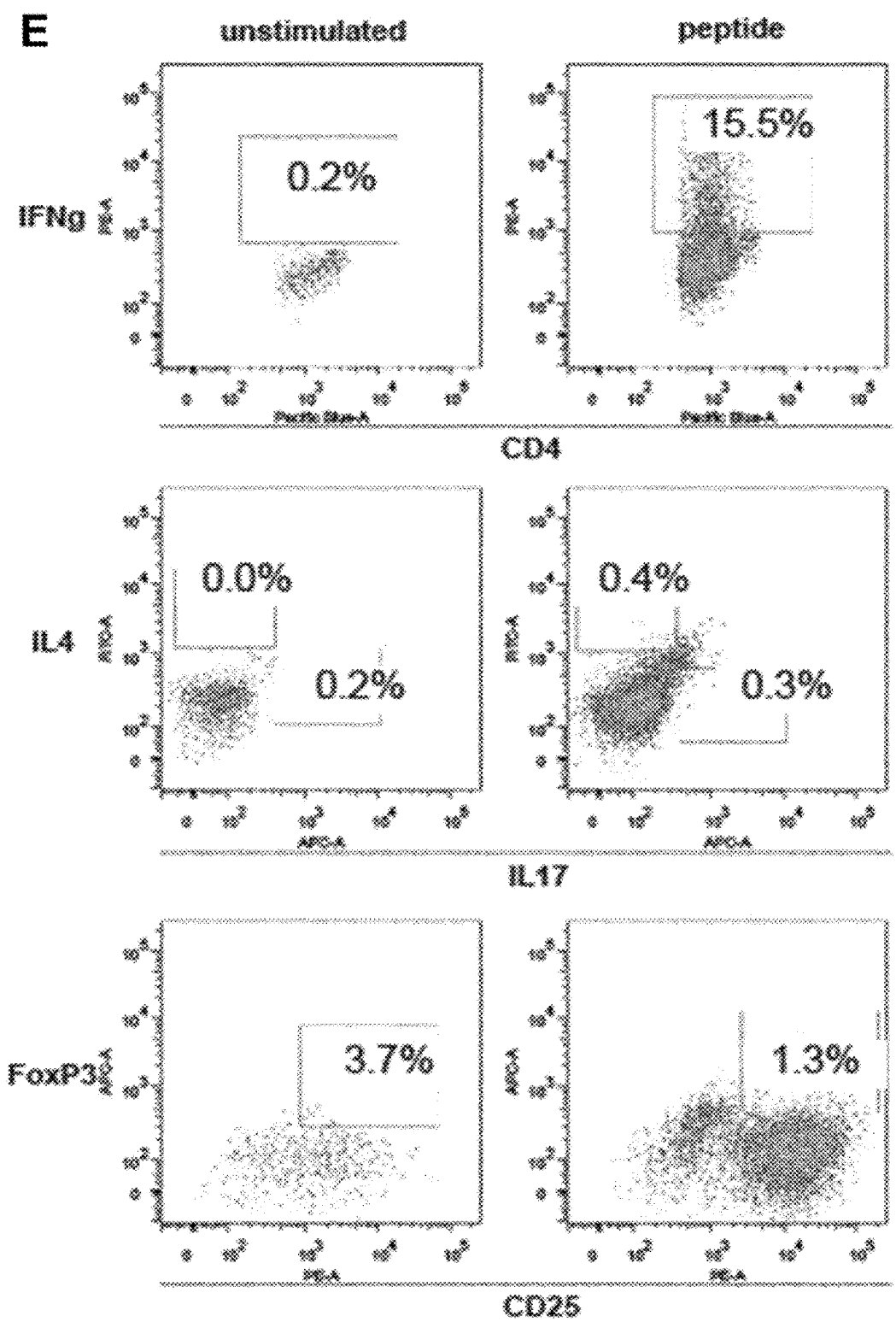

FIG. 7: IDH1R132H peptide vaccination does not induce Th2 nor Th17 cytokines A2.DR1 mice were immunized with 100 µg IDH1R132H$_{123-142}$ peptide in Montanide ISA51, 300 ng GM-CSF and 50 µl Aldara Cream (5% Imiquimod) and boosted after 14 days without GM-CSF. Control mice were treated in the same manner without peptide. After an additional 14 days, spleens and lymphnodes were excised for analysis. A) Splenocytes were stimulated with 10 µg/ml IDH1R132H, IDH1wt peptides, negative control peptide (MOG), with vehicle only or with 20 ng/ml PMA and 1

µg/ml ionomycin as positive control for 72 h. Supernatants were harvested and cytokines were colorimetrically quantified in triplicates in an anti-cytokine-coated ELISA using a standard curve with biotinylated anti-cytokine antibody, streptavidin-HRP and TMB. B) IFNγ-producing splenocytes were analysed via cytokine flow cytometry. Splenocytes were stimulated ex vivo with IDH1R132H$_{123-142}$ or vehicle control, restimulated with mit 20 ng/ml PMA and 1 µg/ml Ionomycin for 5 h including Golgi transport inhibitor 5 µg/ml Brefeldin A for secretion inhibition. Surface markers CD3, CD4, and CD25 were stained and for intracellular staining, cells were permeabilized and fixed and IL4, IL17, and FoxP3 were stained. Cells were analysed in a flow cytometer. Upper panels, IDH1R132H vaccinated mouse; lower panels, vehicle control vaccinated mouse. Left; Th2 and Th17; right, Treg. Representative results of one mouse are shown.

FIG. 8: IDH1R132H peptide vaccination induces IgG production A2.DR1 mice were immunized with 100 µg IDH1R132H$_{123-142}$ peptide in Montanide ISA51, 300 ng GM-CSF and 50 µl Aldara Cream (5% Imiquimod) and boosted after 14 days without GM-CSF. Control mice (DMSO) were treated in the same manner without peptide. After an additional 14 days, blood from submandibular vein was drawn to obtain serum. Serum from IDH1R132H vaccinated and vehicle control vaccinated mice was tested for IDH1-binding total IgG (A) and IgG subtypes (B) in IDH1R132H or IDH1wt peptide-coated ELISA using HRP-coupled anti-IgG antibody and TMB.

FIG. 9: CD4 T cell line is MHC class II DR-dependent and mutation-specific A2.DR1 mice were immunized with 100 µg IDH1R132H$_{123-142}$ peptide in Montanide ISA51, 300 ng GM-CSF and 50 µl Aldara Cream (5% Imiquimod) and boosted after 14 days without GM-CSF. Control mice were treated in the same manner without peptide. After an additional 14 days, spleens were excised and stimulated with 10 µg/ml IDH1R132H$_{123-142}$. To generate a CD4+ IDH1R132H$_{123-142}$ specific T cell line, cells were restimulated every 4 weeks with isogenic irradiated splenocytes loaded with 2 µg/ml IDH1R132H$_{123-142}$ and ConA and analysed after 3 restimulations. A) $10^5$ B-cell blasts were generated from isogenic splenocytes over 3 days with 2 µg/ml LPS and 7 µg/ml dextransulfate, loaded with 0.1 or 1.0 µg/ml (A) IDH1R132H$_{123-142}$, IDH1wt$_{123-142}$ negative controle peptide (MOG) or with vehicle and used for stimulation of 250 cells of the CD4+ T cell line. B) Stimulation with B cell blasts loaded with 0.1 µg/ml (A) IDH1R132H$_{123-142}$ was inhibited with 0.2 µg/ml HLA-A or HLA-DR blocking antibodies. IFNγ production was measured after 38 h by ELISpot. ***p<0,005. C) CD4 expression by IDH1R132H$_{123-142}$-specific T cells was confirmed by staining for surface markers CD3, CD4, and CD8 and flow cytometry. D) IDH1R132H$_{123-142}$ specific T cells were stimulated with for 5 h 20 ng/ml PMA and 1 µg/ml Ionomycin including Golgi transport inhibitor 5 µg/ml Brefeldin A for secretion inhibition. Surface markers CD3, CD4, and CD25 were stained and for intracellular staining, cells were permeabilized and fixed and IFNγ, IL4, IL17, and FoxP3 were stained. Cells were analysed in a flow cytometer. E) IDH1R132H$_{123-142}$ specific T cells were stimulated with isogenic DC (T cells:DC 1:5), which had been generated from bone marrow with 20 ng/ml GM-CSF for 5 days, loaded with 4 µg/ml IDH1R132H$_{123-142}$. For intracellular cytokine staining, cells were treated with 5 µg/ml Brefeldin A for secretion inhibition and stained for flow cytometry as in (D).

Figure 10A:
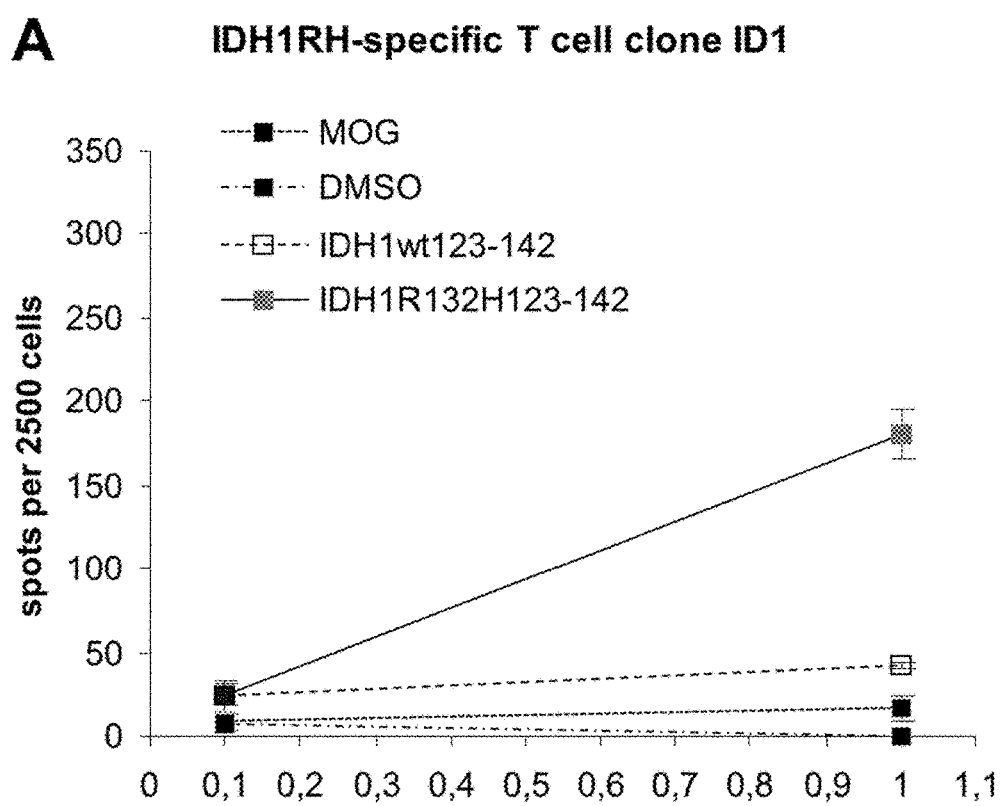
Figure 10B:
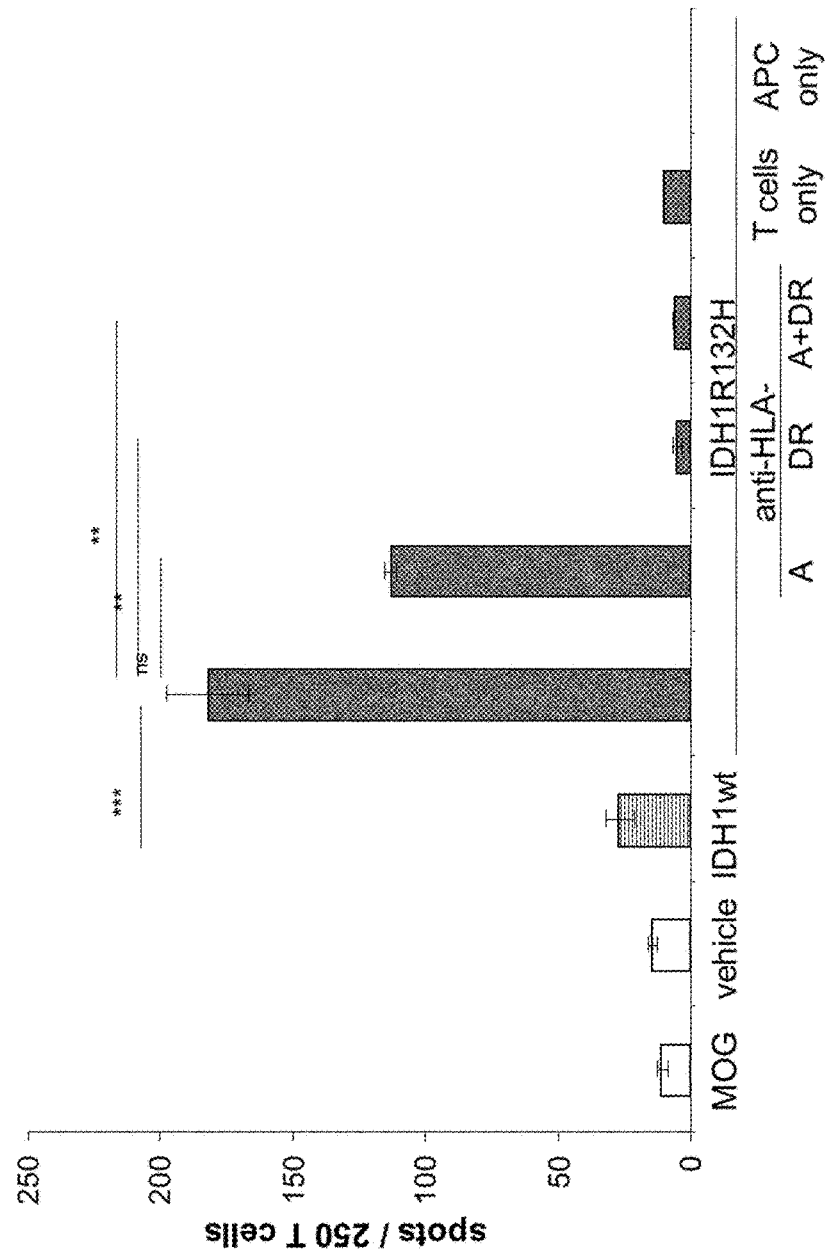
Figure 11A:
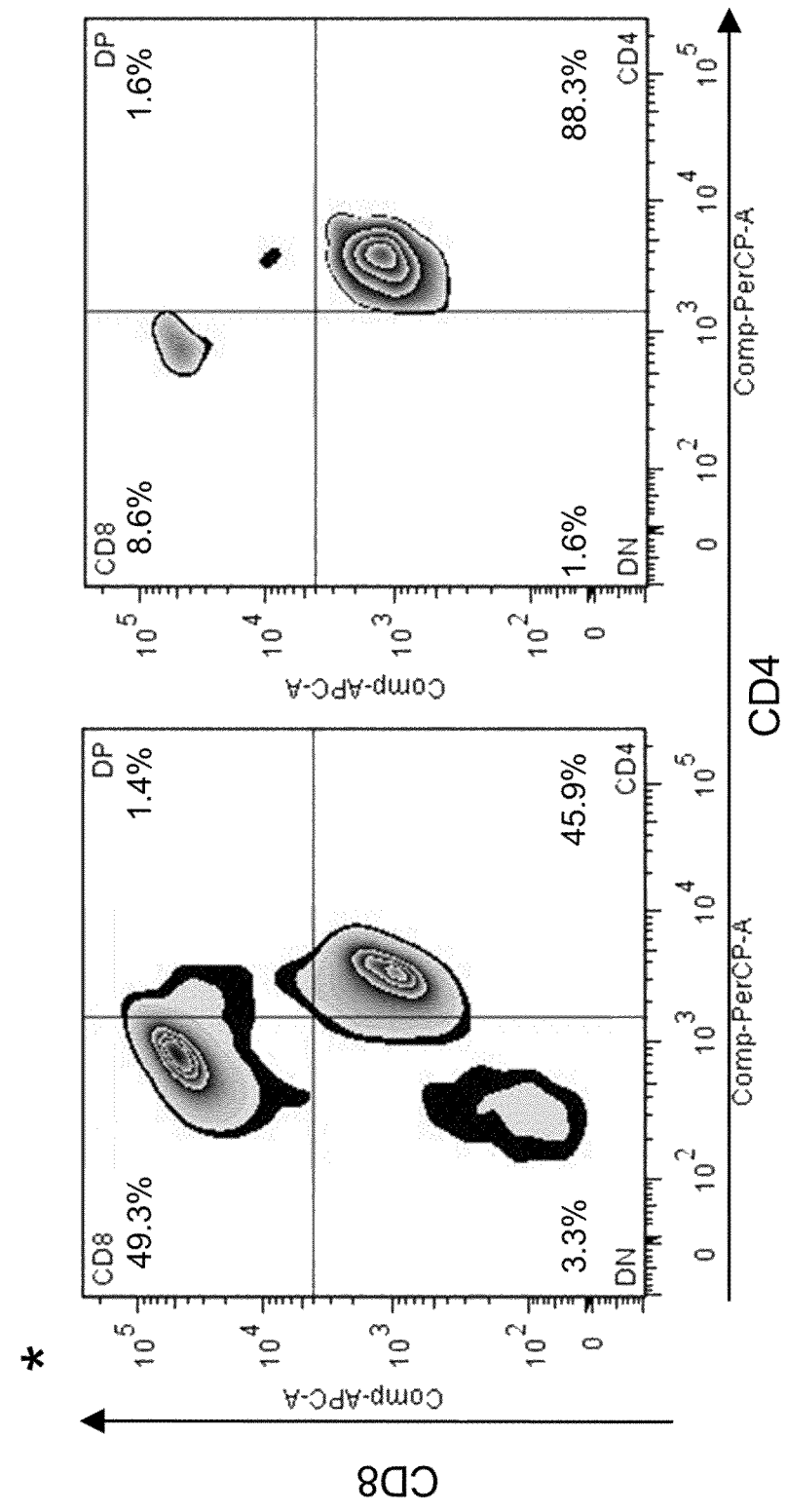
Figure 11B:
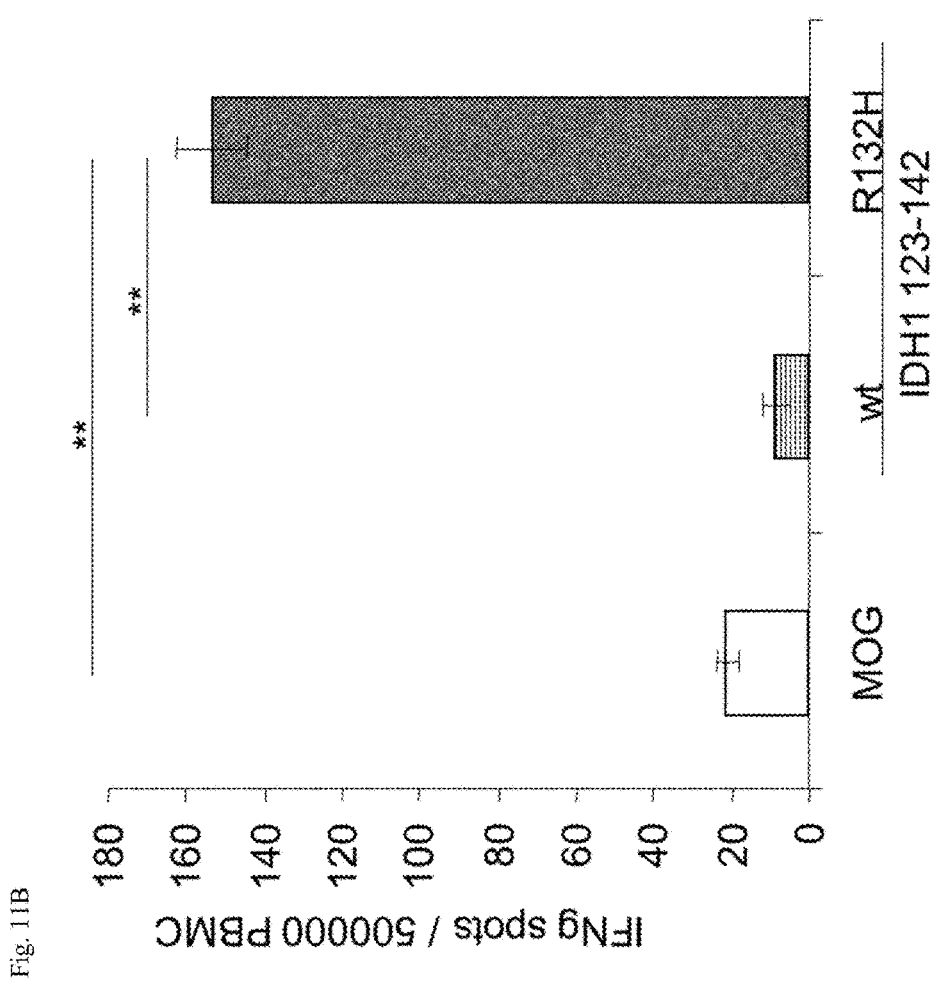
Figure 11C:
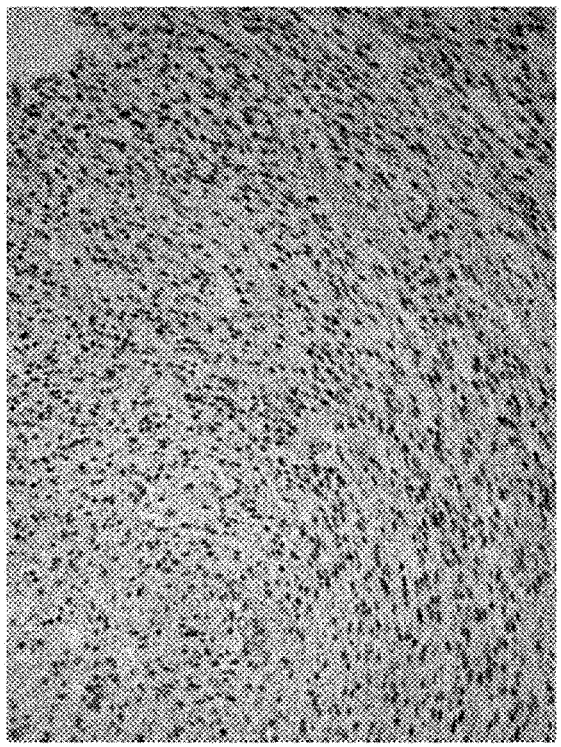
Figure 11C:
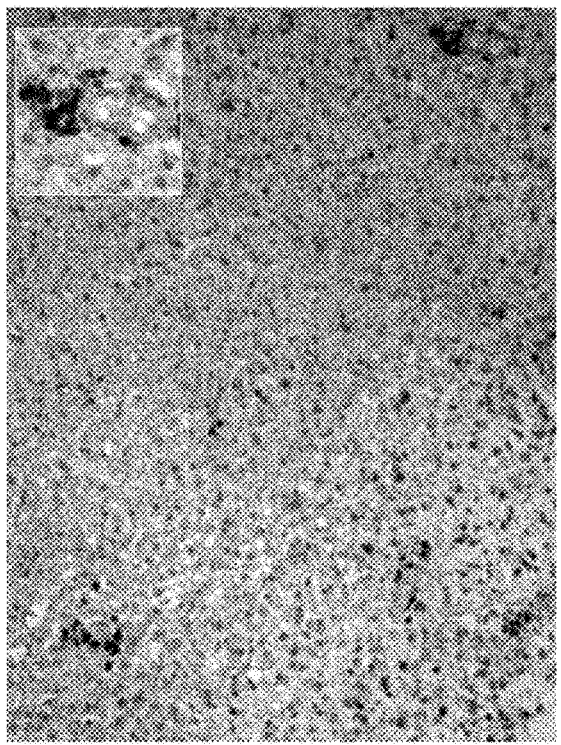

FIG. 10: CD4 T cell clone is MHC class II DR-dependent and mutation-specific Single cell clones were generated from CD4+ IDH1R132H$_{123-142}$ specific T cell line and restimulated every 4 weeks with isogenic irradiated splenocytes loaded with 2 µg/ml IDH1R132H$_{123-142}$ and ConA. A) $10^5$ B-cell blasts were generated from isogenic splenocytes over 3 days with 2 µg/ml LPS and 7 µg/ml dextransulfate, loaded with 0.1 or 1.0 µg/ml (A) IDH1R132H$_{123-142}$, IDH1wt$_{123-142}$ negative controle peptide (MOG) or with vehicle and used for stimulation of 2500 cells of the CD4+ T cell clone. B) Stimulation with B cell blasts loaded with 0.1 µg/ml (A) IDH1R132H$_{123-142}$ was inhibited with 0.2 µg/ml HLA-A or HLA-DR blocking antibodies. IFNγ production was measured after 38 h by ELISpot. p<0.01; *p<0.005.

FIG. 11: IDH1R132H-specific IFNγ response in GBM patient is Th1-mediated A) $10^7$ PBMC were isolated from peripheral blood of an IDH1R132H+ GBM patient and stimulated for 6 h with 40 µg/ml IDH1R132H$_{123-142}$, negative control peptide MOG or 1 µg/ml Staphylococcus Enterotoxin B (SEB) as positive control, and IFNγ-producing cells were isolated via catch assay. Cells were labeled with anti-IFNγ antibody as catch reagent for catching of secreted IFNγ on the cell surface during a 45 min secretion period. Cells were labeled with PE-coupled IFNγ-specific antibody and anti-PE microbeads and magnetically sorted. IFNγ-producing were stained with surface markers CD3, CD4, and CD8 for flow cytometry, IFNγ negative cells (APC) were used as controls. B) $5*10^5$ PBMC of the same patient were stimulated with 20 µg/ml IDH1R132H$_{123-142}$, IDH1wt$_{123-142}$ or negative control peptide (MOG) for 38 h and IFNγ production was measured by ELISpot. **p<0.01. C) CD3+ tumor infiltrating T cells were stained in tumor tissue of the same patient (left) and of a patient with anaplastic glioma (A° III).

Figure 12:
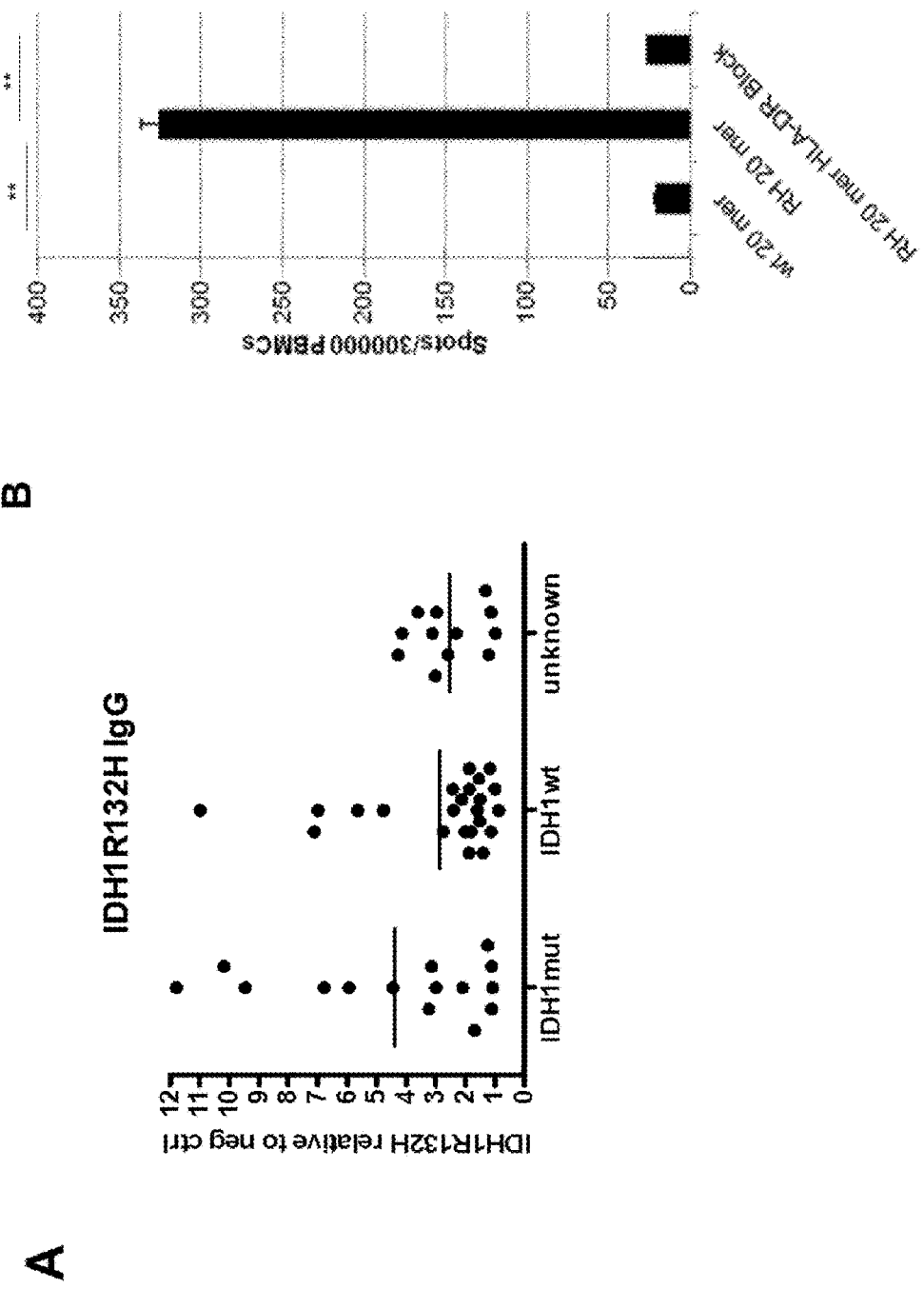

FIG. 12: Humoral and cellular IDH1R132H response in IDH1R132H+ glioma patients A) Sera from IDH1R132H+ and IDH1wt glioma patients were tested for IDH1R132H-specific IgG in IDH1R132H$_{122-136}$ peptide ELISA. The plate was coated with 10 µg IDH1R132H$_{122-136}$ peptide per well, blocked with 3% FBS and serum was incubated for binding of IgG to peptide. IgG was colorimetrically detected with HRP-coupled anti-human IgG antibody and TMB. For negative control, MOG peptide was coated. Shown are values relative to MOG peptide. Data are from 50 patients total, of which 15 with IDH1R132H, 23 with IDH1wt, and 12 with unknown IDH1 status. B) $5*10^5$ PBMC were isolated from peripheral blood of an IDH1R132H+ glioma patient and stimulated for 38 h with 20 µg/ml IDH1wt$_{123-142}$ or IDH1R132H$_{123-142}$ and treated with HLA-DR blocking antibody. IFNγ production was quantified with ELISpot. **p<0.01.

Figure 13:
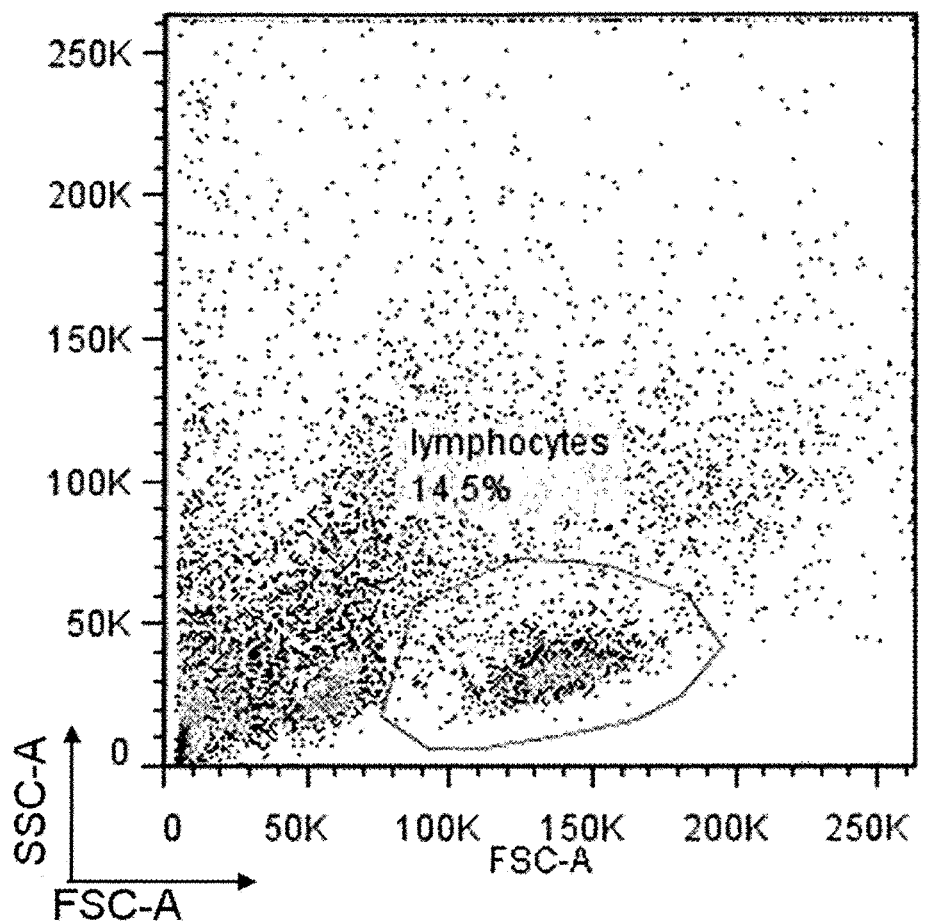
Figure 13:
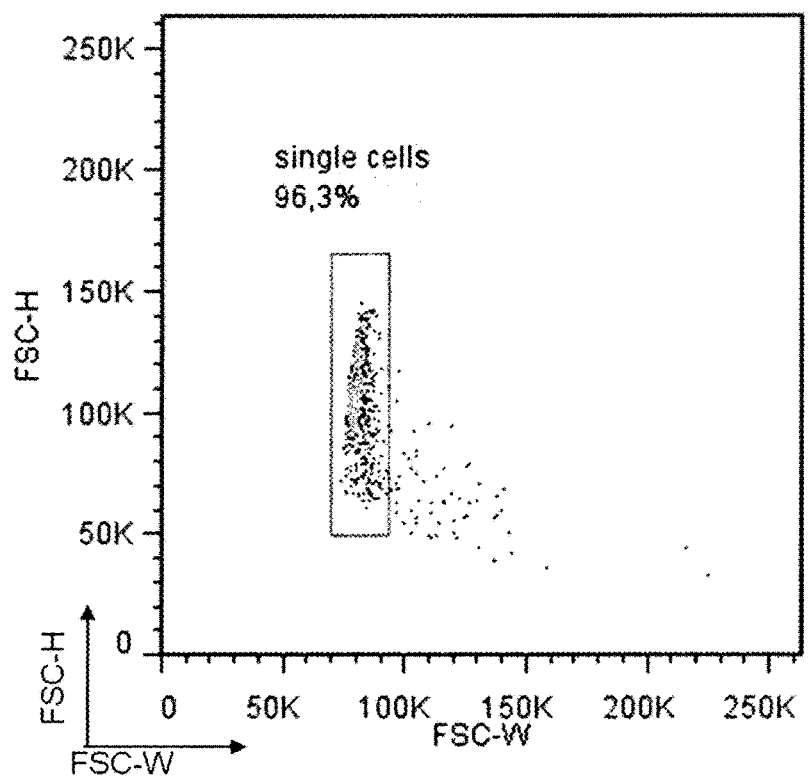
Figure 13:
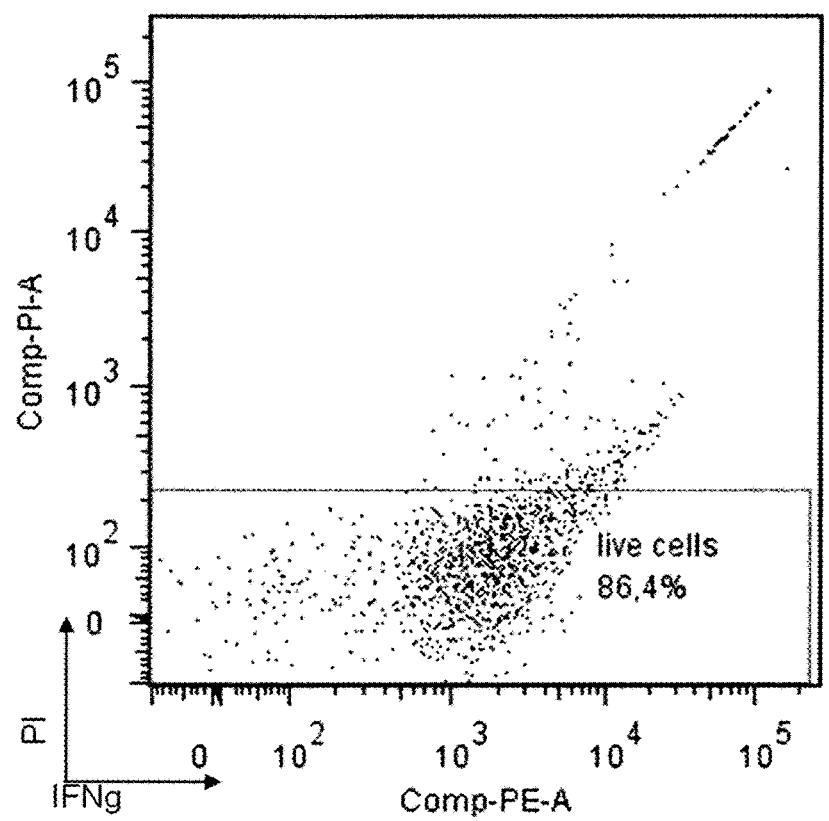
Figure 13:
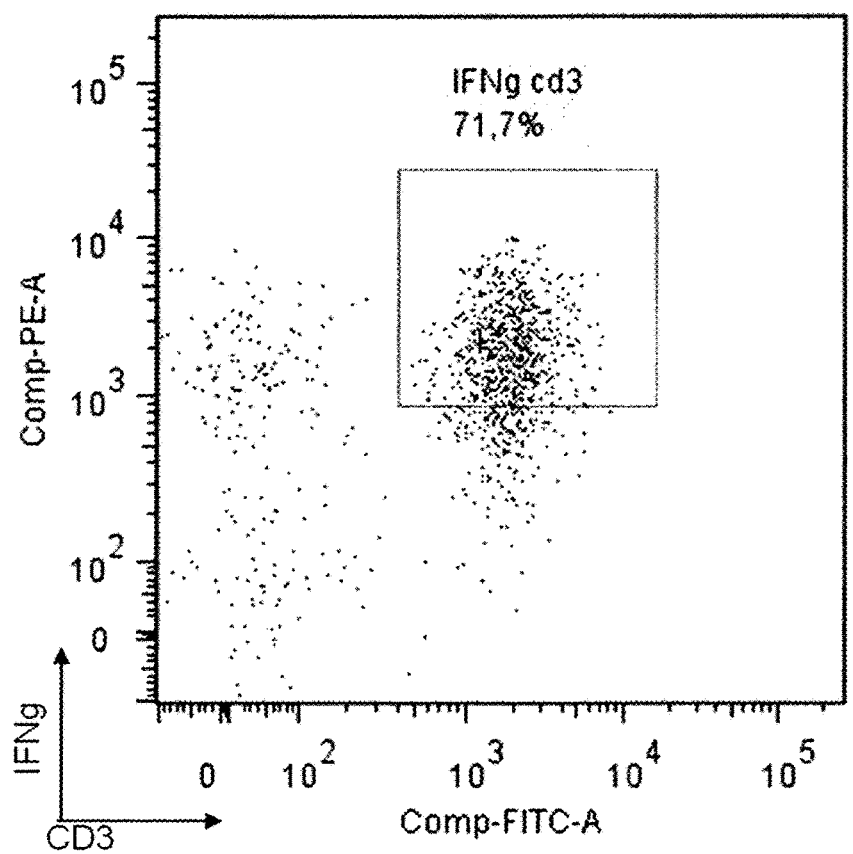
Figure 13:
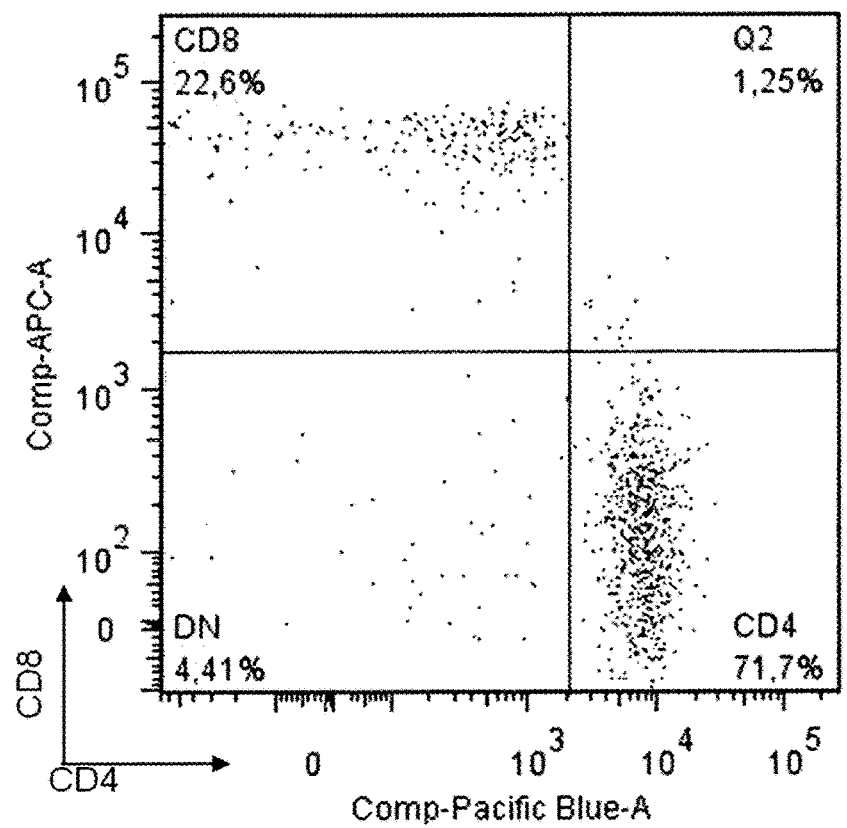

FIG. 13: Establishment of IDH1R132H IFNγ catch assay staining and gating strategy A) $10^7$ PBMC were isolated from peripheral blood of IDH1R132H+ glioma patients and stimulated for 6 h with 40 µg/ml IDH1R132H$_{123-142}$, negative control peptide MOG or 1 µg/ml Staphylococcus Enterotoxin B (SEB) as positive control, and IFNγ-producing cells were isolated via catch assay. Cells were labeled with anti-IFNγ antibody as catch reagent for catching of secreted IFNγ on the cell surface during a 45 min secretion period. Cells were labeled with PE-coupled IFNγ-specific antibody and anti-PE microbeads and magnetically sorted. IFNγ-producing and IFNγ negative cells (APC) were stained with surface markers CD3, CD4, and CD8 and dead cells were labeled with PI for flow cytometry.

FIG. 14: Absence of IDH1R132H-specific IFNγ-responsive T cells in glioma patients $10^7$ PBMC were isolated from peripheral blood of IDH1R132H+ glioma patients and stimulated for 6 h with 40 μg/ml IDH1R132H$_{123-142}$, negative control peptide MOG or 1 μg/ml *Staphylococcus* Enterotoxin B (SEB) as positive control, and IFNγ-producing cells were isolated via catch assay. Cells were labeled with anti-IFNγ antibody as catch reagent for catching of secreted IFNγ on the cell surface during a 45 min secretion period. Cells were labeled with PE-coupled IFNγ-specific antibody and anti-PE microbeads and magnetically sorted. IFNγ-producing and IFNγ negative cells (APC) were stained with surface markers CD3, CD4, and CD8 and dead cells were labeled with PI for flow cytometry. A) Patient 010275, B) Patient 270284, C) Patient 080572.

FIG. 15: Presence of IDH1R132H-specific IFNγ-responsive T cells in glioma patients $10^7$ PBMC were isolated from peripheral blood of IDH1R132H+ glioma patients and stimulated for 6 h with 40 μg/ml IDH1R132H$_{123-142}$, negative control peptide MOG or 1 μg/ml *Staphylococcus* Enterotoxin B (SEB) as positive control, and IFNγ-producing cells were isolated via catch assay. Cells were labeled with anti-IFNγ antibody as catch reagent for catching of secreted IFNγ on the cell surface during a 45 min secretion period. Cells were labeled with PE-coupled IFNγ-specific antibody and anti-PE microbeads and magnetically sorted. IFNγ-producing and IFNγ negative cells (APC) were stained with surface markers CD3, CD4, and CD8 and dead cells were labeled with PI for flow cytometry. A) Patient 170185, B) Patient 150161.

EXAMPLES

The following Examples shall merely illustrate the invention. They shall not be construed, whatsoever, to limit the scope of the invention.

Example 1

Identification of a MHCII-Restricted anti-IDH1R132H CD4+ T Cell Response and Antibody Production in IDH1R132H-Vaccinated MHCII-Humanized Mice The peripheral immune response to IDH1R132H was tested in transgenic mice devoid of mouse MHC class I and II but transgenic for human A2 and DR1 to mimick the antigen presentation in a human class I and class II context. These experiments (FIG. 2) revealed that after immunization with IDH1R132H peptides 123-142, 124-138 and 122-136 restimulation ex vivo with various mutation-specific peptides, that (a) the mutated 123-142 and 122-136 peptides but not 124-138 are immunogenic. The specific immunogenicity of 123-142 was recapitulated when analyzing the antibody response in vaccinated humanized mice. These experiments indicate, that after immunization IDH1 mutation-specific antibodies are generated (FIG. 3)

Example 2

Immunogenicity of IDH1R132H 123-142 in Patients with IDH1R132H Mutated Gliomas

The immunogenicity of IDH1R132H 123-142 was also shown in patients with IDH1R132H mutated gliomas where a natural CD4 T cell response was detected (FIG. 1) and natural IDHR132H-specific antibodies were evident in patients with IDH1R132H mutated gliomas but not healthy controls of IDH1 wildtype gliomas (FIG. 4). These antibodies appeared to be largely of the same epitope specificity with a preference for 122-136 and 126-140 (FIG. 5).

The invention claimed is:

1. A medicament comprising
   a peptide selected from the group consisting of
      an amino acid sequence consisting of the amino acids corresponding to SEQ ID NO: 1;
      an amino acid sequence consisting of the amino acids corresponding to SEQ ID NO: 2; and
      an amino acid sequence consisting of the amino acids corresponding to SEQ ID NO: 9, and
   a pharmaceutically acceptable carrier selected from the group consisting of terra alba, sucrose, talc, gelatin, agar, pectin, acacia, stearic acid, syrup, glyceryl mono-stearate, glyceryl mono-stearate with a wax, glyceryl distearate, and glyceryl distearate with a wax.

2. The medicament of claim 1, wherein the peptide consists of the amino acid sequence of SEQ ID NO: 9.

3. A device for diagnosing cancer having a mutation in the genome of at least some cancer cells which results in the expression of a mutant IDH1 having the R132H mutation, comprising:
   a) an analyzing unit comprising
      a peptide selected from the group consisting of
         an amino acid sequence consisting of the amino acids corresponding to SEQ ID NO: 1;
         an amino acid sequence consisting of the amino acids corresponding to SEQ ID NO: 2; and
         an amino acid sequence consisting of the amino acids corresponding to SEQ ID NO: 10;
         arranged for detection of a component of the immune system in a sample of a subject; and
         a detection agent capable of generating a detectable signal and binding a complex comprising said peptide and the component of the immune system; and
   b) an evaluation unit comprising a detector capable of detecting specific binding of the component of the immune system to the said peptide,
      wherein said detector generates an output signal indicating whether a specific binding of the component to the peptide occurs,
      wherein the component is a T-lymphocyte, a B-lymphocyte, or a dendritic cell, and
      wherein the cancer is a glioma.

4. The device of claim 3, wherein the peptide consists of the amino acid sequence of SEQ ID NO: 10.

5. A kit for diagnosing cancer having a mutation in the genome of at least some cancer cells which results in expression of a mutant IDH1 having the R132H mutation, comprising
   instructions for carrying out said method,
   a peptide selected from the group consisting of
      an amino acid sequence consisting of the amino acids corresponding to SEQ ID NO: 1;
      an amino acid sequence consisting of the amino acids corresponding to SEQ ID NO: 2;
      an amino acid sequence consisting of the amino acids corresponding to SEQ ID NO: 10; and
   a detection agent capable of generating a detectable signal and binding a complex comprising said peptide and a component of the immune system,
      wherein the component is a T-lymphocyte, a B-lymphocyte or a dendritic cell, and
      wherein the cancer is a glioma.

6. The kit of claim 5, wherein the peptide consists of the amino acid sequence of SEQ ID NO: 10.

7. A method for diagnosing cancer having a mutation in the genome of at least some tumor cells, which result in expression of a mutant IDH1 having the R132H mutation, comprising:
   a) contacting a blood sample of a subject suspected to suffer from such a cancer with a peptide selected from the group consisting of
      an amino acid sequence consisting of the amino acids corresponding to SEQ ID NO: 1;
      an amino acid sequence consisting of the amino acids corresponding to SEQ ID NO: 2; and
      an amino acid sequence consisting of the amino acids corresponding to SEQ ID NO: 10;
      which allow for specific binding of a cell of the immune system in the blood sample to the peptide;
   b) isolating an IFN-γ producing cell from the blood sample contacted with the peptide;
   c) providing a detection agent capable of generating a detectable signal for binding a complex comprising said peptide and the IFN-γ producing cell of the immune system;
   d) determining whether binding of said IFN-γ producing cell of the immune system to the peptide occurs by measuring the level of the detectable signal, wherein the cancer is diagnosed if the level of the detectable signal is greater than a pre-determined level, and wherein the cancer is a glioma.

8. The method of claim 7, wherein said cell of the immune system is a lymphocyte.

9. The method of claim 7, wherein said glioma is selected from the group consisting of WHO II or WHO III astrocytoma, oligodendroglioma, oligoastrocytoma, glioblastoma and gliosarcoma.

10. The method of claim 7, wherein the peptide consists of the amino acid sequence of SEQ ID NO: 10.

* * * * *